(12) United States Patent
Yang et al.

(10) Patent No.: US 11,921,118 B2
(45) Date of Patent: Mar. 5, 2024

(54) METHODS FOR PROTEOME LABELING

(71) Applicants: The Board of Trustees of the Leland Stanford Junior University, Stanford, CA (US); The United States Government as represented by the Department of Veterans Affairs, Washington, DC (US)

(72) Inventors: Andrew Yang, Stanford, CA (US); Anton Wyss-Coray, Stanford, CA (US); Kyle Brewer, Stanford, CA (US)

(73) Assignees: The Board of Trustees of the Leland Stanford Junior University, Stanford, CA (US); The United States Government as represented by the Department of Veterans Affairs, Washington, DC (US)

( * ) Notice: Subject to any disclaimer, the term of this patent is extended or adjusted under 35 U.S.C. 154(b) by 390 days.

(21) Appl. No.: 17/090,261

(22) Filed: Nov. 5, 2020

(65) Prior Publication Data
US 2021/0172959 A1   Jun. 10, 2021

Related U.S. Application Data

(63) Continuation of application No. PCT/US2019/031587, filed on May 9, 2019.

(60) Provisional application No. 62/669,907, filed on May 10, 2018.

(51) Int. Cl.
*G01N 33/68* (2006.01)
*C12N 9/00* (2006.01)

(52) U.S. Cl.
CPC ........... *G01N 33/6842* (2013.01); *C12N 9/93* (2013.01); *C12Y 601/01001* (2013.01); *C12Y 601/0102* (2013.01); *G01N 2333/9015* (2013.01)

(58) Field of Classification Search
CPC ....... G01N 33/6842; G01N 2333/9015; G01N 33/5743; G01N 2800/28; G01N 33/5091; C12N 9/93; C12Y 601/01001; C12Y 601/0102; C12Y 601/01; C12Q 1/25
See application file for complete search history.

(56) References Cited

FOREIGN PATENT DOCUMENTS

WO      2006/135096 A1   12/2006

OTHER PUBLICATIONS

Alborz Mahdavi Engineered Aminoacyl-tRNA Synthetase for Cell-Selective Analysis of Mammalian Protein Synthesis. J. Am. Chem. Soc. 2016, 138, 4278-4281 (Year: 2016).*
Alborz Mahdavi An engineered aminoacyl-tRNA synthetase for cellselective analysis of mammalian protein synthesis. this is supplemental data (Year: 2016).*
Beatriz Alvarez-Castelao Cell-type-specific metabolic labeling of nascent proteomes in vivo. vol. 35 No. 12 Dec. 2017 (Year: 2017).*
International Patent Application No. PCT/US2019/031587, International Search Report and Written Opinion of the International Searching Authority, dated Nov. 8, 2019, 17 pages.
Serfling, R. et al., "Designer tRNAs for efficient incorporation of non-canonical amino acids by the pyrrolysine system in mammalian cells," Nucleic Acids Research, vol. 46, No. 1, Nov. 21, 2017, 10 pages.
Yokogawa, T. et al., "Incorporation of 3-Azidotyrosine into Proteins Through Engineering Yeast Tyrosyl-tRNA Synthetase and Its Application to Site-Selective Protein Modification," Methods in Molecular Biology, vol. 607, 2010, pp. 227-242.
Erdmann, I. et al., "Cell-Selective Labelling of Proteomes in *Drosophila melanogaster*," Nature Communications, 6:7521 doi: 10.1038/ncomms8521 (2015), 11 pages.

* cited by examiner

*Primary Examiner* — Iqbal H Chowdhury
(74) *Attorney, Agent, or Firm* — Kilpatrick Townsend & Stockton LLP

(57) ABSTRACT

Provided herein are methods for labeling the proteomes of cells, as well as methods for labeling proteins or populations of proteins produced by cells. In some embodiments, the methods comprise introducing variant aminoacyl-tRNA synthetases and noncanonical amino acids into cells. Also provided herein are polynucleotides encoding variant aminoacyl-tRNA synthetases that recognize noncanonical amino acids. The methods and compositions provided herein are useful for, among other things, identifying target cells and identifying biomarkers of interest.

18 Claims, 27 Drawing Sheets
Specification includes a Sequence Listing.

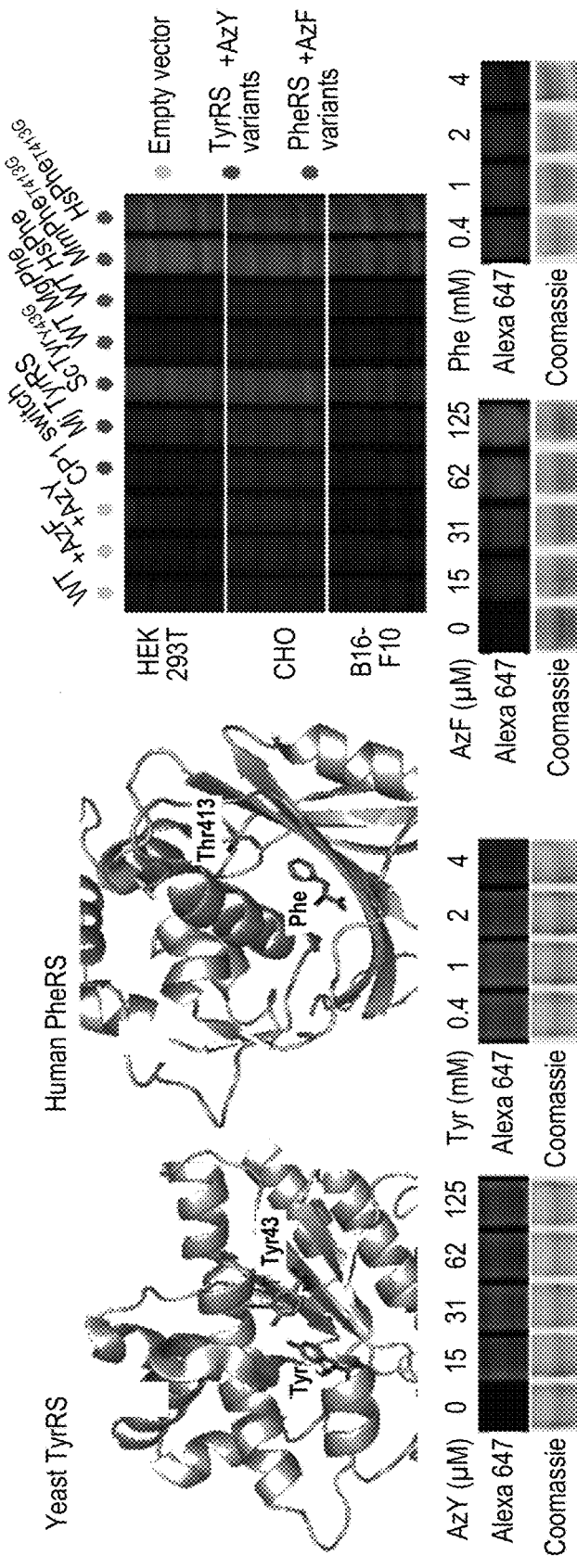

FIG. 3A
FIG. 3B
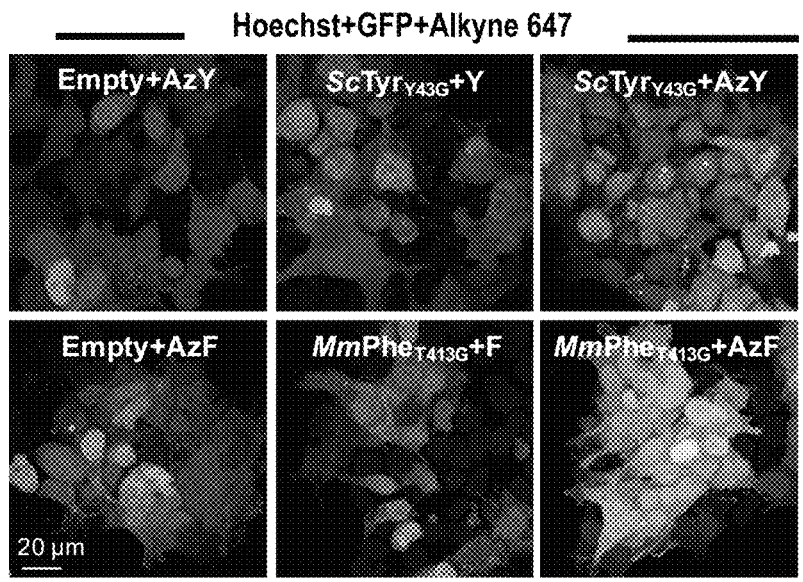
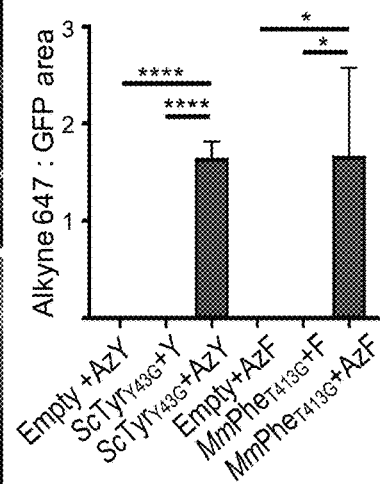
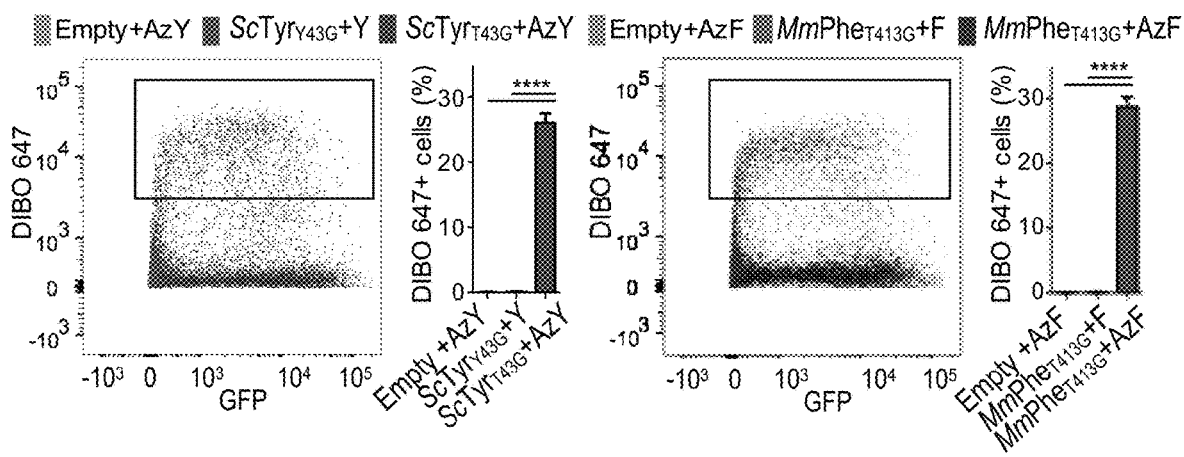
FIG. 3C
FIG. 3D

FIG. 4A
FIG. 4C
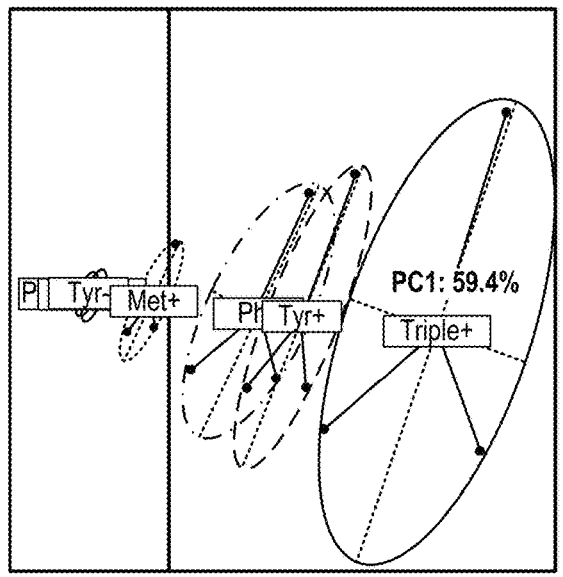
FIG. 4B
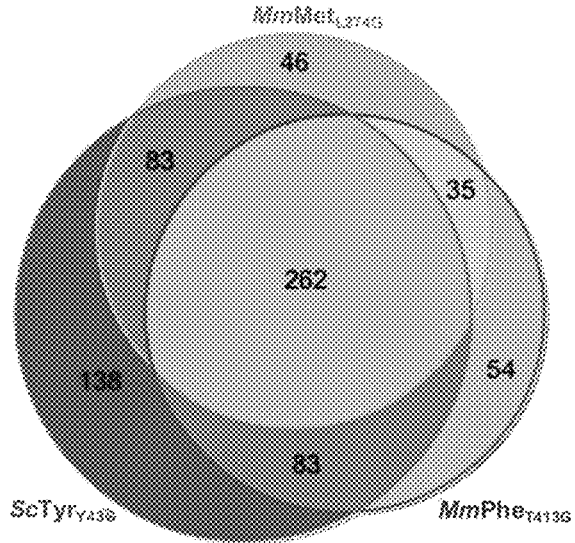
FIG. 4D
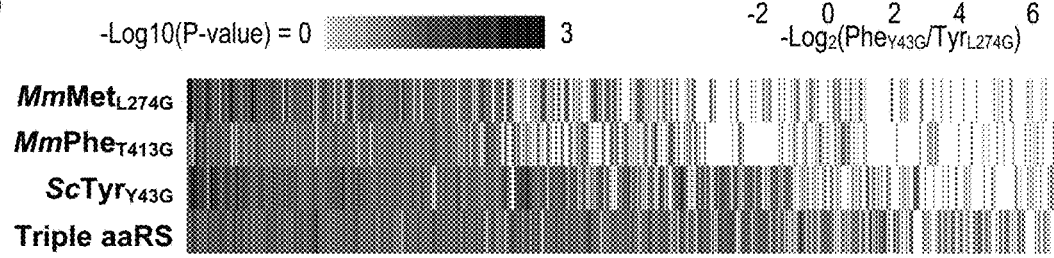

*FIG. 5A*
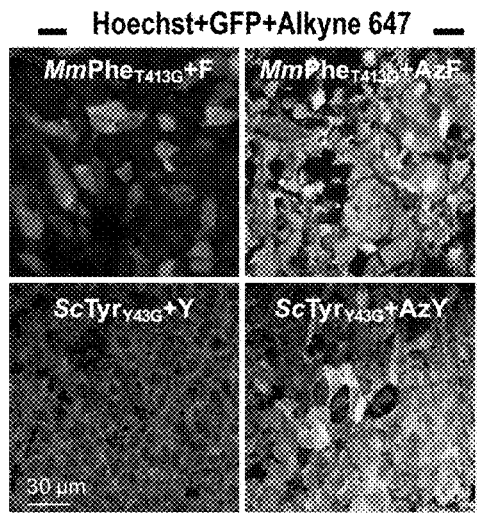
*FIG. 5B*
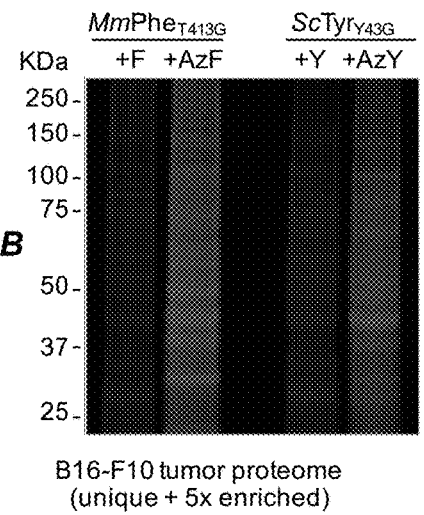
*FIG. 5C*
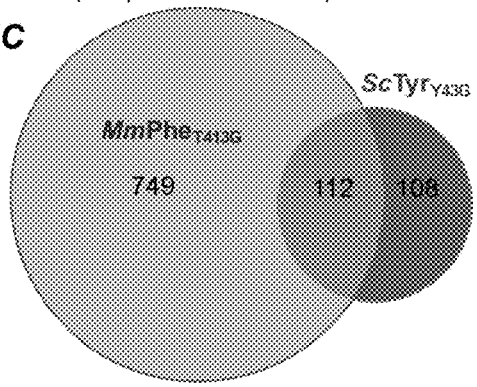
B16-F10 tumor proteome (unique + 5x enriched)
*FIG. 5D*
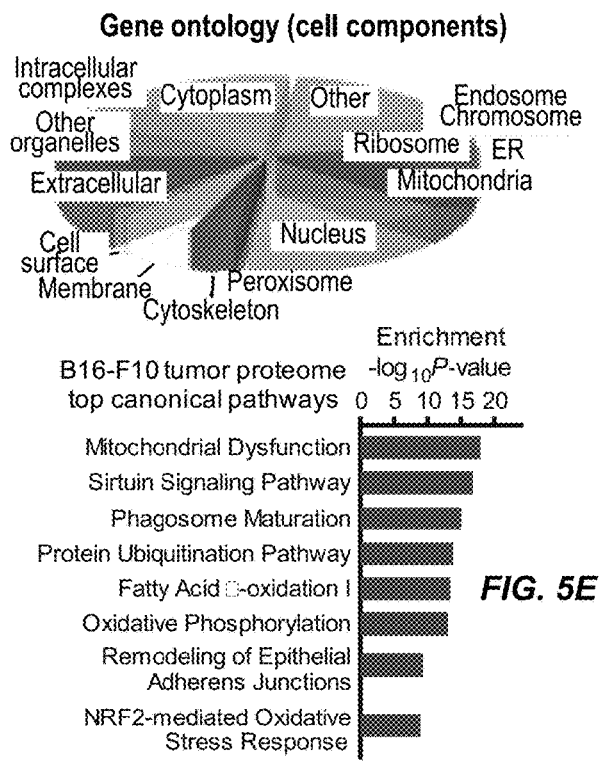
Gene ontology (cell components)
*FIG. 5E*
B16-F10 tumor proteome top canonical pathways
*FIG. 5F*
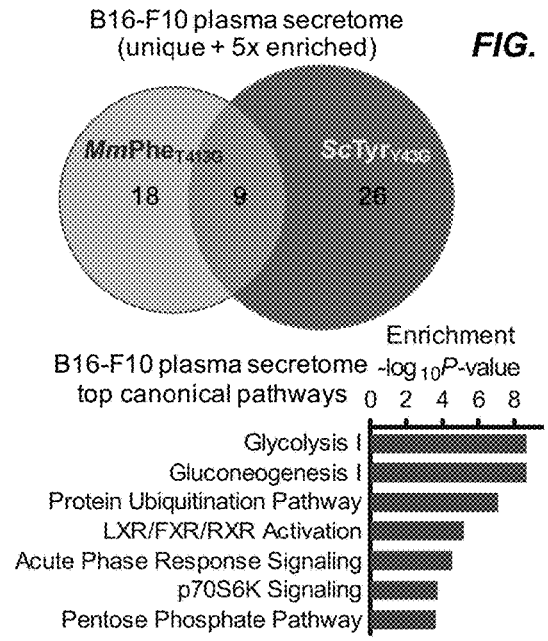
B16-F10 plasma secretome (unique + 5x enriched)
*FIG. 5G*
B16-F10 plasma secretome top canonical pathways

FIG. 15
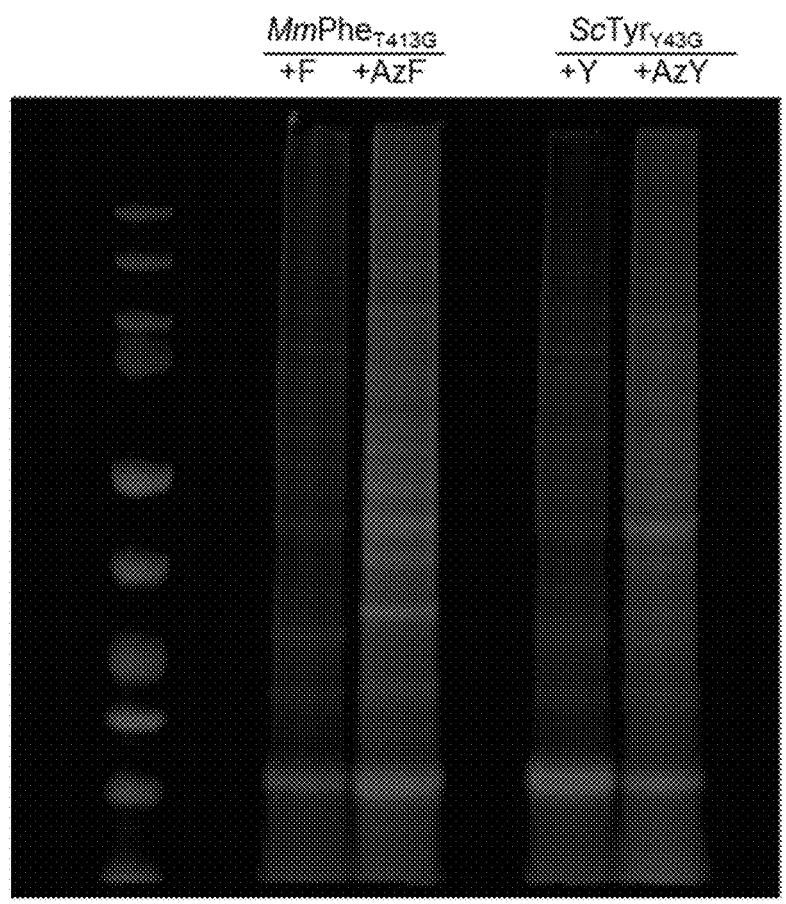
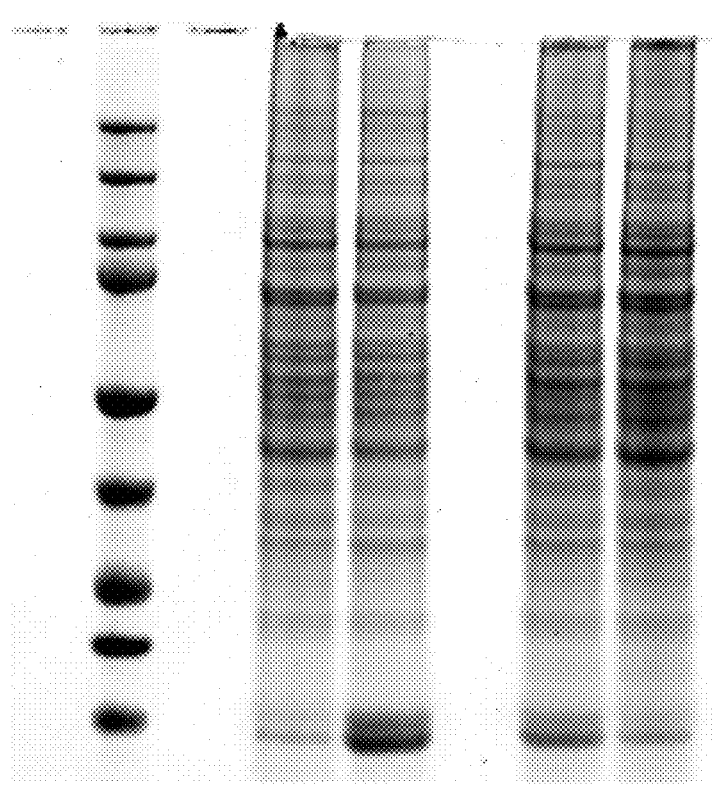

FIG. 17
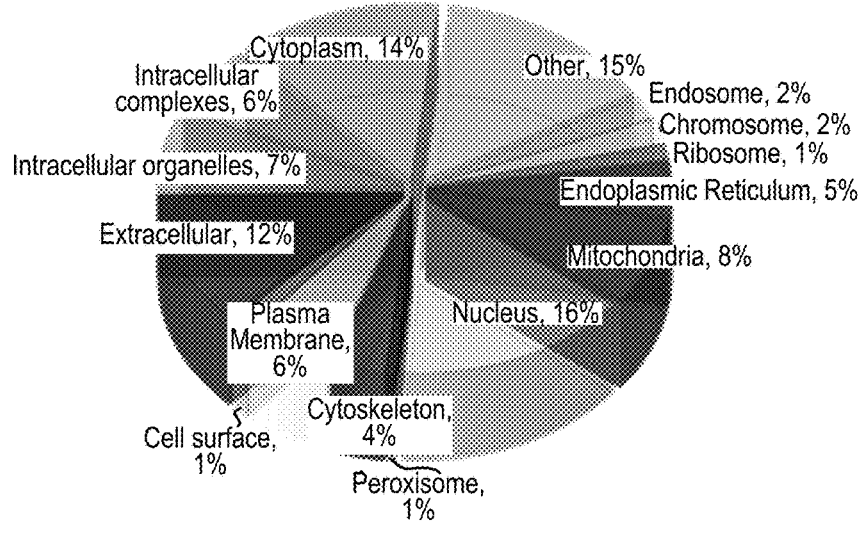
Combined MmPhe$_{T413G}$ and ScTyr$_{Y43G}$ B16-F10 melanoma proteome
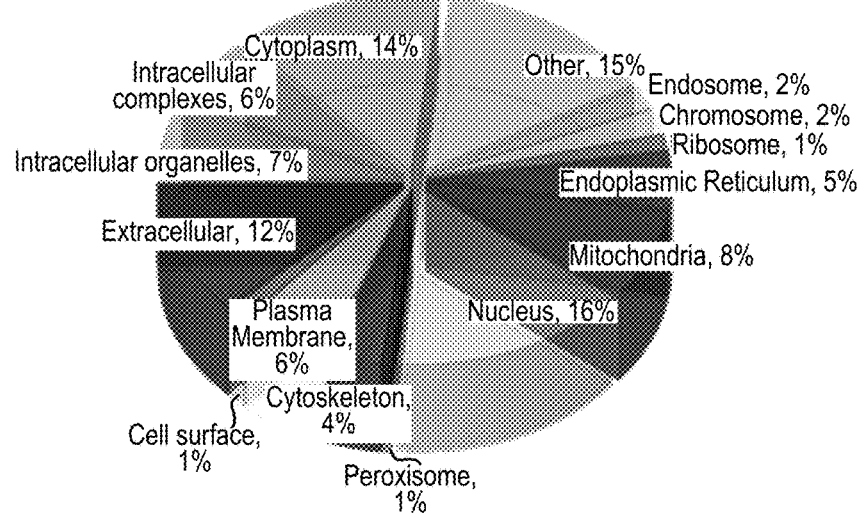
MmPhe$_{T413G}$ B16-F10 melanoma proteome
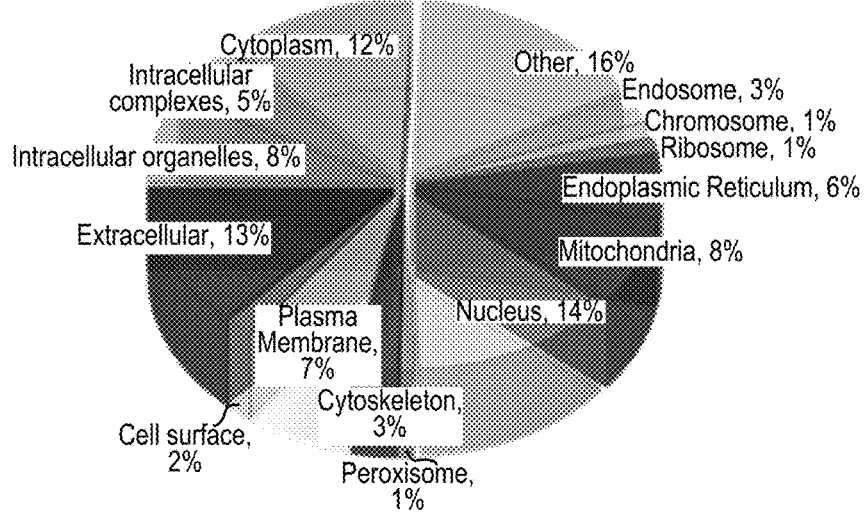
ScTyr$_{Y43G}$ B16-F10 melanoma proteome

*Mm*Phe<sub>T413G</sub> B16-F10 plasma secretome

ScTyr$_{Y43G}$ B16-F10 plasma secretome

FIG. 21
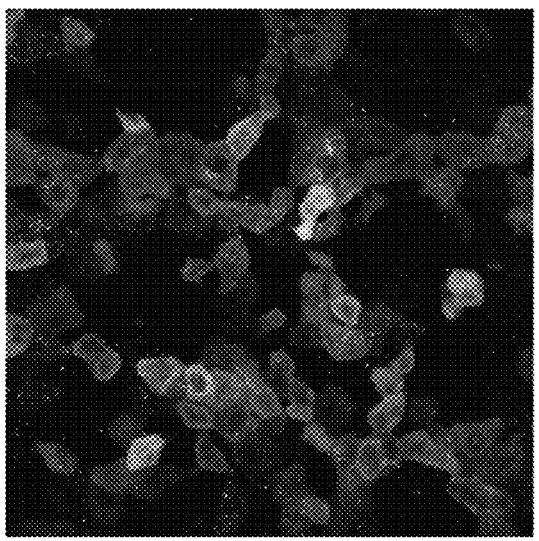
Liver (FLAG tag, white)
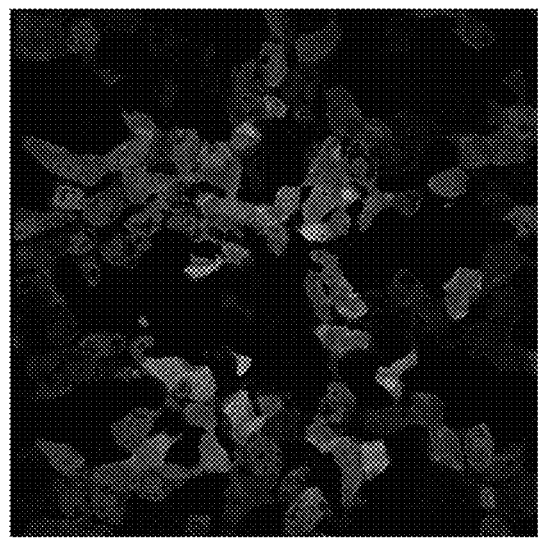
Liver (AzY, white)

FIG. 22
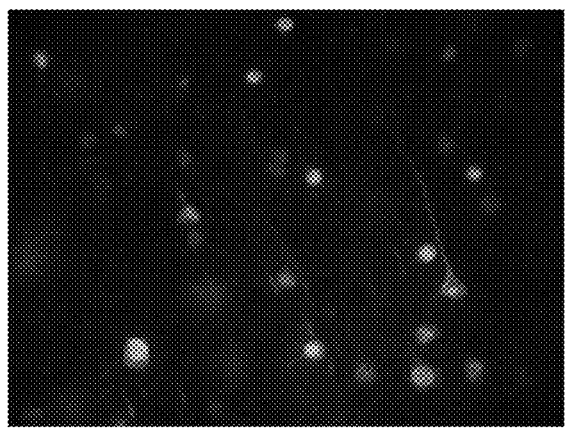
Cortex (AzY, white)
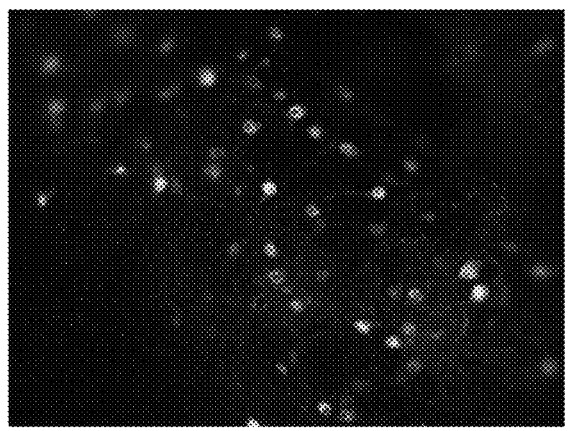
Pons (AzY, white)

METHODS FOR PROTEOME LABELING

CROSS-REFERENCE TO RELATED APPLICATIONS

This application is a continuation of International Application No. PCT/US2019/031587, filed May 9, 2019, which claims priority to U.S. Provisional Application No. 62/669,907, filed May 10, 2018, the disclosures of which are hereby incorporated by reference in their entirety for all purposes.

STATEMENT AS TO RIGHTS TO INVENTIONS MADE UNDER FEDERALLY SPONSORED RESEARCH AND DEVELOPMENT

This invention was made with Government support under contract AG053015 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Nov. 5, 2020, is named 2020-11-05_079445-1218109-001810US_SL.txt and is 35,358 bytes in size.

BACKGROUND OF THE INVENTION

Organisms and tissues are composed of heterogeneous cell types. Robust and comprehensive cell-type-specific proteomics are foundational to understanding the biological processes underlying health and disease. For example, cell-secreted signaling proteins in blood have been shown to not only correlate with, but modulate organismal and brain aging. Current efforts to characterize cell-type-specific proteomes and secretomes rely on various cell isolation techniques before acute analysis or primary cell culture; however, these techniques likely perturb the in vivo proteome, completely lose the secretome, and lack temporal resolution. Accordingly, there is a need in the art for improved tools and methods to facilitate the labeling of proteomes and, in particular, enable cell-type-specific and temporal labeling of cell secretomes. The present invention addresses this need, and provides related advantages as well.

BRIEF SUMMARY OF THE INVENTION

In one aspect, the present invention provides a method for labeling the proteome of a cell or a portion of the proteome of a cell. In some embodiments, the method comprises: (a) introducing into the cell one or more variant aminoacyl-tRNA synthetases that recognize one or more noncanonical amino acids; (b) introducing one or more noncanonical amino acids into the cell; (c) exposing the cell to conditions such that the one or more variant aminoacyl-tRNA synthetases activate one or more tRNAs in the cell with the one or more noncanonical amino acids, thereby producing one or more noncanonical activated tRNAs, and the one or more noncanonical amino acids are integrated into the proteome by the one or more noncanonical activated tRNAs, thereby producing a modified proteome; and (d) contacting the modified proteome with a detectable moiety, thereby producing a labeled proteome. In some embodiments, the proteome or portion thereof comprises the secretome of the cell or a portion thereof.

In another aspect, the present invention provides a method for labeling a protein or a population of proteins produced by a cell. In some embodiments, the method comprises: (a) introducing into the cell one or more variant aminoacyl-tRNA synthetases that recognize one or more noncanonical amino acids; (b) introducing one or more noncanonical amino acids into the cell; (c) exposing the cell to conditions such that the one or more variant aminoacyl-tRNA synthetases activate one or more tRNAs in the cell with the one or more noncanonical amino acids, thereby producing one or more noncanonical activated tRNAs, and the one or more noncanonical amino acids are integrated into the protein or population of proteins by the one or more noncanonical activated tRNAs, thereby producing a modified protein or a population of modified proteins; and (d) contacting the modified protein or population of modified proteins with a detectable moiety, thereby producing a labeled protein or a population of labeled proteins. In some embodiments, the protein or population of proteins produced by the cell is secreted by the cell.

In some embodiments, at least one of the one or more variant aminoacyl-tRNA synthetases comprise an amino acid substitution in an amino acid binding pocket compared to a corresponding wild-type aminoacyl-tRNA synthetase. In some embodiments, the amino acid substitution replaces a wild-type amino acid with a glycine. In some embodiments, the one or more variant aminoacyl-tRNA synthetases are selected from the group consisting of ScTyr$_{Y43G}$, MmPhe$_{T413G}$, HsPhe$_{T413G}$, MmMet$_{L274G}$, pyrrolysyl-tRNA synthetase, and a combination thereof.

In some embodiments, the one or more variant aminoacyl-tRNA synthetases are encoded by a polynucleotide that is codon-optimized to increase expression of the one of more variant aminoacyl-tRNA synthetases.

In some embodiments, the one or more noncanonical amino acids comprise an azide, an alkyne, a tetrazine, or a combination thereof. In some embodiments, the one or more noncanonical amino acids comprise an aryl azide. In some embodiments, the one or more noncanonical amino acids comprising an aryl azide are selected from the group consisting of p-azido-L-phenylalanine (AzF), 3-azido-L-tyrosine (AzY), and a combination thereof.

In another aspect, the present invention provides a labeled protein or a population of labeled proteins, wherein the protein or population of proteins are labeled by a method disclosed herein.

In yet another aspect, the present invention provides an isolated polynucleotide encoding a variant aminoacyl-tRNA synthetase that recognizes a noncanonical amino acid. In some embodiments, the isolated polynucleotide comprises a nucleic acid sequence having at least about 80% identity to any one of SEQ ID NOS:1-3. In some embodiments, the isolated polynucleotide comprises the nucleic acid sequence of any one of SEQ ID NOS:1-3. In some embodiments, the nucleic acid sequence is codon-optimized to increase expression of the variant aminoacyl-tRNA synthetase.

In some embodiments, the encoded variant aminoacyl-tRNA synthetase comprises an amino acid sequence having at least about 80% identity to any one of SEQ ID NOS:4-6. In some embodiments, the encoded variant aminoacyl-tRNA synthetase comprises the amino acid sequence of any one of SEQ ID NOS:4-6.

In another aspect, the present invention provides a cell that comprises a polynucleotide disclosed herein. In some embodiments, the cell further comprises one or more noncanonical amino acids. In some embodiments, the one or more noncanonical amino acids comprise an azide, an alkyne, a tetrazine, or a combination thereof. In some embodiments, the one or more noncanonical amino acids comprise an aryl azide. In some embodiments, the one or more noncanonical amino acids comprising an aryl azide are selected from the group consisting of p-azido-L-phenylalanine (AzF), 3-azido-L-tyrosine (AzY), and a combination thereof. In some embodiments, the cell further comprises a detectable moiety.

In another aspect, the present invention provides a kit for labeling the proteome of a cell or for labeling a protein or a population of proteins produced by a cell. In some embodiments, the kit comprises a polynucleotide disclosed herein and/or a cell disclosed herein.

In still another aspect, the present invention provides a method for identifying a target cell. In some embodiments, the method comprises: (a) labeling the proteome of the target cell or labeling a protein or a population of proteins produced by the target cell according to a method disclosed herein; (b) labeling the proteome of a reference cell or labeling a protein or a population of proteins produced by a reference cell according to a method disclosed herein; (c) detecting the labeled proteome, labeled protein, or population of labeled proteins in the target cell and reference cell to generate a target cell signature and a reference cell signature, respectively; (d) comparing the target cell signature to the reference cell signature; and (e) identifying the target cell based on the comparison in step (d).

In another aspect, the present invention provides a method for identifying one or more biomarkers of interest in a target cell. In some embodiments, the method comprises: (a) labeling the proteome of the target cell or labeling a protein or a population of proteins produced by the target cell according to a method disclosed herein; (b) labeling the proteome of a reference cell or labeling a protein or a population of proteins produced by a reference cell according to a method disclosed herein; (c) detecting the labeled proteome, labeled protein, or population of labeled proteins in the target cell and reference cell to generate a target cell signature and a reference cell signature, respectively; (d) comparing the target cell signature to the reference cell signature; and (e) identifying the one or more biomarkers of interest based on the comparison in step (d).

In some embodiments, the protein or population of proteins produced by the target cell and/or the reference cell are secreted by the target cell and/or the reference cell.

Other objects, features, and advantages of the present invention will be apparent to one of skill in the art from the following detailed description and figures.

BRIEF DESCRIPTION OF THE DRAWINGS

FIG. 1A: Engineered tRNA synthetases incorporate their azido amino acids preferentially across proteins of mammalian host cells. FIG. 1B: Incorporated azide side chains are chemoselectively reacted with alkyne derivatives for protein identification and imaging.

FIGS. 2A-2E: Identification and characterization of TyrRS and PheRS variants for bioorthogonal labeling of mammalian proteomes with AzY and AzF. FIG. 2A: A single substitution (Y43G) in the amino acid binding site of yeast tyrosyl-tRNA synthetase (ScTyr$_{Y43G}$) enables charging of the azido tyrosine analog AzY onto tRNA$^{Tyr}$ before incorporation into nascent proteins of host cells. FIG. 2B: A single substitution (T413G) in the amino binding site of human or mouse phenylalanyl-tRNA synthetase (MmPhe$_{T413G}$) enables charging of the azido phenylalanine analog AzF onto tRNA$^{Phe}$. FIG. 2C: In-gel fluorescence image of Alexa Fluor 647 labeling corresponding to AzY or AzF incorporation into mammalian cell proteomes. 'WT': no exogenous amino acid added to media. 'CP1 switch': an E. coli TyrRS with the human CP1 peptide engrafted. 'Mj TyRS': TyrRS from the species M. jannaschii, without its accompanying tRNA. FIG. 2D: High selectivity of ScTyr$_{Y43G}$ for AzY over Tyr. In-gel Alexa Fluor 647 fluorescence and coomassie blue staining of whole gel lanes were quantified to assess the degree of proteome labeling normalized to total protein content. The selectivity and rate were estimated from the line of best fit to standard Michaelis-Menten kinetics at increasing AzY concentrations with 0.4 mM Tyr, and validation via increasing Tyr concentrations with 15 μM AzY. Error bars indicate standard deviation. n=3 biological replicates. FIG. 2E: As in FIG. 2D, but for MmPhe$_{T413G}$, demonstrating high selectivity for AzF over Phe.

FIGS. 3A-3D: Fluorescence imaging and analysis of azide-labeled proteomes. Incorporation of the azide-bearing ncAA AzY or AzF into proteins by ScTyr$_{Y43G}$ and MmPhe$_{T413G}$ enables chemoselective conjugation to alkyne or DIBO-Alexa Fluor 647. Transfected HEK293T cells expressed mutant aaRS constructs or empty vector controls that co-expressed GFP, and were exposed to 125 μM AzY, AzF, tyrosine (Y), or phenylalanine (F). FIG. 3A: Imaging reveals proteome labeling specific to cells expressing the mutant aaRS and exposed to AzF or AzY. Proteome labeling is pervasive across each cell. FIG. 3B: Ratio of quantified Alexa Fluor 647 and GFP areas (n=3 images). FIGS. 3C and 3D: Flow cytometry of fixed HEK293T cells (after live/dead staining), with conditions as in imaging. Only cells with mutant aaRSs and exposed to ncAAs have DIBO-AF647$^+$ populations (n=3 biological replicates). Error bars indicate standard deviation. *P<0.05, ****P<0.0001.

FIGS. 4A-4D: Distinct proteomes labeled by each mutant aaRS. HEK293T cells transfected with equal total amounts of MmMet$_{L274G}$, ScTyr$_{Y43G}$, and MmPhe$_{T413G}$, or all three aaRSs were incubated with 125 μM of their corresponding azide-bearing ncAA or endogenous amino acids. Lysates were click-enriched on DBCO beads, washed, digested, and TMT labeled before mass spectrometry. n=3 biological replicates, in technical duplicate, for each condition. FIG. 4A: Each mutant aaRS differentially labels the HEK293T proteome, as spatially represented by PCA. FIG. 4B: Each mutant aaRS labels and identifies its own unique set of cell proteins. Most labeled proteins (66%, 463 of 701) are commonly detected across singly-expressed mutant aaRSs, increasing confidence in their identification. FIG. 4C: Among the 463 proteins identified by at least 2 aaRSs, each mutant aaRS exhibits different labeling efficiencies for different proteins. FIG. 4D: The co-expression of multiple mutant aaRSs ('Triple aaRS') enhances proteome coverage and detects more proteins with greater confidence, as assessed by P-value. Proteins significantly identified by at least one mutant aaRS were ordered by average $-\log_{10}$(P-value).

FIGS. 5A-5G: Cell-type-specific proteome and secretome labeling in vivo. B16-F10 mouse melanoma cells stably expressing ScTyr$_{Y43G}$ or MmPhe$_{T413G}$ alongside GFP were implanted subcutaneously in wild-type mice, and exposed to saturating amounts of AzF, AzY, Phe, or Tyr amino acids. n=3 mice except ScTyr$_{Y43G}$+Y and MmPhe$_{T413G}$+F, n=2 mice. FIG. 5A: In situ fluorescence confocal microscopy reveals AF647$^+$ proteome labeling in GFP$^+$ melanoma cells. Alkyne AF647 reacts chemoselectively to proteome-incorporated AzF and AzY. FIG. 5B: Proteome-wide labeling detected via in-gel fluorescence of tumor lysates. FIG. 5C: ScTyr$_{Y43G}$ and MmPhe$_{T413G}$ label distinct melanoma proteomes. Lysates were click-enriched on DBCO beads, washed, and digested into peptides for label-free mass spectrometry. Labeled proteomes were comprised of proteins unique to or over fivefold more abundant than in Phe- or Tyr-exposed tumors. FIG. 5D: Annotation of the labeled melanoma proteome by cellular component (STRAP), ScTyr$_{Y43G}$ and MmPhe$_{T413G}$ proteomes combined. FIG. 5E: Ingenuity Pathway Analysis. Top pathways enriched in the melanoma proteome, ScTyr$_{Y43G}$ and MmPhe$_{T413G}$ combined. Multiple pathways are implicated in tumor biology. FIG. 5F: ScTyr$_{Y43G}$ and MmPhe$_{T413G}$ label distinct melanoma plasma secretomes. FIG. 5G: Pathway analysis as in FIG. 5E but for the melanoma plasma secretome. Each mutant aaRS labels a distinct B16-F10 tumor proteome in vivo.

FIG. 15: Full-length gel for FIG. 5B. Representative in-gel fluorescence of B16-F10 tumor lysates demonstrates proteome-wide incorporation of AzF and AzY by stably integrated MmPhe$_{T413G}$ and zScTy$_{Y43G}$.

FIG. 17: STRAP Gene ontology annotation by cellular components of MmPhe$_{T413G}$ and ScTyr$_{Y43G}$ labeled in vivo melanoma proteomes in FIG. 5C.

FIGS. 5E and 5G show enriched pathways with identifications from the two aaRSs combined.

FIG. 19A shows MmPhe$_{T413G}$ B16-F10 melanoma proteome, and FIG. 19B shows ScTyr$_{Y43G}$ B16-F10 melanoma proteome.

FIG. 20A shows MmPhe$_{T413G}$ B16-F10 plasma secretome, and FIG. 20B shows ScTyr$_{Y43G}$ B16-F10 plasma secretome.

FIG. 21: Labeled hepatocytes. Mice were tail vein injected with AAV-DJ Ef-1a-FLAG-ScTyr$_{Y43G}$ and labeled with AzY. 40 µM liver sections were stained with anti-FLAG antibody (left) after attaching Alexa Fluor® 647 alkyne (right, ThermoFisher Scientific) to labeled proteins using copper click chemistry and imaged with a 40× objective.

FIG. 22: Labeled Neurons. Mice were retro-orbitally injected with AAV PHP.eB hSyn-FLAG-ScTyr$_{Y43G}$ and labeled with AzY. 40 μM brain sections were stained AzY protein labeling in neurons attaching Alexa Fluor® 647 alkyne (white, ThermoFisher Scientific) using copper click chemistry. Slices were imaged in the cortex (left) and pons (right) using a 40× objective.

DETAILED DESCRIPTION OF THE INVENTION

I. Introduction

Figure 1A:
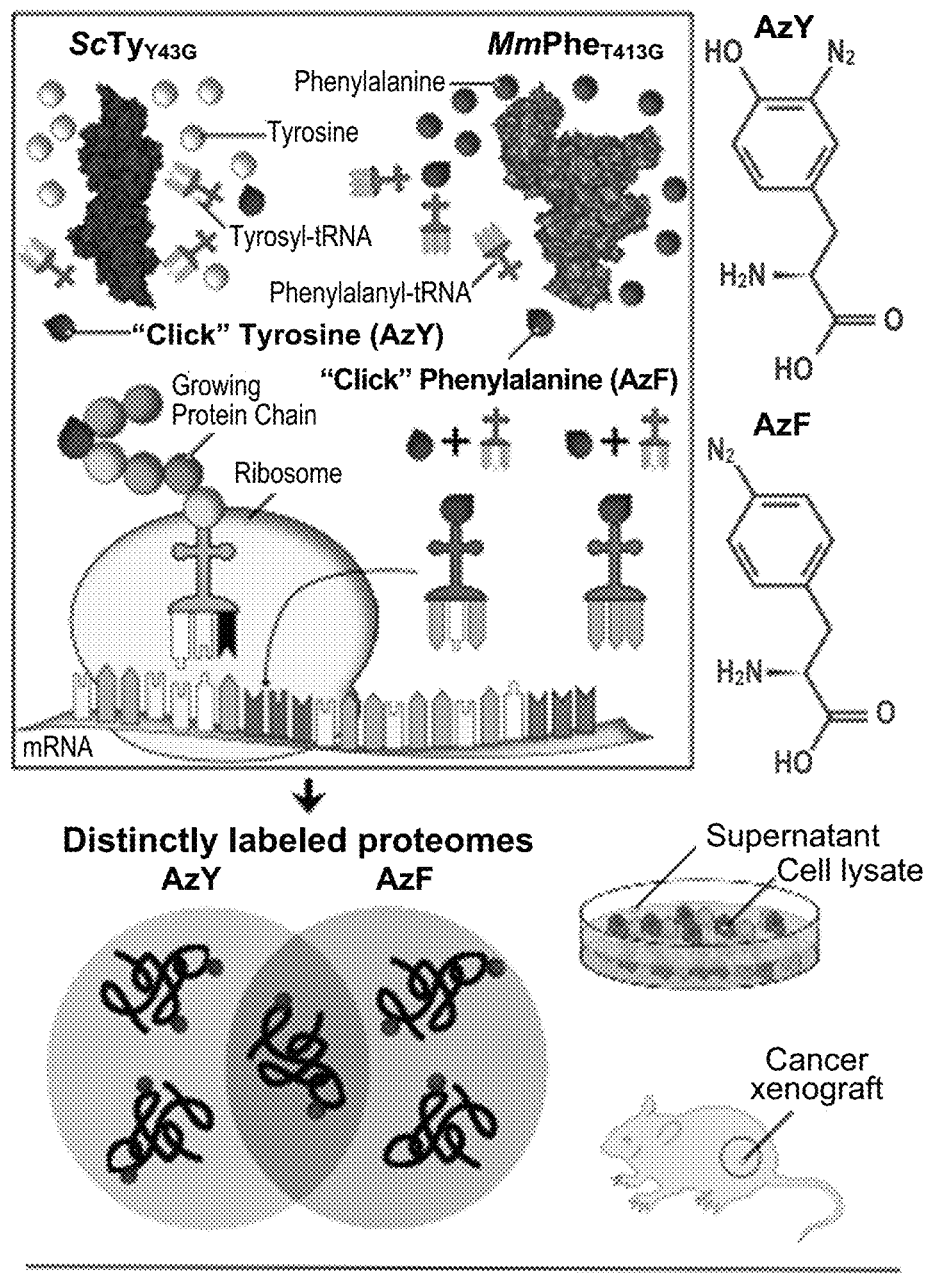
FIGS. 1A and 1B: Integrating identifications across mutant tRNA synthetases yields more complete and confident proteomics.

The labeling of proteins produced by target cells with bioorthogonal moieties occurs via the metabolic incorporation of noncanonical amino acids (ncAAs) that contain, for example, azide, alkyne, or other bioorthogonal side chains. This is accomplished by utilizing mutant aminoacyl-tRNA synthetases (aaRS) that recognize ncAAs that are ignored by endogenous aaRSs. By expressing aaRSs under the control of cell-type-specific promoters or inducible genetic tools, one can achieve cell-type- and temporally-restricted metabolic protein labeling in vivo.

The recent development of the L274G mouse methionyl-tRNA synthetase (MmMet$_{L274G}$), and its rapid adoption in multicellular organisms has enabled the characterization of specific neuronal proteomes. However, MmMet$_{L274G}$ is currently the only mutant aaRS available for mammalian cell-type-specific proteomics and is limited to charging its single cognate tRNA$^{Met}$ (ATG) with the methionine surrogate azidonorleucine. As a result, reliance on MmMet$_{L274G}$ potentially constricts proteome coverage and skews subsequent analysis. Furthermore, mutant aaRSs likely label many proteins differentially, each preferring a subset of the whole proteome.

The present invention is based, in part, on the identification of mutant aaRSs that enable more robust and broader mammalian cell-type-specific proteome labeling and proteomic studies. As described herein, the present invention is particularly advantageous in that endogenous tRNAs can be utilized, thereby removing the need for strong co-expression of exogenous tRNAs. Furthermore, the present invention allows the use of non-methionine codons, as well as multiple cognate codons, for the incorporation of noncanonical amino acids. Also advantageous is that noncanonical amino acid incorporation according to methods of the present invention does not require the depletion of canonical amino acids. Moreover, the present invention enables the delivery of mutant aaRSs to tissues such as the liver and brain to label proteins in vivo and detect tissue-derived, tagged proteins in samples such as blood.

II. Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The term "about" in relation to a reference numerical value can include a range of values plus or minus 10% from that value. For example, the amount "about 10" includes amounts from 9 to 11, including the reference numbers of 9, 10, and 11. The term "about" in relation to a reference numerical value can also include a range of values plus or minus 10%, 9%, 8%, 7%, 6%, 5%, 4%, 3%, 2%, or 1% from that value.

The term "aminoacyl-tRNA synthetase" or "aaRS" refers to an enzyme that attaches an amino acid to its designated tRNA, which can be referred to as "activating" or "charging" the tRNA. Attachment is accomplished by the enzyme catalyzing the esterification of a cognate amino acid (or a precursor thereof) to one of its compatible tRNAs, thereby producing an aminoacyl-tRNA. Aminoacyl-tRNA synthetases are divided into Class I and Class II enzymes. Class I aminoacyl-tRNA synthetases aminoacylate at the 2'-OH of a terminal adenosine nucleotide of a tRNA, whereas class II aminoacyl-tRNA synthetases aminoacylate at a 3'-OH of a terminal adenosine nucleotide.

The term "nucleic acid," "nucleotide," or "polynucleotide" refers to deoxyribonucleic acids (DNA), ribonucleic acids (RNA) and polymers thereof in either single-, double- or multi-stranded form. The term includes, but is not limited to, single-, double- or multi-stranded DNA or RNA, genomic DNA, cDNA, DNA-RNA hybrids, or a polymer comprising purine and/or pyrimidine bases or other natural, chemically modified, biochemically modified, non-natural, synthetic or derivatized nucleotide bases. In some embodiments, a nucleic acid can comprise a mixture of DNA, RNA and analogs thereof. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)).

The terms "polypeptide," "peptide," and "protein" are used interchangeably herein to refer to a polymer of amino acid residues, or an assembly of multiple polymers of amino acid residues.

The term "amino acid" includes but is not limited to naturally-occurring α-amino acids and their stereoisomers. "Stereoisomers" of amino acids refers to mirror image isomers of the amino acids, such as L-amino acids or D-amino acids. For example, a stereoisomer of a naturally-occurring amino acid refers to the mirror image isomer of the naturally-occurring amino acid (i.e., the D-amino acid).

Naturally-occurring or amino acids are those encoded by the genetic code, as well as those amino acids that are later modified (e.g., hydroxyproline, γ-carboxyglutamate, and O-phosphoserine). Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

The term "canonical amino acid" refers to any of the 20 amino acids that are encoded by the triplet codons of the genetic code. These include (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr).

The term "noncanonical amino acid" refers to any amino acid that is not a canonical amino acid (i.e., an amino acid that is not encoded by the triplet codons of the genetic code). In some embodiments, a noncanonical amino acid is a modified version of a canonical amino acid. As a non-limiting example, the noncanonical amino acids p-azido-L-phenylalanine (AzF), 3-azido-L-tyrosine (AzY) are modified versions of the canonical amino acids Phe and Tyr, respectively, to which an azide group has been added to the aryl moiety of the amino acid side chain. In addition to azide groups, non-canonical amino acids can comprise, as non-limiting examples, alkyne groups or tetrazine groups. The inclusion of azide, alkyne, and tetrazine groups facilitates the labeling (e.g., tagging or attaching) with a moiety such as a fluorophore (e.g., for imaging) or an affinity resin (e.g., for mass spectrometric characterization).

Amino acids may be referred to herein by either their commonly known three letter symbols or by the one-letter symbols recommended by the IUPAC-IUB Biochemical Nomenclature Commission. For example, an L-amino acid may be represented herein by its commonly known three letter symbol (e.g., Arg for L-arginine) or by an upper-case one-letter amino acid symbol (e.g., R for L-arginine). A D-amino acid may be represented herein by its commonly known three letter symbol (e.g., D-Arg for D-arginine) or by a lower-case one-letter amino acid symbol (e.g., r for D-arginine).

The term "aryl" refers to an aromatic ring system having any suitable number of ring atoms and any suitable number of rings. Aryl groups can include any suitable number of ring atoms, such as, 6, 7, 8, 9, 10, 11, 12, 13, 14, 15, or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted. Aryl groups can be optionally substituted with one or more moieties selected from alkyl, alkenyl, alkynyl, halo, hydroxy, amino, azido (i.e., an aryl azide), thiol, alkylamino, alkoxy, haloalkyl, carboxy, amido, nitro, oxo, thioxo, and cyano.

The term "azide" refers to an anion with the formula $N_3^-$.

The term "alkyne" refers to an unsaturated hydrocarbon that contains at least one carbon-carbon triple bond.

The term "tetrazine" refers to a compound, typically unstable, that contains a six-membered aromatic ring comprising four nitrogen atoms. Tetrazines have the molecular formula $C_2H_2N_4$. Tetrazine core-ring isomers include 1,2,3,4-tetrazines, 1,2,3,5-tetrazines, and 1,2,4,5-tetrazines.

The terms "subject," "individual," and "patient" are used interchangeably herein to refer to a vertebrate, preferably a mammal, more preferably a human. Mammals include, but are not limited to, rodents (e.g., mice, rats), simians, humans, farm animals, sport animals, and pets. Tissues, cells and their progeny of a biological entity obtained in vivo or cultured in vitro are also encompassed.

The term "codon optimization" refers to altering a nucleic acid sequence, without changing the encoded amino acid sequence, in such a way that codon bias (i.e., the preferential use of particular codons that can vary between species) is reduced or rebalanced. In some embodiments, codon optimization increases translational efficiency (e.g., of a variant aminoacyl-tRNA synthetase, such as one that recognizes a noncanonical amino acid). As a non-limiting example, leucine is encoded by six different codons, some of which are rarely used. By rebalancing codon usage (e.g., within a reading frame), preferred leucine codons can be selected over rarely used codons. The nucleic acid sequence encoding the protein (e.g., variant aminoacyl-tRNA synthetase) of interest is altered such that the rarely used codons are converted to preferred codons.

Rare codons can be defined, for example, by using a codon usage table derived from the sequenced genome of a host species (i.e., the species in which the protein (e.g., a variant aminoacyl-tRNA synthetase) will be expressed). See, e.g., the codon usage table obtained from Kazusa DNA Research Institute, Japan (www.kazusa.or.jp/codon/) used in conjunction with software, e.g., "Gene Designer 2.0" software, from DNA 2.0 (www.dna20.com/) at a cut-off threshold of 15%.

Codon optimization may also be employed to modulate GC content, e.g., to increase mRNA stability or reduce secondary structure; or otherwise minimize codons that may result in stretches of sequence that impair expression of the protein of interest (e.g., a variant aminoacyl-tRNA synthetase, such as one that recognizes a noncanonical amino acid).

"Percent similarity," in the context of polynucleotide or peptide sequences, is determined by comparing two optimally aligned sequences over a comparison window, wherein the portion of the sequence of interest in the comparison window may comprise additions or deletions (i.e., gaps) as compared to the reference sequence which does not comprise additions or deletions, for optimal alignment of the two sequences. The percentage is calculated by determining the number of positions at which the identical nucleotide or amino acid occurs in both sequences to yield the number of matched positions, dividing the number of matched positions by the total number of positions in the window of comparison and multiplying the result by 100 to yield the percentage of similarity (e.g., sequence similarity).

When a polynucleotide or peptide has at least about 70% similarity (e.g., sequence similarity), preferably at least about 85%, 86%, 87%, 88%, 89%, 90%, 91%, 92%, 93, 94%, 95%, 96%, 97%, 98%, 99%, or 100% similarity, to a reference sequence, when compared and aligned for maximum correspondence over a comparison window, or designated region as measured using one of the following sequence comparison algorithms or by manual alignment and visual inspection, such sequences are then said to be "substantially similar." With regard to polynucleotide sequences, this definition also refers to the complement of a test sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence similarities for the test sequences relative to the reference sequence, based on the program parameters. For sequence comparison of nucleic acids and proteins, the BLAST and BLAST 2.0 algorithms and the default parameters discussed below are used.

Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Additional examples of algorithms that are suitable for determining percent sequence similarity are the BLAST and BLAST 2.0 algorithms, which are described in Altschul et al., (1990) *J. Mol. Biol.* 215: 403-410 and Altschul et al. (1977) *Nucleic Acids Res.* 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see, e.g., Henikoff and Henikoff, *Proc. Natl. Acad. Sci. USA* 89:10915 (1989)).

The BLAST algorithm also performs a statistical analysis of the similarity between two sequences (see, e.g., Karlin and Altschul, *Proc. Nat'l. Acad. Sci. USA,* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "cancer" refers to any of various malignant neoplasms characterized by the proliferation of anaplastic cells that tend to invade surrounding tissue and metastasize to new body sites. Non-limiting examples of different types of cancer suitable for identification and study according to methods and compositions of the present invention include skin cancer (e.g., melanoma), colorectal cancer, colon cancer, anal cancer, liver cancer, ovarian cancer, breast cancer, lung cancer, bladder cancer, thyroid cancer, pleural cancer, pancreatic cancer, cervical cancer, prostate cancer, testicular cancer, bile duct cancer, gastrointestinal carcinoid tumors, esophageal cancer, gall bladder cancer, rectal cancer, appendix cancer, small intestine cancer, stomach (gastric) cancer, renal cancer (i.e., renal cell carcinoma), cancer of the central nervous system, oral squamous cell carcinoma, choriocarcinomas, head and neck cancers, bone cancer, osteogenic sarcomas, fibrosarcoma, neuroblastoma, glioma, melanoma, leukemia (e.g., acute lymphocytic leukemia, chronic lymphocytic leukemia, acute myelogenous leukemia, chronic myelogenous leukemia, or hairy cell leukemia), lymphoma (e.g., non-Hodgkin's lymphoma, Hodgkin's lymphoma, B-cell lymphoma, or Burkitt's lymphoma), and multiple myeloma. The cancer can be any stage (e.g., advanced cancer or metastatic cancer).

The term "neurological disease" refers to any disease or pathological condition that is associated with a reduction or loss of normal function in the central nervous system (e.g., the brain, spinal cord) and/or the peripheral nervous system. Diseases that are associated with neuromuscular impairment are also included. Non-limiting examples of neurological diseases include adrenal leukodystrophy (ALD), alcoholism, Alexander's disease, Alper's disease, ataxia telangiectasia, Batten disease (also known as Spielmeyer-Vogt-SjcSgren-Batten disease), bovine spongiform encephalopathy (BSE), Canavan disease, cerebral palsy, Cockayne syndrome, corticobasal degeneration, Creutzfeldt-Jakob disease, familial fatal insomnia, frontotemporal lobar degeneration, HIV-associated dementia, Kennedy's disease, Krabbe's disease, Lewy body dementia, neuroborreliosis, Machado-Joseph disease (Spinocerebellar ataxia type 3), multiple system atrophy, narcolepsy, Niemann Pick disease, Pelizaeus-Merzbacher Disease, Pick's disease, primary lateral sclerosis, prion diseases, progressive supranuclear palsy, Refsum's disease, Sandhoff disease, Schilder's disease, subacute combined degeneration of spinal cord secondary to pernicious anemia, spinocerebellar ataxia, spinal muscular atrophy, Steele-Richardson-Olszewski disease, Tabes dorsalis, toxic encephalopathy, progressive external ophthalmoplegia (PEO), Leigh's Syndrome, MNGIE (Myopathy and external ophthalmoplegia; Neuropathy; Gastro-Intestinal; Encephalopathy), Kearns-Sayre Syndrome (KSS), hereditary spastic paraparesis, mitochondrial myopathy, Friedreich's ataxia; MELAS (mitochondrial encephalopathy, lactic acidosis, and stroke-like episodes), MERRF (myoclonic epilepsy with ragged red fibers), LHON (Leber's hereditary optic neuropathy) NARP (neuropathy, ataxia, and retinitis pigmentosa), MILS (maternally inherited Leigh syndrome), stroke, and a combination thereof.

In some embodiments, the neurological disease is a neurodegenerative disease. Non-limiting examples of neurodegenerative diseases include Alzheimer's disease, Parkinson's disease, Huntington's disease, amyotrophic lateral sclerosis (ALS), and multiple sclerosis (MS)), as well as conditions characterized by neurodegeneration and/or neuroinflammation, i.e., conditions in which either or both of those processes leads to a failure of a subject's nervous system to function normally.

The term "immune disease" refers to any disease that is associated with abnormal immune function. An immune disease can manifest as decreased immune function (e.g., immunodeficiency) or can manifest as an abnormal or pathological increase in immune function. In some instances, an immune disease manifests as an inflammatory disease (i.e., a disease characterized by abnormal or pathologically excessive inflammation, e.g., of a tissue, organ, or organ system). In some embodiments, the immune disease is an "autoimmune disease," i.e., a disease cause by the production and/or activity of antibodies or lymphocytes against "self" antigens in a subject. Non-limiting examples of autoimmune diseases include autoimmune nervous system diseases (e.g., multiple sclerosis (MS), myasthenia gravis, autoimmune neuropathies such as Guillian-Barre syndrome), autoimmune ophthalmologic diseases (e.g., uveitis), autoimmune blood disorders (e.g., autoimmune hemolytic anemia, pernicious anemia, autoimmune thrombocytopenia), autoimmune vascular diseases (e.g., temporal arteritis, anti-phospholipid syndrome, autoimmune vasculitis, Bechet's disease, atherosclerosis), autoimmune skin diseases (e.g., psoriasis, dermatitis herpetiformis, pemphigus vulgaris, vitiligo, mycosis fungoides, allergic contact dermatitis, atopic dermatitis, lichen planus, pityriasis lichenoides at varioliforms acute (PLEVA)), autoimmune gastrointestinal diseases (e.g., Crohn's disease, ulcerative colitis, primary biliary cirrhosis, autoimmune hepatitis), autoimmune endocrine disorders (e.g., type I diabetes mellitus, Addison's disease, Grave's disease, Hashimoto's thyroiditis), and combinations thereof.

III. Description of the Embodiments

A. Proteome and Protein Labeling

In one aspect, the present invention provides a method for labeling the proteome of a cell or a portion of the proteome of a cell. In some embodiments, the method comprises: (a) introducing into the cell one or more variant aminoacyl-tRNA synthetases that recognize one or more noncanonical amino acids; (b) introducing one or more noncanonical amino acids into the cell; (c) exposing the cell to conditions such that the one or more variant aminoacyl-tRNA synthetases activate one or more tRNAs in the cell with the one or more noncanonical amino acids, thereby producing one or more noncanonical activated tRNAs, and the one or more noncanonical amino acids are integrated into the proteome by the one or more noncanonical activated tRNAs, thereby producing a modified proteome; and (d) contacting the modified proteome with a detectable moiety, thereby producing a labeled proteome. In some embodiments, the proteome or portion thereof comprises the secretome of the cell or a portion thereof.

In another aspect, the present invention provides a method for labeling a protein or a population of proteins produced by a cell. In some embodiments, the method comprises: (a) introducing into the cell one or more variant aminoacyl-tRNA synthetases that recognize one or more noncanonical amino acids; (b) introducing one or more noncanonical amino acids into the cell; (c) exposing the cell to conditions such that the one or more variant aminoacyl-tRNA synthetases activate one or more tRNAs in the cell with the one or more noncanonical amino acids, thereby producing one or more noncanonical activated tRNAs, and the one or more noncanonical amino acids are integrated into the protein or population of proteins by the one or more noncanonical activated tRNAs, thereby producing a modified protein or a population of modified proteins; and (d) contacting the modified protein or population of modified proteins with a detectable moiety, thereby producing a labeled protein or a population of labeled proteins.

In some embodiments, the labeled protein or population of labeled proteins comprises the proteome of the cell. In some embodiments, the labeled protein or population of labeled proteins comprises a portion of the proteome of the cell. In some embodiments, the labeled protein or population of labeled proteins comprises the secretome of the cell. In some embodiments, the labeled protein or population of labeled proteins comprises a portion of the secretome of the cell. In some embodiments, the labeled protein or population of labeled proteins is secreted by the cell. In some embodiments, one or more isoforms or variants of a protein are labeled. In some embodiments, all isoforms or variants of a protein are labeled.

Variant aminoacyl-tRNA synthetases can be engineered or derived from any appropriate organism. Non-limiting examples include Escherichia coli, Methanococcus jannaschii, Methanosarcina barkeri, Methanosarcina mazei, Saccharomyces cerevisiae (Sc), Caenorhabditis elegans, Drosophila melanogaster, Danio rerio, Mus musculus (Mm), and Homo sapiens (Hs). Furthermore, variant pryyolysyl-tRNA synthetases can be used.

In some embodiments, the variant aminoacyl-tRNA synthetase comprises an amino acid substitution compared to a corresponding wild-type aminoacyl-tRNA synthetase. In some embodiments, the variant aminoacyl-tRNA synthetase comprises an amino acid substitution in an amino acid binding pocket compared to a corresponding wild-type aminoacyl-tRNA synthetase. In general, amino acid substitutions that allow for more room within the amino acid binding pocket (i.e., in order to better accomodate a larger noncanonical amino acid) are desired. In some embodiments, the amino acid substitution replaces a wild-type amino acid with a smaller amino acid. In some embodiments, the amino acid substitution replaces a wild-type amino acid with a glycine. In some embodiments, the encoded aminoacyl-tRNA synthetase comprises one or more (e.g., 1, 2, 3, 4, 5, or more) amino acid substitutions relative to the amino acid sequence set forth in SEQ ID NO:7, 8, or 9.

In some embodiments, the one or more (e.g., 1, 2, 3, 4, 5, or more) variant aminoacyl-tRNA synthetases are selected from the group consisting of $ScTyr_{Y43G}$, $MmPhe_{T413G}$, $HsPhe_{T413G}$, $MmMet_{L274G}$, pyrrolysyl-tRNA synthetase, and a combination thereof.

In some embodiments, the one or more variant aminoacyl-tRNA synthetases comprise $ScTyr_{Y43G}$ and $MmPhe_{T413G}$. In some embodiments, the one or more variant aminoacyl-tRNA synthetases comprise $ScTyr_{Y43G}$ and $HsPhe_{T413G}$. In some embodiments, the one or more variant aminoacyl-tRNA synthetases comprise $ScTyr_{Y43G}$ and $MmMet_{L274G}$. In some embodiments, the one or more variant aminoacyl-tRNA synthetases comprise $MmPhe_{T413G}$ and MmMet$_{L274G}$. In some embodiments, the one or more variant aminoacyl-tRNA synthetases comprise HsPhe$_{T413G}$ and MmMet$_{L274G}$. In some embodiments, the one or more variant aminoacyl-tRNA synthetases comprise MmPhe$_{T413G}$ and HsPhe$_{T413G}$.

In some embodiments, the one or more variant aminoacyl-tRNA synthetases comprise ScTyr$_{Y43G}$, MmPhe$_{T413G}$, and HsPhe$_{T413G}$. In some embodiments, the one or more variant aminoacyl-tRNA synthetases comprise ScTyr$_{Y43G}$, MmPhe$_{T413G}$, and MmMet$_{L274G}$. In some embodiments, the one or more variant aminoacyl-tRNA synthetases comprise ScTyr$_{Y43G}$, HsPhe$_{T413G}$, and MmMet$_{L274G}$. In some embodiments, the one or more variant aminoacyl-tRNA synthetases comprise MmPhe$_{T413G}$, HsPhe$_{T413G}$, and MmMet$_{L274G}$. In some embodiments, the one or more variant aminoacyl-tRNA synthetases comprise ScTyr$_{Y43G}$, MmPhe$_{T413G}$, HsPhe$_{T413G}$, and MmMet$_{L274G}$.

In some instances, it is advantageous to use multiple forms (e.g., both the mouse and human forms) of a variant aminoacyl-tRNA synthetase (e.g., MmPhe$_{T413G}$ and HsPhe$_{T413G}$). As a non-limiting example, a human cell, tissue, organoid, or organ can be transplanted into another species such as a mouse, and utilizing both the human and mouse forms of the variant aminoacyl-tRNA synthetase can enable proteomic studies of host-graft cross-talk. Furthermore, due to the large degree of homology between some aminoacyl-tRNA synthetases, one species-specific variant can be used, in some instances, to label proteomes, proteins, or populations of proteins in another species (e.g., a human variant can be used for labeling in mouse cells, and vice versa).

In some embodiments, the variant aminoacyl-tRNA synthetase comprises an amino acid sequence having at least about 70% identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOS:4-6. In some embodiments, the variant aminoacyl-tRNA synthetase comprises the amino acid sequence of any one of SEQ ID NOS:4-6.

In some embodiments, the variant aminoacyl-tRNA synthetase comprises an amino acid sequence having at least about 70% identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) to SEQ ID NO:4. In some embodiments, the variant aminoacyl-tRNA synthetase comprises the amino acid sequence set forth in SEQ ID NO:4.

In some embodiments, the variant aminoacyl-tRNA synthetase comprises an amino acid sequence having at least about 70% identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) to SEQ ID NO:5. In some embodiments, the variant aminoacyl-tRNA synthetase comprises the amino acid sequence set forth in SEQ ID NO:5.

In some embodiments, the variant aminoacyl-tRNA synthetase comprises an amino acid sequence having at least about 70% identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) to SEQ ID NO:6. In some embodiments, the variant aminoacyl-tRNA synthetase comprises the amino acid sequence set forth in SEQ ID NO:6.

In some embodiments, the one or more variant aminoacyl-tRNA synthetases are encoded by a nucleic acid sequence having at least about 70% identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOS:1-3. In some embodiments, the one or more variant aminoacyl-tRNA synthetases are encoded by the nucleic acid sequence set forth in any one of SEQ ID NOS:1-3.

In some embodiments, the one or more variant aminoacyl-tRNA synthetases are encoded by a nucleic acid sequence having at least about 70% identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) to SEQ ID NO:1. In some embodiments, the one or more variant aminoacyl-tRNA synthetases are encoded by the nucleic acid sequence set forth in SEQ ID NO:1.

In some embodiments, the one or more variant aminoacyl-tRNA synthetases are encoded by a nucleic acid sequence having at least about 70% identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) to SEQ ID NO:2. In some embodiments, the one or more variant aminoacyl-tRNA synthetases are encoded by the nucleic acid sequence set forth in SEQ ID NO:2.

In some embodiments, the one or more variant aminoacyl-tRNA synthetases are encoded by a nucleic acid sequence having at least about 70% identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) to SEQ ID NO:3. In some embodiments, the one or more variant aminoacyl-tRNA synthetases are encoded by the nucleic acid sequence set forth in SEQ ID NO:3.

In some embodiments, the one or more variant aminoacyl-tRNA synthetases are encoded by a polynucleotide (e.g., comprising a nucleic acid sequence) that is codon-optimized to increase expression of the one of more variant aminoacyl-tRNA synthetases.

In some embodiments, when a nucleic acid sequence (e.g., a nucleic acid sequence encoding a variant aminoacyl-tRNA synthetase) is codon-optimized, expression from the nucleic acid sequence (e.g., expression of the variant aminoacyl-tRNA synthetase) is increased by at least about 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, or more compared to expression from the corresponding non-codon-optimized nucleic acid sequence. In some embodiments, the nucleic acid sequence is codon-optimized to increase expression in a particular cell type or species of interest (e.g., expression in a mammalian cell such as a human, non-human primate, mouse, or rat cell).

In some embodiments, two or more (e.g., 2, 3, 4, 5, or more) different variant aminoacyl-tRNA synthetases that recognize noncanonical amino acids are used. In some embodiments, using two or more different variant aminoacyl-tRNA synthetases that recognize noncanonical amino acids increases the number of proteins that are labeled compared to when a single variant aminoacyl-tRNA synthetase that recognizes a noncanonical amino acid is used. In some embodiments, the number or proteins that are labeled when two or more variant aminoacyl-tRNA synthetases that recognize noncanonical amino acids are used is at least about 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 10.5-fold, 11-fold, 11.5-fold, 12-fold, 12.5-fold, 13-fold, 13.5-fold, 14-fold, 14.5-fold, 15-fold, 15.5-fold, 16-fold, 16.5-fold, 17-fold, 17.5-fold, 18-fold, 18.5-fold, 19-fold, 19.5-fold, 20-fold, 21-fold, 22-fold, 23-fold, 24-fold, 25-fold, 26-fold, 27-fold, 28-fold, 29-fold, 30-fold, 31-fold, 32-fold, 33-fold, 34-fold, 35-fold, 36-fold, 37-fold, 38-fold, 39-fold, or 40-fold higher compared to when only one variant aminoacyl-tRNA synthetase that recognizes a noncanonical amino acid is used.

In some embodiments, at least one of the one or more tRNAs in the cell recognize a methionine codon and/or a non-methionine codon. In some embodiments, at least one of the one or more tRNAs in the cell recognize more than one cognate codon. For example, in some embodiments, the one or more tRNAs recognize both the TAT and TAC codons for Tyr. As another example, in some embodiments, the one or more tRNAs recognize both the TTT and TTC codons for Phe.

In some embodiments, all of the tRNAs in the cell are endogenous. In some embodiments, some of the tRNAs are endogenous, and some of the tRNAs are exogenous (e.g., expressed from a polynucleotide that is introduced into the cell). When using exogenous tRNAs, they can be expressed from the same polynucleotide as that encoding the variant aminoacyl-tRNA synthetase, or can be expressed from a separate polynucleotide.

In some embodiments, the one or more noncanonical amino acids comprise an azide, an alkyne, a tetrazine, or a combination thereof. In some embodiments, the one or more noncanonical amino acids comprise an azide. In some embodiments, the one or more noncanonical amino acids comprise an alkyne. In some embodiments, the one or more noncanonical amino acids comprise a tetrazine. In some embodiments, the one or more noncanonical amino acids comprise an aryl azide. In some embodiments, the one or more noncanonical amino acids comprising an aryl azide are selected from the group consisting of p-azido-L-phenylalanine (AzF), 3-azido-L-tyrosine (AzY), and a combination thereof. In some embodiments, the noncanonical amino acid is AzF. In some embodiments, the noncanonical amino acid is AzY.

In some embodiments, the one or more variant aminoacyl-tRNA synthetases activate the one or more tRNAs in the cell preferentially with the one or more noncanonical amino acids compared to a canonical amino acid. In some embodiments, the variant aminoacyl-tRNA synthetase exhibits higher selectivity for a noncanonical amino acid, compared to a canonical amino acid, when activating a tRNA. In some embodiments, the activation of a tRNA with a noncanonical amino acid (i.e., by the variant aminoacyl-tRNA synthetase) is at least about 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 10.5-fold, 11-fold, 11.5-fold, 12-fold, 12.5-fold, 13-fold, 13.5-fold, 14-fold, 14.5-fold, 15-fold, 15.5-fold, 16-fold, 16.5-fold, 17-fold, 17.5-fold, 18-fold, 18.5-fold, 19-fold, 19.5-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold, 110-fold, 120-fold, 130-fold, 140-fold, 150-fold, 160-fold, 170-fold, 180-fold, 190-fold, 200-fold, 210-fold, 220-fold, 230-fold, 240-fold, 250-fold, 260-fold, 270-fold, 280-fold, 290-fold, or 300-fold faster than activation with a canonical amino acid (e.g., a similar or corresponding canonical amino acid).

In some embodiments, the detectable moiety comprises a fluorophore (e.g., for imaging), an affinity resin (e.g., for spectrometric characterization), a chemical stain, a chemical indicator, or a crosslinking reagent that can be used, for example, to investigate protein interactions. In some embodiments, the labeled proteome, labeled protein, or population of labeled proteins is detected using a method selected from the group consisting of fluorescent imaging, flow cytometry, mass spectrometry, and a combination thereof.

The compositions and methods of the present invention can be used for labeling the proteome of any cell of interest, or for labeling a protein or population of proteins produced by any cell of interest. The cell of interest can be a cell from any organism, e.g., a bacterial cell, an archaeal cell, a cell of a single-cell eukaryotic organism, a plant cell (e.g., a rice cell, a wheat cell, a tomato cell, an *Arabidopsis thaliana* cell, a *Zea mays* cell and the like), an algal cell (e.g., *Botryococcus braunii, Chlamydomonas reinhardtii, Nannochloropsis gaditana, Chlorella pyrenoidosa, Sargassum patens C. Agardh*, and the like), a fungal cell (e.g., yeast cell, etc.), an animal cell, a cell from an invertebrate animal (e.g., fruit fly, cnidarian, echinoderm, nematode, etc.), a cell from a vertebrate animal (e.g., fish, amphibian, reptile, bird, rodent, mammal, etc.), a cell from a mammal, a cell from a mouse, a cell from a rat, a cell from a non-human primate, a cell from a human, a cell from a healthy human, a cell from a human patient, etc.

In some embodiments, the cell is from a human cancer patient, a human patient having a neurological disease (e.g., a neurodegenerative disease), or a human patient having an immune, an autoimmune, an inflammatory disease, or a metabolic disease (e.g., metabolic syndrome). The cell can also be obtained from or derived from an in vivo or an animal model (e.g., an in vivo or animal model of cancer, a neurological disease (e.g., a neurodegenerative disease), an immune disorder, an autoimmune disorder, or an inflammatory disorder). Methods and compositions of the present invention can also be used in studies of aging (e.g., by labeling proteomes, proteins, or populations of proteins in senescent cells). In some embodiments, the cell is obtained from or derived from a patient-derived xenograft model. The cell can be in vivo or in vitro.

Any type of cell may be of interest, such as a stem cell, e.g., embryonic stem cell, induced pluripotent stem cell, adult stem cell, e.g., mesenchymal stem cell, neural stem cell, hematopoietic stem cell, organ stem cell, a progenitor cell, a somatic cell, e.g., fibroblast, hepatocyte, heart cell, liver cell, pancreatic cell, muscle cell, skin cell, blood cell, neural cell e.g., a central nervous system cell, peripheral nervous system cell, neuron, brain cell, or spinal cord cell), immune cell, and any other cell of the body, e.g., human or animal body. The cells can be primary cells or primary cell cultures derived from a subject, e.g., an animal subject or a human subject, and allowed to grow in vitro for a limited number of passages. In some embodiments, the cells are disease cells or derived from a subject with a disease. For instance, the cells can be cancer or tumor cells (e.g., melanoma cells), degenerating neural cells (e.g., degenerating neurons), or inflamed immune cells. The cells can also be immortalized cells (e.g., cell lines), for instance, from a cancer cell line. A cell of interest can also be a transplanted cell (e.g., a human cell that is transplanted into another animal such as a mouse, or a human cell contained within or derived from an organoid or organ that is transplanted into another animal such as a mouse).

Cells of interest can be harvested from a subject by any standard method. For instance, cells from tissues, such as skin, muscle, bone marrow, spleen, liver, kidney, pancreas, lung, intestine, stomach, etc., can be harvested by a tissue biopsy or a fine needle aspirate. Blood cells and/or immune cells can be isolated from whole blood, plasma or serum. In some cases, suitable primary cells include peripheral blood mononuclear cells (PBMC), peripheral blood lymphocytes (PBL), and other blood cell subsets such as, but not limited to, T cell, a natural killer cell, a monocyte, a natural killer T cell, a monocyte-precursor cell, a hematopoietic stem cell or a non-pluripotent stem cell. In some cases, the cell can be any immune cells including any T-cell such as tumor infiltrating cells (TILs), such as CD3+ T-cells, CD4+ T-cells, CD8+ T-cells, or any other type of T-cell. The T cell can also include memory T cells, memory stem T cells, or effector T cells. The T cells can also be skewed towards particular populations and phenotypes. For example, the T cells can be skewed to phenotypically comprise, CD45RO(−), CCR7(+), CD45RA(+), CD62L(+), CD27(+), CD28(+) and/or IL-7Rα (+). Suitable cells can be selected that comprise one of more markers selected from a list comprising: CD45RO(−), CCR7 (+), CD45RA(+), CD62L(+), CD27(+), CD28(+) and/or IL-7Rα(+). Induced pluripotent stem cells can be generated from differentiated cells according to standard protocols described in, for example, U.S. Pat. Nos. 7,682,828, 8,058,065, 8,530,238, 8,871,504, 8,900,871 and 8,791,248, the disclosures are herein incorporated by reference in their entirety for all purposes.

In some embodiments, the cell is a mammalian cell. In some embodiments, the cell is a human cell. In some embodiments, the cell is an immune cell, a neural cell, or a liver cell (e.g., hepatocyte). In some embodiments, the neural cell is a central nervous system (CNS) cell, a brain cell, a spinal cord cell, or a combination thereof. In some embodiments, the cell is selected from the group consisting of a cancer cell, a transplanted cell, a senescent cell, a degenerating neuron, and an inflamed immune cell. In some embodiments, the cancer cell is derived from an animal model and/or a patient-derived xenograft model. In some embodiments, the cancer cell is a melanoma cell.

In some embodiments, the labeled proteome (or portion thereof), protein, or population of labeled proteins is specific to one or more cell types. In some embodiments, the labeled protein or population of labeled proteins is specific to one or more particular types of diseased cells. As non-limiting examples, the labeled protein or population of labeled proteins can be specific to a cancer cell (e.g., a melanoma cell), a diseased neural cell (e.g., a diseased central nervous system cell, peripheral nervous system cell, brain cell, or spinal cord cell) such as a neural cell affected by a neurodegenerative disease, or an immune cell (e.g., an immune cell affected by an inflammatory disease or process and/or an autoimmune disease).

In some embodiments, the labeled proteome (or portion thereof), protein, or population of labeled proteins is specific to a particular organelle or cell compartment (e.g., the cytoplasm, an endosome, a chromosome, a ribosome, the endoplasmic reticulum, a mitochondrion, the nucleus, the cytoskeleton, the plasma membrane, the cell surface, the extracellular space, one or more intracellular organelles, or one or more intracellular complexes).

In some embodiments, the labeled proteome (or portion thereof), protein, or population of labeled proteins is specific to one or more cellular pathways (e.g., metabolic pathways).

In some embodiments, the one or more cellular pathways are dysregulated in one or more disease processes, or contribute to the development of one or more disease processes. Non-limiting examples of disease processes include cancer (e.g., melanoma), neurological diseases, neurodegenerative diseases, inflammatory diseases, autoimmune diseases, and metabolic diseases (e.g., metabolic syndrome). Non-limiting examples of cellular pathways include mitochondrial dysfunction, sirtuin signaling, phagosome maturation, protein ubiquination, fatty acid beta-oxidation, oxidative phosphorylation, remodeling of epithelial adherens junctions, NRF2-mediated oxidative stress responses, glycolysis, gluconeogenesis, LXR/FXR/RXR activation, acute phase response signaling, p70S6K signaling, and the pentose phosphate pathway.

In some embodiments, the labeling of a proteome (or portion thereof), protein, or population of proteins is temporally-restricted, e.g., the labeled proteome (or portion thereof), protein, or population of labeled proteins is specific to a particular time or phase in a cell cycle, a particular developmental stage, or a particular time point(s) following the administration of a drug or other therapeutic or experimental intervention.

In some embodiments, the variant aminoacyl-tRNA synthetase is introduced into a cell by introducing into the cell a polynucleotide described herein (e.g., a polynucleotide comprising a nucleic acid sequence that encodes one or more variant aminoacyl-tRNA synthetases that recognize noncanonical amino acids) and then expressing the variant aminoacyl-tRNA synthetase(s) from the polynucleotide. Any suitable viral agent (e.g., adeno-associated virus, adenovirus, etc.) or non-viral agent (e.g., liposomes, cationic polymers, etc.) can be used to introduce the polynucleotide into the cell. The expressed variant aminoacyl-tRNA synthetase can then incorporate noncanonical amino acids into the proteome of the cell, or incorporate noncanonical amino acids into a protein or population of proteins produced by the cell (e.g., the secretome of the cell). Alternatively, for some in vitro applications the one or more variant aminoacyl-tRNA synthetases can be expressed, isolated from the cell, and then purified (e.g., the expressed variant aminoacyl-tRNA synthetases can be isolated and purified from cell lysate). In any of these embodiments, it is useful, in some instances, to express the variant aminoacyl-tRNA synthetase from a polynucleotide that contains a nucleic acid sequence encoding a regulatory element.

In some embodiments, noncanonical amino acids are introduced into a cell by incubating the cell with a suitable amount of one or more noncanonical amino acids under appropriate cell culture conditions. For introducing noncanonical amino acids to a cell in vivo (e.g., to a target cell in a subject such as a human or an animal model such as a mouse), one or more noncanonical amino acids can be delivered by injection (e.g., intraperitoneal injection, intravenous injection such as in veins or in the retro-orbital sinus, subcutaneous injection, intrathecal injection, intramuscular injection, or direct tissue or organ (e.g., brain) injection). In certain embodiments, osmotic pumps or minipumps can be used to deliver noncanonical amino acids in vivo to either the systemic environment or directly to the tissue or organ (e.g., brain). In the context of delivery to the brain, noncanonical amino acids can mostly pass the blood-brain barrier to some degree, so direct introduction into the brain is often not necessary, but direct brain injection may improve labeling if a noncanonical amino acid does not cross the blood-brain barrier to a large degree (e.g., if less than about 10% of the noncanonical amino acid crosses the blood-brain barrier). In certain embodiments, noncanonical amino acids can be delivered in vivo by adding them to drinking water/liquid or food/feed. In certain embodiments, oral gavage can be used to deliver noncanonical amino acids in vivo, especially when more precise control over the amount of the noncanonical amino acid to be delivered is desired.

The regulatory element can be, for example, a transcription and/or a translational control element. Depending on the cell type or expression system being used, any of a number of transcription and translation control elements, including promoter, transcription enhancers, transcription terminators, and the like, may be employed. Useful promoters can be derived from viruses, or any organism, e.g., prokaryotic or eukaryotic organisms. Promoters may also be inducible (i.e., capable of responding to environmental factors and/or external stimuli that can be artificially controlled). Suitable promoters include, but are not limited to: RNA polymerase II promoters (e.g., pGAL7 and pTEF1), RNA polymerase III promoters (e.g., RPR-tetO, SNR52, and tRNA-tyr), the SV40 early promoter, an EF-1α promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6), an enhanced U6 promoter, a human H1 promoter (H1), etc. Suitable terminators include, but are not limited to SNR52 and RPR terminator sequences, which can be used with transcripts created under the control of a RNA polymerase III promoter. Additionally, various primer binding sites may be incorporated into a vector to facilitate vector cloning, sequencing, genotyping, and the like.

In some embodiments, the regulatory element is selected from the group consisting of an IRES sequence, a viral 2A peptide sequence, an inducible promoter, a cell-specific promoter, and a combination thereof. Introducing a viral 2A peptide sequence or an IRES sequence is particularly useful for co-expressing two or more variant aminoacyl-tRNA synthetases simultaneously (e.g., in order to increase proteome or protein labeling coverage, or to increase the sensitivity or specificity of cell or biomarker identification). Inducible and cell-specific promoters are useful, for example, for labeling proteins in specific cell types of interest (e.g., specific to particular tissues, developmental stages, or disease states) and can enable the production of temporal protein libraries and pulse studies to explore the half-lives or proteins of interest. For pulse labeling studies, a noncanonical amino acid can itself serve as a label, or the noncanonical amino acid can be labeled with a detectable moiety. Following administration of the noncanonical amino acid to the cell of interest, the absolute or relative amount of a labeled protein (or population of proteins) in the cell can be measured at multiple time points, which can be used to determine the half-life of the protein of interest. The amount of labeled protein in the cell can be measured while the cell is intact, or a cell sample can be obtained and lysed, followed by measurement of the amount of labeled protein.

In still another aspect, the present invention provides a method for identifying a target cell. In some embodiments, the method comprises: (a) labeling the proteome of the target cell or labeling a protein or a population of proteins produced by the target cell according to a method disclosed herein; (b) labeling the proteome of a reference cell or labeling a protein or a population of proteins produced by a reference cell according to a method disclosed herein; (c) detecting the labeled proteome, labeled protein, or population of labeled proteins in the target cell and reference cell to generate a target cell signature and a reference cell signature, respectively; (d) comparing the target cell signature to the reference cell signature; and (e) identifying the target cell based on the comparison in step (d).

In another aspect, the present invention provides a method for identifying one or more biomarkers of interest in a target cell. In some embodiments, the method comprises: (a) labeling the proteome of the target cell or labeling a protein or a population of proteins produced by the target cell according to a method disclosed herein; (b) labeling the proteome of a reference cell or labeling a protein or a population of proteins produced by a reference cell according to a method disclosed herein; (c) detecting the labeled proteome, labeled protein, or population of labeled proteins in the target cell and reference cell to generate a target cell signature and a reference cell signature, respectively; (d) comparing the target cell signature to the reference cell signature; and (e) identifying the one or more biomarkers of interest based on the comparison in step (d).

In some embodiments, the protein or population of proteins produced by the target cell and/or the reference cell are secreted by the target cell and/or the reference cell. In some embodiments, proteins will be labeled in the target cell that are not labeled in the reference cell. In some embodiments, proteins will be labeled in the reference cell that are not labeled in the target cell. In some embodiments, the same protein(s) will be labeled in both the target cell and the reference cell, but there will be a quantitative difference (e.g., a difference that is at least about 1.5-fold, 2-fold, 5-fold, 10-fold, 20-fold, 50-fold or more) between the amount of a particular protein that is labeled in the target cell compared to the amount of the protein that is labeled in the reference cell. In some instances, the amount of labeled protein will be greater in the target cell than in the reference cell. In some instances, the amount of labeled protein will be less in the target cell than in the reference cell.

In some embodiments, the target cell is a diseased cell. In some embodiments, the diseased cell is a cancer cell, a neurological disease cell, an inflammatory disease cell, an immune cell, an autoimmune disease cell, or a cell associated with a metabolic disease. In some embodiments, the neurological disease cell is a neurodegenerative disease cell. In some embodiments, the cancer cell is a melanoma cell. In some embodiments, the reference cell is a healthy cell.

Identification of biomarkers according to methods of the present invention is useful for understanding the mechanisms of many diseases, including cancer, neurological diseases (e.g., neurodegenerative diseases), immune diseases, inflammatory diseases, autoimmune diseases, metabolic diseases (e.g., metabolic syndrome), and aging. In particular, the proteins that are secreted by different types of cells (e.g., diseased and healthy cells) are often different, so large-scale identification of the differences in protein production and/or secretion between cell types can be used to better understand the complex changes that underlie disease processes. Methods of the present invention can also be used to diagnose various diseases and/or determine a prognosis (e.g., for a patient). Furthermore, methods of the present invention are useful for identifying new therapeutic targets for any number of diseases, such as those described herein.

In some embodiments, the target cell and/or the reference cell is obtained from or derived from an in vivo model system and/or a patient-derived xenograft. Such models are useful for studying various cancers, among other diseases.

In some embodiments, the labeled proteome, labeled protein, or population of labeled proteins is present in a sample obtained from a subject. In some embodiments, the sample is obtained from the subject before and/or after the proteome, protein, or population of proteins is labeled and/or detected. In some embodiments, the sample comprises a labeled secretome or a portion thereof. In some embodiments, the labeled secretome or portion thereof is detected after being secreted from the target cell and/or reference cell. In some embodiments, the sample is a blood sample, a urine sample, a saliva sample, a cerebrospinal fluid sample, a tissue sample, a fine needle aspirate sample, a biopsy sample, or a combination thereof.

In some embodiments, two or more (e.g., 2, 3, 4, 5, or more) variant aminoacyl-tRNA synthetases that recognize noncanonical amino acids are used. In some embodiments, using two or more variant aminoacyl-tRNA synthetases that recognize noncanonical amino acids increases the sensitivity and/or specificity of target cell or biomarker identification, compared to when only one variant aminoacyl-tRNA synthetase that recognizes a noncanonical amino acid is used. In some embodiments, the sensitivity and/or specificity of target cell or biomarker identification is increased by at least about 1.1-fold, 1.2-fold, 1.3-fold, 1.4-fold, 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 10.5-fold, 11-fold, 11.5-fold, 12-fold, 12.5-fold, 13-fold, 13.5-fold, 14-fold, 14.5-fold, 15-fold, 15.5-fold, 16-fold, 16.5-fold, 17-fold, 17.5-fold, 18-fold, 18.5-fold, 19-fold, 19.5-fold, or 20-fold when two or more variant aminoacyl-tRNA synthetases that recognize noncanonical amino acids are used, compared to when only one variant aminoacyl-tRNA synthetase that recognizes a noncanonical amino acid is used. In some embodiments, the sensitivity and/or specificity of a diagnosis and/or prognosis is increased when two or more variant aminoacyl-tRNA synthetases that recognize noncanonical amino acids are used, compared to when only one variant aminoacyl-tRNA synthetase that recognizes a noncanonical amino acid is used.

B. Compositions

In another aspect, the present invention provides a labeled protein or a population of labeled proteins that are labeled by a method disclosed herein. In some embodiments, the labeled protein or population of labeled proteins comprises the proteome of a cell. In some embodiments, the labeled protein or population of labeled proteins comprises a portion of the proteome of a cell. In some embodiments, the labeled protein or population of labeled proteins comprises the secretome of a cell. In some embodiments, the labeled protein or population of labeled proteins comprises a portion of the secretome of a cell. In some embodiments, the labeled protein or population of labeled proteins is secreted by a cell. In some embodiments, one or more isoforms or variants of a protein are labeled. In some embodiments, all isoforms or variants of a protein are labeled.

In some embodiments, the labeled protein or population of labeled proteins is specific to one or more cell types. In some embodiments, the labeled protein or population of labeled proteins is specific to one or more particular types of diseased cells. As non-limiting examples, the labeled protein or population of labeled proteins can be specific to a cancer cell (e.g., a melanoma cell), a diseased neural cell (e.g., a diseased central nervous system cell, peripheral nervous system cell, brain cell, or spinal cord cell) such as a neural cell affected by a neurodegenerative disease, an immune cell (e.g., an immune cell affected by an inflammatory disease or process and/or an autoimmune disease), or a cell affected by a metabolic disease (e.g., metabolic syndrome).

In some embodiments, the labeled protein or population of labeled proteins is specific to a particular organelle or cell compartment (e.g., the cytoplasm, an endosome, a chromosome, a ribosome, the endoplasmic reticulum, a mitochondrion, the nucleus, the cytoskeleton, the plasm membrane, the cell surface, the extracellular space, one or more intracellular organelles, or one or more intracellular complexes).

In some embodiments, the labeled protein or population of labeled proteins is specific to one or more cellular pathways (e.g., metabolic pathways). In some embodiments, the one or more cellular pathways are dysregulated in one or more disease processes, or contribute to the development of one or more disease processes. Non-limiting examples of disease processes include cancer (e.g., melanoma), neurological diseases, neurodegenerative disease, immune diseases, inflammatory diseases, autoimmune diseases, and metabolic diseases such as metabolic syndrome. Non-limiting examples of cellular pathways include mitochondrial dysfunction, sirtuin signaling, phagosome maturation, protein ubiquination, fatty acid beta-oxidation, oxidative phosphorylation, remodeling of epithelial adherens junctions, NRF2-mediated oxidative stress responses, glycolysis, gluconeogenesis, LXR/FXR/RXR activation, acute phase response signaling, p70S6K signaling, and the pentose phosphate pathway.

In some embodiments, the labeled protein or population of labeled proteins is specific to a particular temporal window, e.g., a particular time or phase of a cell cycle, a particular developmental stage, or a particular time point(s) following the administration of a drug or other therapeutic or experimental intervention.

In yet another aspect, the present invention provides an isolated polynucleotide encoding a variant aminoacyl-tRNA synthetase that recognizes a noncanonical amino acid. In some embodiments, the isolated polynucleotide comprises a nucleic acid sequence having at least about 70% identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOS:1-3. In some embodiments, the isolated polynucleotide comprises the nucleic acid sequence of any one of SEQ ID NOS:1-3.

In some embodiments, the isolated polynucleotide comprises a nucleic acid sequence having at least about 70% identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) to SEQ ID NO:1. In some embodiments, the isolated polynucleotide comprises the nucleic acid sequence set forth in SEQ ID NO:1.

In some embodiments, the isolated polynucleotide comprises a nucleic acid sequence having at least about 70% identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) to SEQ ID NO:2. In some embodiments, the isolated polynucleotide comprises the nucleic acid sequence set forth in SEQ ID NO:2.

In some embodiments, the isolated polynucleotide comprises a nucleic acid sequence having at least about 70% identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) to SEQ ID NO:3. In some embodiments, the isolated polynucleotide comprises the nucleic acid sequence set forth in SEQ ID NO:3.

In some embodiments, the nucleic acid sequence is codon-optimized to increase expression of the variant aminoacyl-tRNA synthetase, e.g., compared to expression from a nucleic acid sequence that is not codon-optimized. In some embodiments, the nucleic acid sequence is codon-optimized to increase expression in a particular cell type or species of interest (e.g., expression in a mammalian cell such as a human, non-human primate, mouse, or rat cell).

In some embodiments, when a nucleic acid sequence (e.g., a nucleic acid sequence encoding a variant aminoacyl-tRNA synthetase) is codon-optimized, expression from the nucleic acid sequence (e.g., expression of the variant aminoacyl-tRNA synthetase) is increased by at least about 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, or more compared to expression from the corresponding non-codon-optimized nucleic acid sequence.

In some embodiments, the encoded variant aminoacyl-tRNA synthetase comprises an amino acid substitution compared to a corresponding wild-type aminoacyl-tRNA synthetase. In some embodiments, the encoded variant aminoacyl-tRNA synthetase comprises an amino acid substitution in an amino acid binding pocket compared to a corresponding wild-type aminoacyl-tRNA synthetase. In general, amino acid substitutions that allow for more room within the amino acid binding pocket (i.e., in order to better accommodate a larger noncanonical amino acid) are desired. In some embodiments, the amino acid substitution replaces a wild-type amino acid with a smaller amino acid. In some embodiments, the amino acid substitution replaces a wild-type amino acid with a glycine. In some embodiments, the encoded aminoacyl-tRNA synthetase comprises one or more (e.g., 1, 2, 3, 4, 5, or more) amino acid substitutions relative to the amino acid sequence set forth in SEQ ID NO:7, 8, or 9.

Variant aminoacyl-tRNA synthetases can be engineered or derived from any appropriate organism. Non-limiting examples include *Escherichia coli, Methanococcus jannaschii, Methanosarcina barkeri, Methanosarcina mazei, Saccharomyces cerevisiae* (Sc), *Caenorhabditis elegans, Drosophila melanogaster, Danio rerio, Mus musculus* (Mm), and *Homo sapiens* (Hs). In some embodiments, the encoded variant aminoacyl-tRNA synthetase is selected from the group consisting of ScTyr$_{Y43G}$, MmPhe$_{T413G}$, and HsPhe$_{T413G}$. In some embodiments, the isolated polynucleotide encodes two or more (e.g., 2, 3, or more) variant aminoacyl-tRNA synthetases that recognize noncanonical amino acids. In some embodiments, the isolated polynucleotide encodes ScTyr$_{Y43G}$ and MmPhe$_{T413G}$, ScTyr$_{Y43G}$ and HsPhe$_{T413G}$, MmPhe$_{T413G}$ and HsPhe$_{T413G}$, or ScTyr$_{Y43G}$, MmPhe$_{T413G}$, and HsPhe$_{T413G}$.

In some embodiments, the encoded variant aminoacyl-tRNA synthetase comprises an amino acid sequence having at least about 70% identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOS:4-6. In some embodiments, the encoded variant aminoacyl-tRNA synthetase comprises the amino acid sequence of any one of SEQ ID NOS:4-6.

In some embodiments, the encoded variant aminoacyl-tRNA synthetase comprises an amino acid sequence having at least about 70% identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) to SEQ ID NO:4. In some embodiments, the encoded variant aminoacyl-tRNA synthetase comprises the amino acid sequence set forth in SEQ ID NO:4.

In some embodiments, the encoded variant aminoacyl-tRNA synthetase comprises an amino acid sequence having at least about 70% identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) to SEQ ID NO:5. In some embodiments, the encoded variant aminoacyl-tRNA synthetase comprises the amino acid sequence set forth in SEQ ID NO:5.

In some embodiments, the encoded variant aminoacyl-tRNA synthetase comprises an amino acid sequence having at least about 70% identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) to SEQ ID NO:6. In some embodiments, the encoded variant aminoacyl-tRNA synthetase comprises the amino acid sequence set forth in SEQ ID NO:6.

In some embodiments, the encoded variant aminoacyl-tRNA synthetase activates a tRNA preferentially with a noncanonical amino acid compared to a canonical amino acid. In some embodiments, the encoded variant aminoacyl-tRNA synthetase exhibits higher selectivity for a noncanonical amino acid, compared to a canonical amino acid, when activating a tRNA. In some embodiments, the activation of a tRNA with a noncanonical amino acid (i.e., by the encoded variant aminoacyl-tRNA synthetase) is at least about 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 10.5-fold, 11-fold, 11.5-fold, 12-fold, 12.5-fold, 13-fold, 13.5-fold, 14-fold, 14.5-fold, 15-fold, 15.5-fold, 16-fold, 16.5-fold, 17-fold, 17.5-fold, 18-fold, 18.5-fold, 19-fold, 19.5-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold, 110-fold, 120-fold, 130-fold, 140-fold, 150-fold, 160-fold, 170-fold, 180-fold, 190-fold, 200-fold, 210-fold, 220-fold, 230-fold, 240-fold, 250-fold, 260-fold, 270-fold, 280-fold, 290-fold, or 300-fold faster than activation with a canonical amino acid (e.g., a similar or corresponding canonical amino acid).

In some embodiments, the isolated polynucleotide further comprises a nucleic acid sequence encoding a regulatory element. The regulatory element can be, for example, a transcription and/or a translational control element. Such regulatory elements are useful, for example, for expressing a variant aminoacyl-tRNA synthetase in a cell of interest (e.g., a cell in which the proteome will be labeled or a cell that produces a protein or population of proteins that will be labeled. Alternatively, such regulatory elements are useful for expressing or manufacturing variant aminoacyl-tRNA synthetases (e.g., using cell-based expression systems). The expressed variant aminoacyl-tRNA synthetases can be subsequently isolated and purified.

Depending on the cell type or expression system being used, any of a number of transcription and translation control elements, including promoter, transcription enhancers, transcription terminators, and the like, may be employed. Useful promoters can be derived from viruses, or any organism, e.g., prokaryotic or eukaryotic organisms. Promoters may also be inducible (i.e., capable of responding to environmental factors and/or external stimuli that can be artificially controlled). Suitable promoters include, but are not limited to: RNA polymerase II promoters (e.g., pGAL7 and pTEF1), RNA polymerase III promoters (e.g., RPR-tetO, SNR52, and tRNA-tyr), the SV40 early promoter, an EF-1α promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6), an enhanced U6 promoter, a human H1 promoter (H1), etc. Suitable terminators include, but are not limited to SNR52 and RPR terminator sequences, which can be used with transcripts created under the control of a RNA polymerase III promoter. Additionally, various primer binding sites may be incorporated into a vector to facilitate vector cloning, sequencing, genotyping, and the like.

In some embodiments, the regulatory element is selected from the group consisting of an IRES sequence, a viral 2A peptide sequence, an inducible promoter, a cell-specific promoter, and a combination thereof. Introducing a viral 2A peptide sequence or an IRES sequence is particularly useful for co-expressing two or more variant aminoacyl-tRNA synthetases simultaneously (e.g., in order to increase proteome or protein labeling coverage, or to increase the sensitivity or specificity of cell or biomarker identification). Inducible and cell-specific promoters are useful, for example, for labeling proteins in cell types of interest (e.g., specific to particular tissues, developmental stages, or disease states) and can enable the production of temporal collections of labeled proteomes, as well as pulse studies to explore the half-lives or proteins of interest. For pulse labeling studies, a noncanonical amino acid can itself serve as a label, or the noncanonical amino acid can be labeled with a detectable moiety. Following administration of the noncanonical amino acid to the cell of interest, the absolute or relative amount of a labeled protein (or population of proteins) in the cell can be measured at multiple time points, which can be used to determine the half-life of the protein of interest. The amount of labeled protein in the cell can be measured while the cell is intact, or a cell sample can be obtained and lysed, followed by measurement of the amount of labeled protein.

In another aspect, the present invention provides a cell that comprises a polynucleotide disclosed herein. The compositions and methods of the present invention can be used for labeling the proteome (or a portion thereof) of any cell of interest, or for labeling a protein or population of proteins of any cell of interest. The cell of interest can be a cell from any organism, e.g., a bacterial cell, an archaeal cell, a cell of a single-cell eukaryotic organism, a plant cell (e.g., a rice cell, a wheat cell, a tomato cell, an *Arabidopsis thaliana* cell, a *Zea mays* cell and the like), an algal cell (e.g., *Botryococcus braunii, Chlamydomonas reinhardtii, Nannochloropsis gaditana, Chlorella pyrenoidosa, Sargassum patens C. Agardh*, and the like), a fungal cell (e.g., yeast cell, etc.), an animal cell, a cell from an invertebrate animal (e.g., fruit fly, cnidarian, echinoderm, nematode, etc.), a cell from a vertebrate animal (e.g., fish, amphibian, reptile, bird, rodent, mammal, etc.), a cell from a mammal, a cell from a mouse, a cell from a rat, a cell from a non-human primate, a cell from a human, a cell from a healthy human, a cell from a human patient, etc. In some embodiments, the cell is from a human cancer patient, a human patient having a neurological disease (e.g., a neurodegenerative disease), or a human patient having an immune, an autoimmune, or an inflammatory disease. The cell can also be obtained from or derived from an in vivo or an animal model (e.g., an in vivo or animal model of cancer, a neurological disease (e.g., a neurodegenerative disease), an immune disease, an autoimmune disease, an inflammatory disease, or a metabolic disease (e.g., metabolic syndrome)). For instance, the cell can be obtained from or derived from a patient-derived xenograft model. The cell can be in vivo or in vitro.

Any type of cell may be of interest, such as a stem cell, e.g., embryonic stem cell, induced pluripotent stem cell, adult stem cell, e.g., mesenchymal stem cell, neural stem cell, hematopoietic stem cell, organ stem cell, a progenitor cell, a somatic cell, e.g., fibroblast, hepatocyte, heart cell, liver cell, pancreatic cell, muscle cell, skin cell, blood cell, neural cell e.g., a central nervous system cell, peripheral nervous system cell, neuron, brain cell, or spinal cord cell), immune cell, and any other cell of the body, e.g., human or animal body. The cells can be primary cells or primary cell cultures derived from a subject, e.g., an animal subject or a human subject, and allowed to grow in vitro for a limited number of passages. In some embodiments, the cells are disease cells or derived from a subject with a disease. For instance, the cells can be cancer or tumor cells, degenerating neural cells (e.g., degenerating neurons), or inflamed immune cells. The cells can also be immortalized cells (e.g., cell lines), for instance, from a cancer cell line. A cell of interest can also be a transplanted cell (e.g., a human cell that is transplanted into another animal such as a mouse, or a human cell contained within or derived from an organoid or organ that is transplanted into another animal such as a mouse).

Cells of interest can be harvested from a subject by any standard method. For instance, cells from tissues, such as skin, muscle, bone marrow, spleen, liver, kidney, pancreas, lung, intestine, stomach, etc., can be harvested by a tissue biopsy or a fine needle aspirate. Blood cells and/or immune cells can be isolated from whole blood, plasma or serum. In some cases, suitable primary cells include peripheral blood mononuclear cells (PBMC), peripheral blood lymphocytes (PBL), and other blood cell subsets such as, but not limited to, T cell, a natural killer cell, a monocyte, a natural killer T cell, a monocyte-precursor cell, a hematopoietic stem cell or a non-pluripotent stem cell. In some cases, the cell can be any immune cells including any T-cell such as tumor infiltrating cells (TILs), such as CD3+ T-cells, CD4+ T-cells, CD8+ T-cells, or any other type of T-cell. The T cell can also include memory T cells, memory stem T cells, or effector T cells. The T cells can also be skewed towards particular populations and phenotypes. For example, the T cells can be skewed to phenotypically comprise, CD45RO(−), CCR7(+), CD45RA(+), CD62L(+), CD27(+), CD28(+) and/or IL-7Rα (+). Suitable cells can be selected that comprise one of more markers selected from a list comprising: CD45RO(−), CCR7 (+), CD45RA(+), CD62L(+), CD27(+), CD28(+) and/or IL-7Rα(+). Induced pluripotent stem cells can be generated from differentiated cells according to standard protocols described in, for example, U.S. Pat. Nos. 7,682,828, 8,058, 065, 8,530,238, 8,871,504, 8,900,871 and 8,791,248, the disclosures are herein incorporated by reference in their entirety for all purposes.

In some embodiments, the cell further comprises one or more noncanonical amino acids. In some embodiments, the one or more noncanonical amino acids comprise an azide, an alkyne, a tetrazine, or a combination thereof. In some embodiments, the one or more noncanonical amino acids comprise an azide. In some embodiments, the one or more noncanonical amino acids comprise an alkyne. In some embodiments, the one or more noncanonical amino acids comprise a tetrazine. In some embodiments, the one or more noncanonical amino acids comprise an aryl azide. In some embodiments, the one or more noncanonical amino acids comprising an aryl azide are selected from the group consisting of p-azido-L-phenylalanine (AzF), 3-azido-L-tyrosine (AzY), and a combination thereof. In some embodiments, the noncanonical amino acid is AzF. In some embodiments, the noncanonical amino acid is AzY.

In some embodiments, the cell further comprises a detectable moiety. In some embodiments, the detectable moiety comprises a fluorophore (e.g., for imaging), an affinity resin (e.g., for spectrometric characterization), a chemical stain, a chemical indicator, or a crosslinking reagent that can be used, for example, to investigate protein interactions.

C. Kits

In another aspect, the present invention provides a kit for labeling the proteome (or a portion thereof) of a cell or for labeling a protein or a population of proteins produced by a cell. In some embodiments, the kit comprises a polynucleotide disclosed herein (e.g., a polynucleotide encoding a variant aminoacyl-tRNA synthetase that recognizes a noncanonical amino acid) and/or a cell disclosed herein (e.g., a cell comprising a polynucleotide encoding a variant aminoacyl-tRNA synthetase that recognizes a noncanonical amino acid).

In some embodiments, the kit further comprises one or more reagents. The reagents can be used, as non-limiting examples, to introduce a polynucleotide into the cell, to express a variant aminoacyl-tRNA synthetase in the cell, to introduce a noncanonical amino acid into the cell, to introduce a detectable moiety into the cell, to lyse the cell, and/or to detect the labeled proteome (or a portion thereof), the labeled protein, or the population of labeled proteins.

In some embodiments, the kit further comprises instructions for use. The instructions pertain to, as non-limiting examples, introducing a polynucleotide into the cell, expressing a variant aminoacyl-tRNA synthetase in the cell, introducing a noncanonical amino acid into the cell, introducing a detectable moiety into the cell, labeling the modified proteome (or a portion thereof), protein, or population of proteins (i.e., the proteome (or a portion thereof), protein, or population of proteins into which one or more noncanonical amino acids have been integrated) with the detectable moiety, detecting the labeled proteome (or a portion thereof), protein, or population of proteins, and/or isolating the labeled proteome (or a portion thereof), protein, or population of proteins from the cell (e.g., from a lysed cell). Furthermore, the instructions may pertain to generating a target cell signature and/or a reference cell signature (e.g., a signature based on the distinct populations of proteins that are labeled in the target cell and reference cell), comparing the target cell signature to the reference cell signature, identifying the cell (e.g., target cell) of interest, and/or identifying one or more biomarkers of interest (e.g., in the target cell).

IV. Examples

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1. Multiple Click-Selective tRNA Synthetases Expand Mammalian Cell-Specific Proteomics Organisms and tissues are composed of heterogeneous cell types. Robust and comprehensive cell-type-specific proteomics are foundational to understanding the biological processes underlying health and disease. For example, cell-secreted signaling proteins in blood have been shown to not only correlate with, but modulate organismal and brain aging (1-3). Current efforts to characterize cell-type-specific proteomes and secretomes rely on various cell isolation techniques before acute analysis or primary cell culture; however, these techniques likely perturb the in vivo proteome, completely lose the secretome, and lack temporal resolution (4-6).

Strategies to label the proteins of target cells with bioorthogonal moieties could enable subsequent enrichment and cell-type-specific proteomics (7-12). Labeling occurs via the metabolic incorporation of noncanonical amino acids (ncAAs) containing azide, alkyne, or other bioorthogonal side chains (13-15). Mutant aminoacyl-tRNA synthetases (aaRS) recognize ncAAs which are ignored by endogenous aaRSs. By expressing aaRSs under the control of cell-type-specific promotors or inducible genetic tools, one can achieve cell-type- and temporally-restricted metabolic protein labeling in vivo.

Figure 1B:
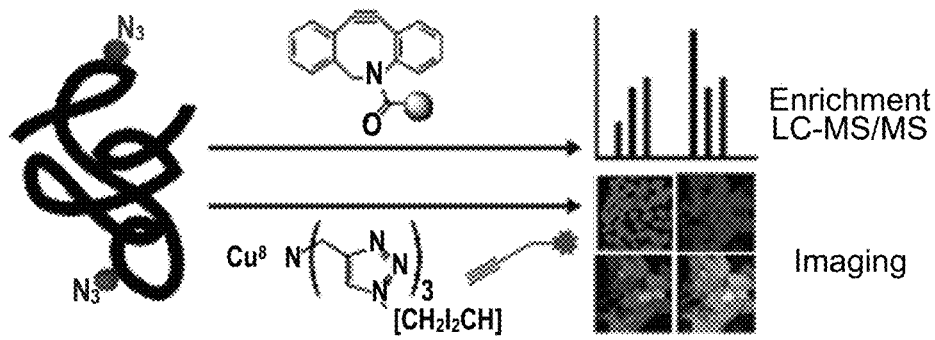

The recent development of the L274G mouse methionyl-tRNA synthetase (MmMet$_{L274G}$), and its rapid adoption in multicellular organisms from Drosophila to mice, has enabled the characterization of specific neuronal proteomes (10,16). However, MmMet$_{L274G}$ is currently the only mutant aaRS available for mammalian cell-type-specific proteomics and is limited to charging its single cognate tRNA$^{Met}$ (ATG) with the methionine surrogate azidonorleucine. As a result, reliance on MmMet$_{L274G}$ potentially constricts proteome coverage and skews subsequent analysis (17). Depending on the ncAA and targeted codon, labeling could perturb protein stability, folding, and trafficking; be performed at discordant rates; and be masked by steric effects or post-translational processing, such as N-terminal cleavage (18). Thus, mutant aaRSs likely label many proteins differentially, each preferring a subset of the whole proteome. To enable more robust and broader mammalian cell-type-specific proteomics, we identified and characterized two mutant aaRSs: a tyrosyl (ScTyr$_{Y43G}$) that charges the ncAA 3-azido-L-tyrosine (AzY) onto tRNA$^{Tyr}$ and a phenylalanyl (MmPhe$_{T413G}$) that charges p-azido-L-phenylalanine (AzF) onto tRNA$^{Phe}$ for incorporation into nascent proteins of host cells (FIG. 1A). Proteins can be labeled via either of the tRNA$^{Tyr}$ (TAT, TAC) and tRNA$^{Phe}$ (TTT, TTC) cognate codons. Incorporation does not require depletion of canonical amino acids or the strong co-expression of exogenous tRNAs, as exemplified by complementary approaches (12). Proteins labeled with AzY and AzF are chemoselectively tagged via azide-alkyne cycloadditions with fluorophores for imaging and flow cytometry or affinity resins for mass spectrometric identification and quantification (FIG. 1B).

To begin, we sought to convert microbial or metazoan aaRSs to be more broadly useful in mammals. We hypothesized that aaRSs and ncAAs developed in earlier genetic code expansion efforts could be adopted without their paired tRNAs: if species-specific tRNA-binding/aminoacylation determinants were properly deduced, the aaRS could be reoriented to recognize endogenous tRNAs for residue-specific proteome labeling (19-21). For example, we noticed that the M. jannaschii Tyr aaRS (TyrRS) used for site-specific ncAA incorporation in E. coli possesses eukaryotic tRNA-binding determinants (recognizes tRNA acceptor stem C1-G72) (22). This informed the testing of an engineered Mj TyrRS without its tRNA pair for residue-specific incorporation of AzF (20). We further spliced a 39 amino acid aminoacylation determinant from human TyrRS into an E. coli TyrRS reported to incorporate AzF ('CP1 switch') (23). Given the conserved archaeal/eukaryotic aminoacylation determinants of Mj TyrRS, we reasoned that aminoacylation would be preserved across eukaryotic TyrRS and adopted a yeast TyrRS (ScTyr$_{Y43G}$) reported to incorporate AzY (FIG. 2A and SEQ ID NOS:1 and 4) (24). Finally, the efficient labeling of C. elegans proteomes with an engineered CePheRS prompted us to develop human and mouse variants: HsPhe$_{T413G}$ and MmPhe$_{T413G}$ (FIG. 2B and SEQ ID NOS:2, 3, 5, and 6) (9).

Figure 6:
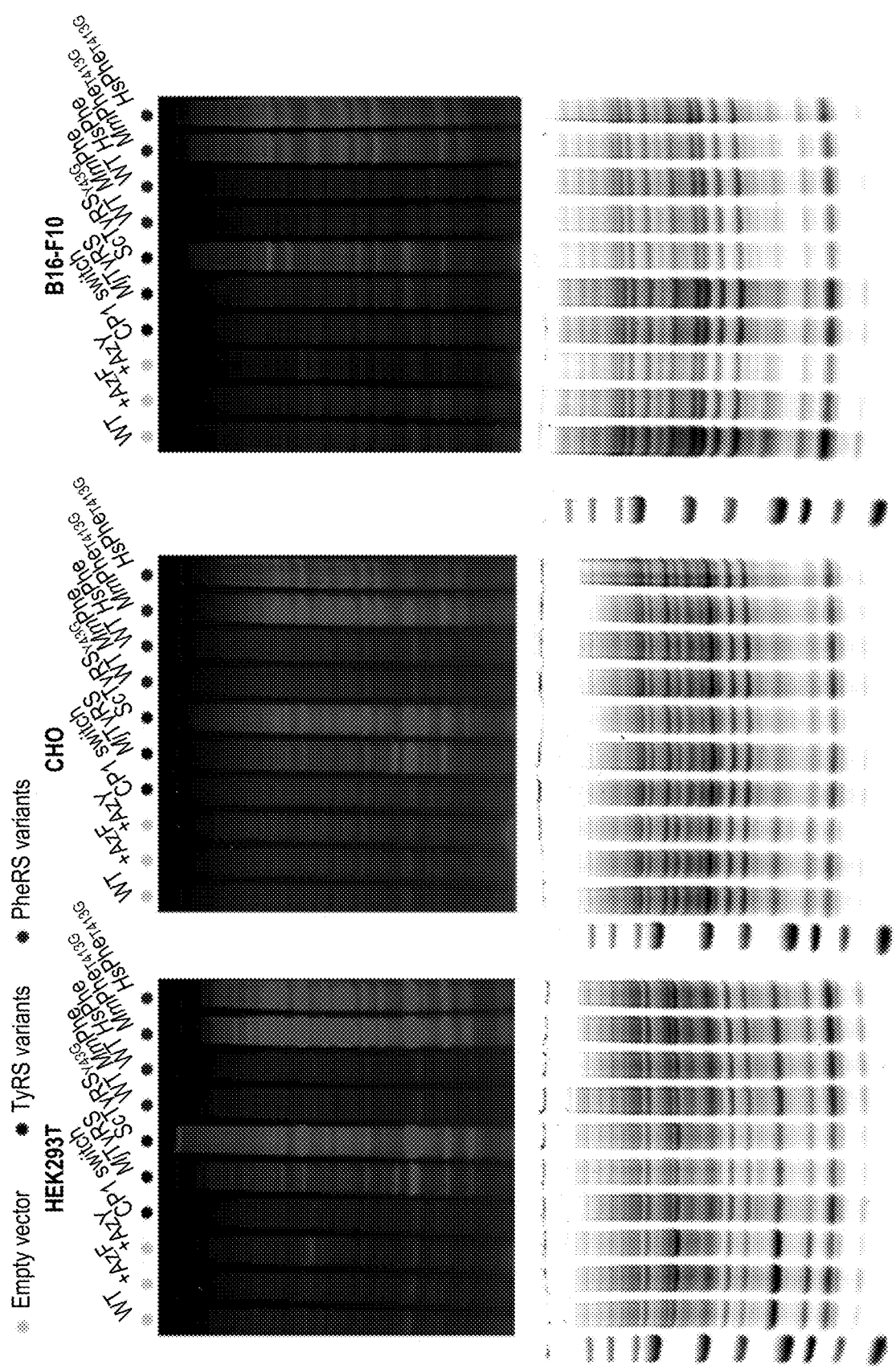
FIG. 6: Full-length gels for FIG. 2C. Full length fluorescent gels and protein loading controls for lysates from each mammalian cell type. After DIBO-Alexa Fluor 647 labeling and imaging for in-gel fluorescence, the relative amounts of protein loaded to each gel well were assessed via colloidal coomassie dye staining.

ScTyr$_{Y43G}$, HsPhe$_{T413G}$, and MmPhe$_{T413G}$ exhibited strong labeling in human HEK293T, hamster CHO, and mouse B16-F10 cell lines after transient transfection and incubation with high concentrations (2 mM) of AzY and AzF (FIGS. 2C and 6). Cells were lysed, pre-treated with iodoacetamide (IAM) to block background thiol-yne additions (25), and treated with dibenzocyclooctyne (DIBO)-Alexa Fluor 647 dye for copper-free, strain-promoted azide-alkyne cycloaddition.

Figure 7:
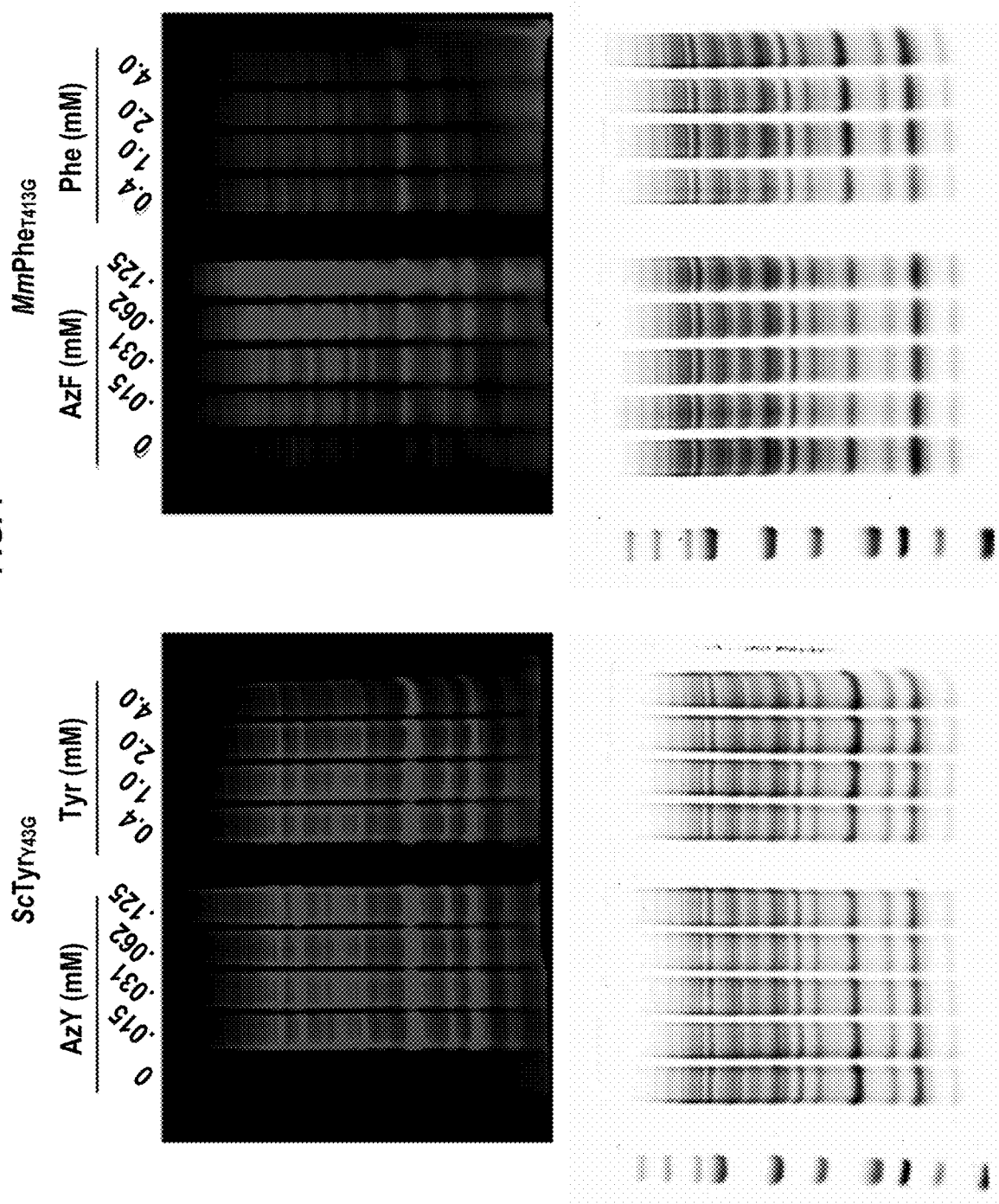
FIG. 7: Full-length gels for FIGS. 2D and 2E. Full length fluorescent gels and protein loading controls for lysates exposed to increasing concentrations of endogenous or non-canonical amino acids for 24 hours. Endogenous amino acid titration was performed with 0.015 mM of either AzY or AzF. Quantification was performed using biological triplicates, adapting previously described methods (36,37).

The selectivity of ScTyr$_{Y43G}$ and MmPhe$_{T413G}$ for AzY and AzF, respectively, over their endogenous counterparts Tyr and Phe is a critical determinant of their utility, especially in vivo. Minimizing the amount of exogenous ncAA required for proteome labeling likely reduces toxicities that may perturb the proteome. Adopting previously derived equations for ncAA activation (11), we quantified the extent of protein labeling in HEK293T cells as a function of AzY and AzF concentrations in serum-containing media (0 to 125 µM, 24 h); and performed the corollary Tyr and Phe competition assays with 15 µM AzY and AzF (FIGS. 2D, 2E and 7). Taking Alexa Fluor 647 (AF647) in-gel fluorescence as a measure of ncAA proteome incorporation, the line of best fit yields the rate of ncAA activation and the specificity constants ($k_{cat}/K_M$) for the ncAA and canonical amino acid. Interestingly, and in contrast with MmMet$_{L274G}$, ScTyr$_{Y43G}$ and MmPhe$_{T413G}$ exhibit high selectivity for their ncAA: the former activates AzY nearly 250-fold faster than Tyr at equimolar concentrations of the two amino acids; and the latter activates AzF over 11-fold faster than Phe, consistent with prior CePheRS$_{T413G}$ in vitro measurements (9).

Figure 8:
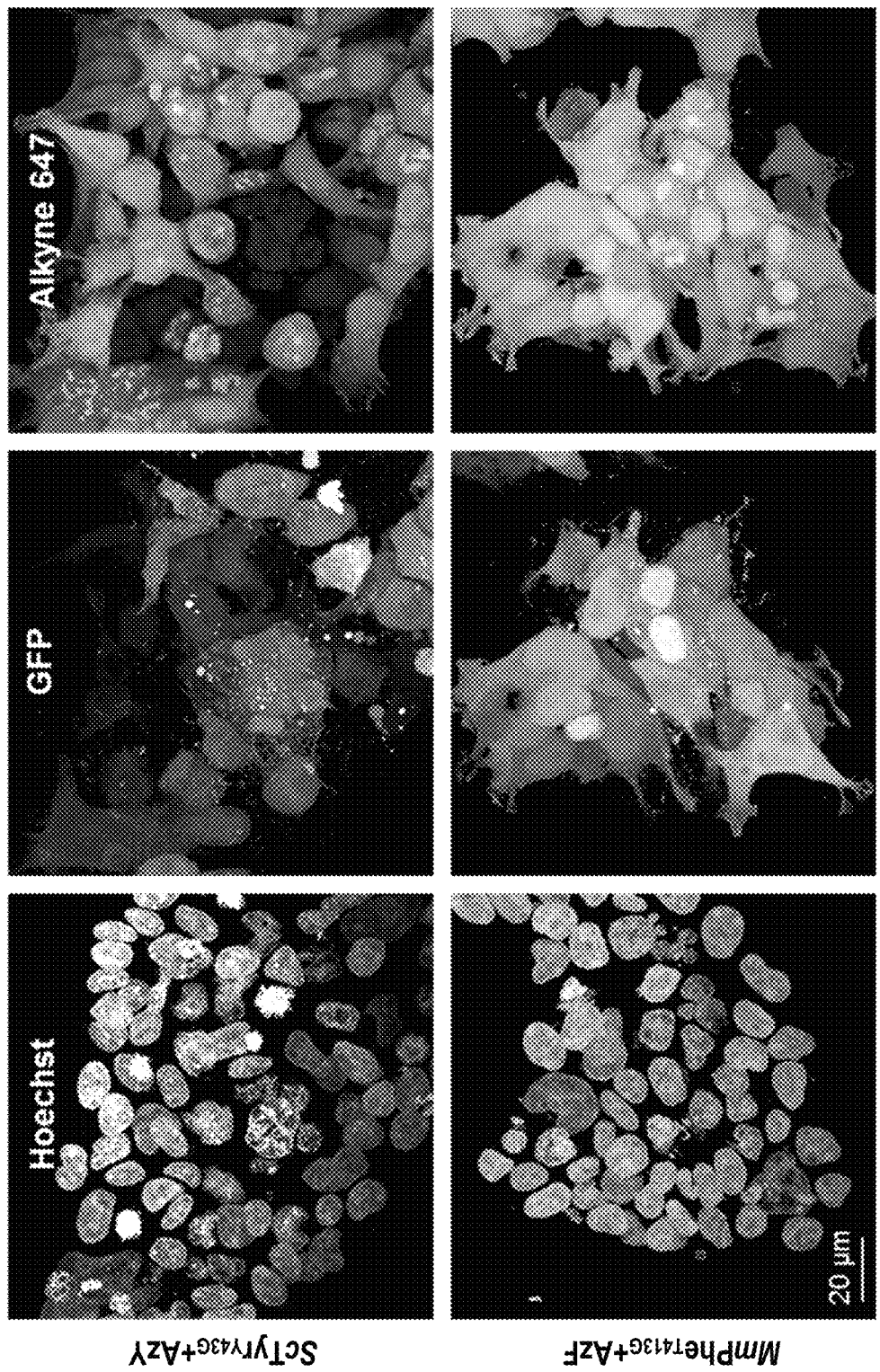
FIG. 8: Single channel images from fluorescence confocal microscopy for FIG. 3A. Single channel fluorescence confocal images of ScTyr$_{Y43G}$ and MmPhe$_{T413G}$-transfected HEK293T cells cultured with the non-canonical amino acids AzY and AzF, respectively. Images were obtained on a Zeiss LSM 880 microscope.
Figure 9:
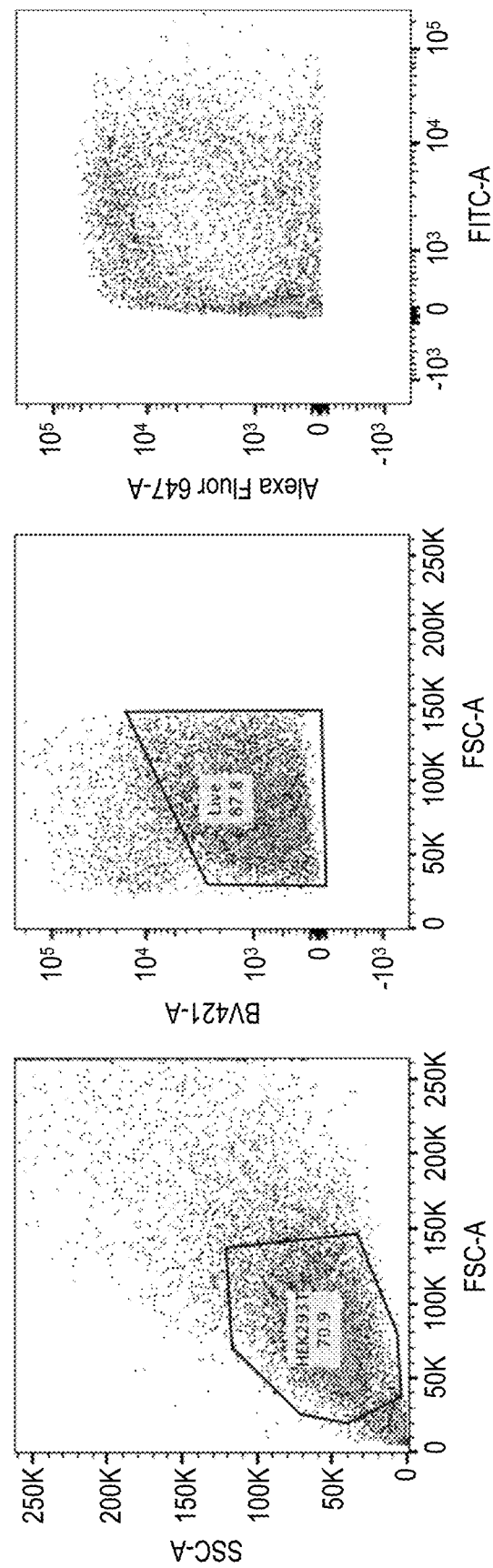
FIG. 9: Gating strategy used in flow cytometry analysis in FIG. 3C. Gating strategy for fixed HEK293T cells pretreated with iodoacetamide before reacting with DIBO Alexa Fluor 647. HEK293T cells were gated on a forward scatter (FSC)/side scatter (SSC) plot before live/dead discrimination. Below is a representative gating, showing a biological replicate from ScTyr$_{Y43G}$-transfected, AzY-exposed cells. The FITC-647 plot shows data with the FlowJo default biexponential axis.

We next determined whether proteome labeling by SCTy$_{Y43G}$ and MmPhe$_{T413G}$ was compatible with in situ fluorescence imaging, a critical modality for studying complex biology. Proteome labeling was visualized by tagging azide-bearing proteins with alkyne AF647 in HEK293T cells transfected with ScTyr$_{Y43G}$ or MmPhe$_{T413G}$ and exposed to 125 µM AzY or AzF (FIGS. 3A and 8). Mutant aaRSs were transfected in vectors co-expressing GFP: comparison of GFP$^+$ and AF647$^+$ areas indicated ubiquitous labeling across cells. To assess fluorescent proteome labeling across a cell population via flow cytometry, transfected and ncAA-exposed HEK293T cells were live/dead discriminated, fixed, IAM-treated, and tagged with DIBO-AF647. An AF647$^+$ subpopulation emerged even in the GFP$^{lo}$ regime, suggesting that even low ScTyr$_{Y43G}$ or MmPhe$_{T413G}$ expression is sufficient for maximal proteome labeling (FIGS. 3C and 9).

Hypothesizing that each mutant aaRS preferentially labels a subset of the full cell proteome, we transfected HEK293T cells with equal total amounts of plasmid containing MmMet$_{L274G}$, MmPhe$_{T413G}$, ScTyr$_{Y43G}$, or all three aaRSs; and exposed cells to 125 µM of their corresponding ncAAs or at least as much of endogenous amino acids. This amino acid concentration was informed by aaRS selectivity measurements (FIGS. 2D and 2E) and typical, nontoxic concentrations of exogenous agents in live mice. Labeled proteomes from cell lysates were enriched on azadibenzocyclooctyne (DBCO) beads, stringently washed, Trypsin/LysC digested, and conjugated to tandem mass tags (TMT) for multiplexed mass spectrometric characterization. We sought to (1) identify proteins uniquely enriched by each mutant aaRS; (2) quantify labeling efficiencies for each aaRS across commonly identified proteins; and (3) determine whether co-expression of aaRSs facilitates broader and more confident proteomics compared to single aaRS expression.

Figure 10:
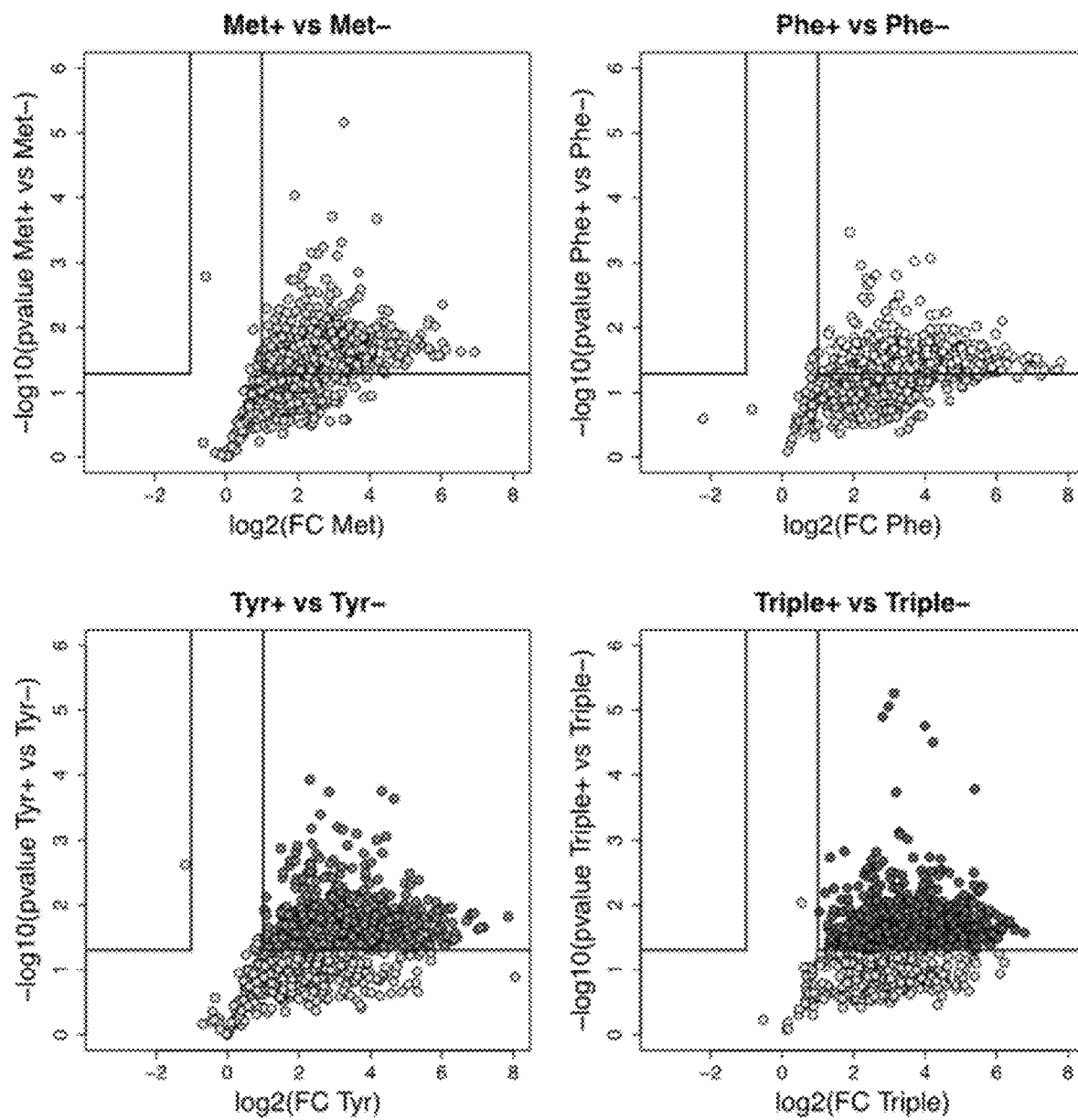
FIG. 10: Volcano plots identifying proteome subsets quantified by each mutant aaRS over nonspecific background from negative controls. In triplicate, HEK293T cells transfected with MmMet$_{L274G}$, MmPhe$_{T413G}$, and ScTyr$_{Y43G}$ were exposed to their corresponding ncAA: Anl, AzF, and AzF, respectively; or exposed to endogenous amino acids as negative controls to investigate background from nonspecific DBCO bead binding.
Figure 12:
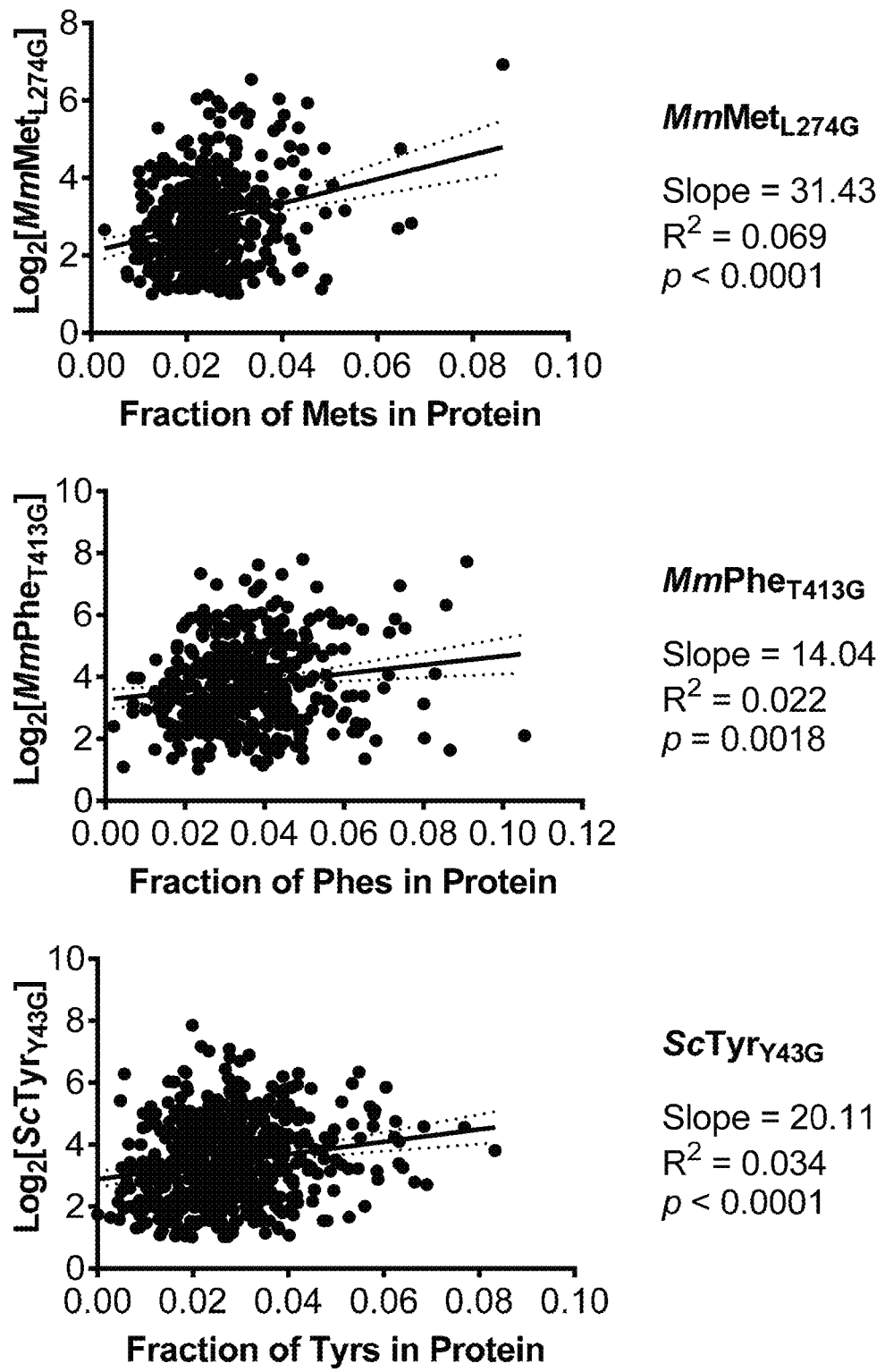
FIG. 12: The frequency of Met, Phe, and Tyr codons only partially explains the enrichment efficiencies by MmMet$_{L274G}$, MmPhe$_{T413G}$, and ScTyr$_{Y43G}$, respectively. The number of a cognate codon per protein, normalized by total protein length, weakly explains the mutant aaRS enrichment efficiency. The relative frequency of a target codon in a protein is plotted against the average enrichment fold-change between cells exposed to the ncAA (Anl, AzF, or AzY) or the canonical amino acid (Met, Phe, Tyr). Dotted lines indicate the 95% confidence interval of the least-square regression lines. These results are consistent with prior reports in E. coli (47), suggesting that a combination of factors determine mutant aaRS enrichment efficiency.

We found each mutant aaRS proteome sufficiently distinct to spatially segregate via principal component analysis (FIG. 4A). After filtering for proteins significantly labeled over nonspecific background (P-value<0.05 and $\log_2(FC)>1$, FIG. 10), we observed that each mutant aaRS labeled a distinct set of proteins: MmMet$_{L274G}$ alone identified 46 proteins overlooked by the other two mutant aaRSs, MmPhe$_{T413G}$ uniquely identified 54, and ScTyr$_{Y43G}$ uniquely identified 138 (FIG. 4B). On the other hand, most identified proteins were common across pairs of, if not all three, aaRSs (66%). Within the 463 proteins identified by at least two aaRSs, proteomic differences could arise from each mutant aaRS's labeling biases. Indeed, TMT-enabled quantification of protein abundances revealed that each mutant aaRS enriched different proteins with different efficiencies (FIGS. 4C and 12). Labeling efficiencies across proteins are consistent with prior selectivity measurements (FIGS. 2D and 2E).

Figure 11:
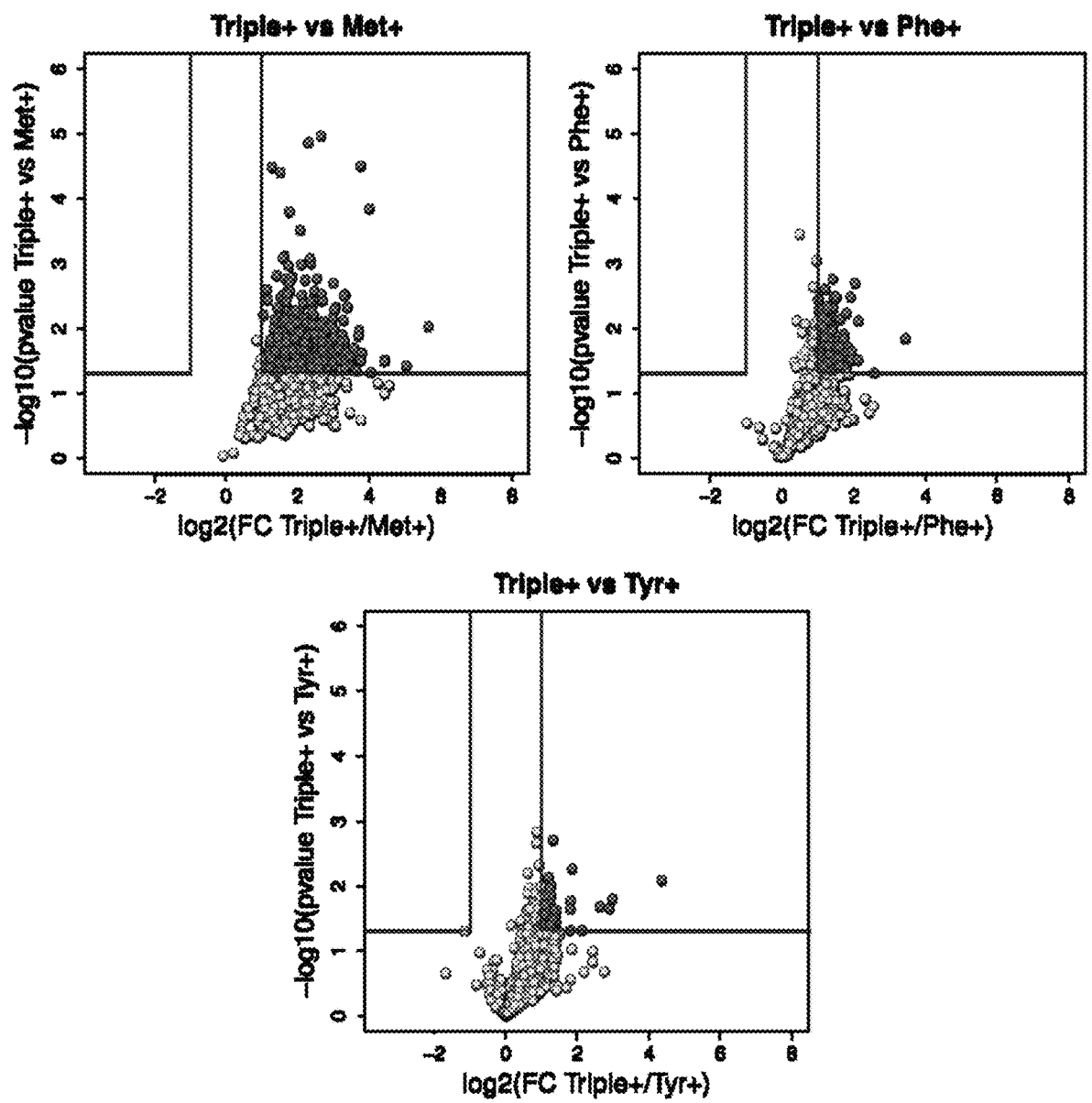
FIG. 11: Pairwise comparison of proteome subsets preferentially labeled between single and triply expressed mutant aaRSs in HEK293T cells.
Figure 13:
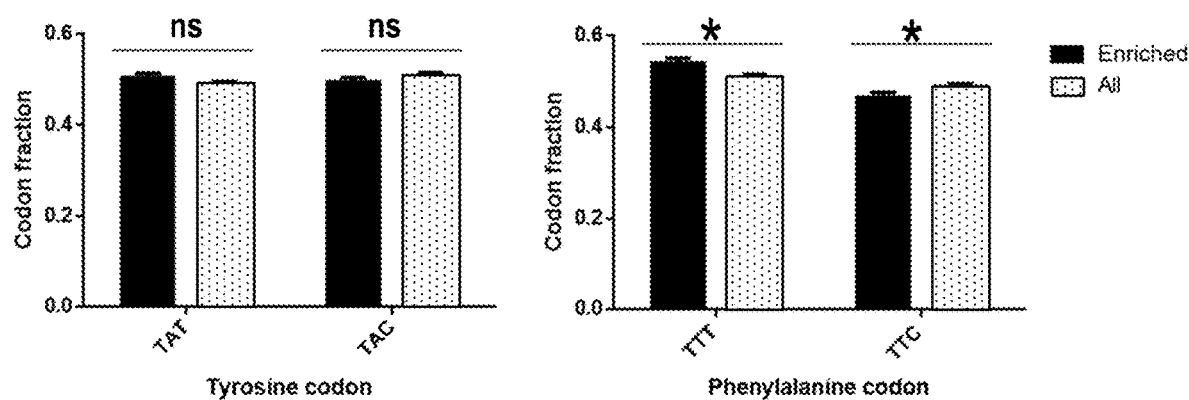
FIG. 13: ScTyr$_{Y43G}$ and MmPhe$_{T413G}$ label proteins via both of their cognate codons. HEKT293T proteins containing exclusively one of the two cognate codons for tyrosine and phenylalanine were significantly enriched by ScTyr$_{Y43G}$ and MmPhe$_{T413G}$, respectively, demonstrating that labeling can occur across codons. Proteins were TMT-labeled and quantified by mass spectrometry (FIG. 4). MmPhe$_{T413G}$ preferentially labels the TTT codon, whereas ScTyr$_{Y43G}$ labels both its cognate codons equally. The tyrosine and phenylalanine codon fraction of ScTyr$_{Y43G}$- and MmPhe$_{T413G}$-labeled proteins were compared with codon fractions of all TMT-identified proteins, including those not significantly enriched by ScTyr$_{Y43G}$+AzY and MmPhe$_{T413G}$+AzF over +Y and +F negative controls. cDNA could be retrieved from Ensembl for 450 proteins enriched in ScTyr$_{Y43G}$+AzY, 352 proteins enriched in MmPhe$_{T413G}$+AzF, and 1903 total proteins detected across TMT runs ('All') and used for this analysis. Data plotted as mean+SEM. *P<0.05; t-test.

MmPhe$_{T413G}$ and ScTyr$_{Y43G}$ label proteins through both their cognate codons (TTT, TTC; and TAT, TAC), with MmPhe$_{T413G}$ exhibiting a preference for TTT (FIG. 13). Having demonstrated preferential labeling by each mutant aaRS, we wondered whether aaRS co-expression could yield a more comprehensive and confidently identified cell proteome. The triple co-expression of MmMet$_{L274G}$, MmPhe$_{T413G}$, and ScTyr$_{Y43G}$ expanded proteome coverage and identified proteins more confidently (assessed by lower P-values) compared to single aaRS expression (FIGS. 4D and 11). Together, these data establish that the introduction of MmPhe$_{T413G}$ and ScTyr$_{Y43G}$ can improve mammalian cell-type-specific proteomics over MmMet$_{L274G}$ alone.

Figure 14:
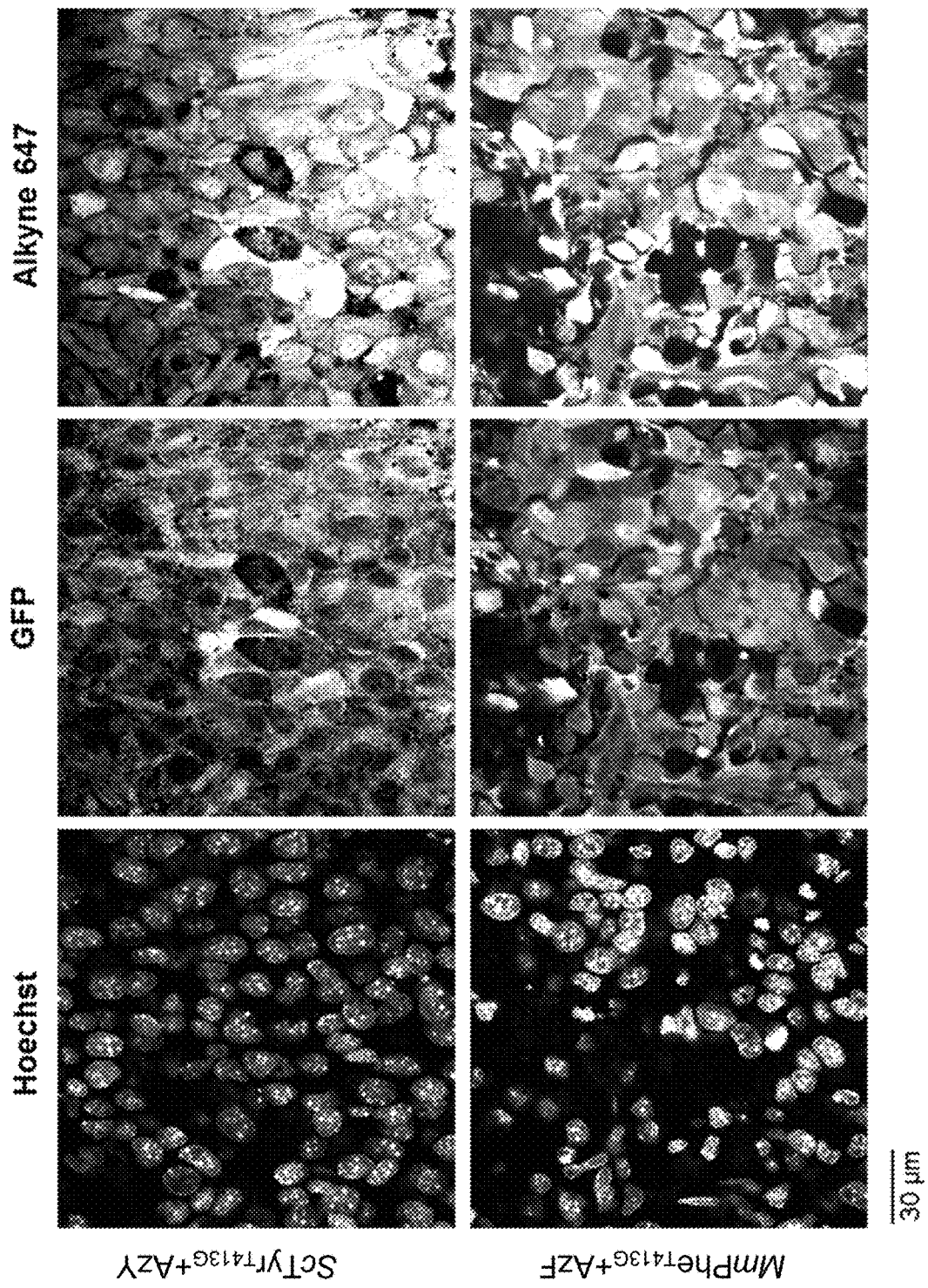
FIG. 14: Single channel images from fluorescence confocal microscopy for FIG. 5A. Single channel fluorescence confocal images of B16-F10 melanoma xenografts stably expressing ScTyr$_{Y43G}$ and MmPhe$_{T413G}$ exposed to the non-canonical amino acids AzY and AzF, respectively. Images were obtained on a Zeiss LSM 700 microscope.

To determine whether MmPhe$_{T413G}$ and ScTyr$_{Y43G}$ could label proteomes in vivo, we stably integrated each mutant aaRS into B16-F10 melanoma cells before subcutaneous implantation in 12-week-old C57BL/6 mice. 16 days after implantation, we administered saturating amounts of the corresponding ncAA intraperitoneally (1 mmol/kg) and intratumorally (~5 mM) daily for 3 days. Confocal fluorescence imaging of tumor sections revealed AzF or AzY proteome incorporation, assessed by chemoselective conjugation to alkyne AF647 (FIGS. 5A and 14). The restriction of AF647$^+$ signal to implanted GFP$^+$ melanoma cells amidst a wild-type C57BL/6 background suggests MmPhe$_{T413G}$ and ScTyr$_{Y43G}$ are suitable for additional in vivo tissue- and cell-type-specific proteomic applications. In-gel fluorescence of tumor lysates revealed labeling across the proteome (FIGS. 5B and 15). The stronger MmPhe$_{T413G}$ signal is consistent with FIG. 2C, where saturating amounts of ncAA delivered via intratumoral injection neutralized the selectivity advantages of ScTyr$_{Y43G}$. However, high ncAA selectivity could be advantageous in most in vivo applications where target cells are not directly accessible by needle.

Figure 16:
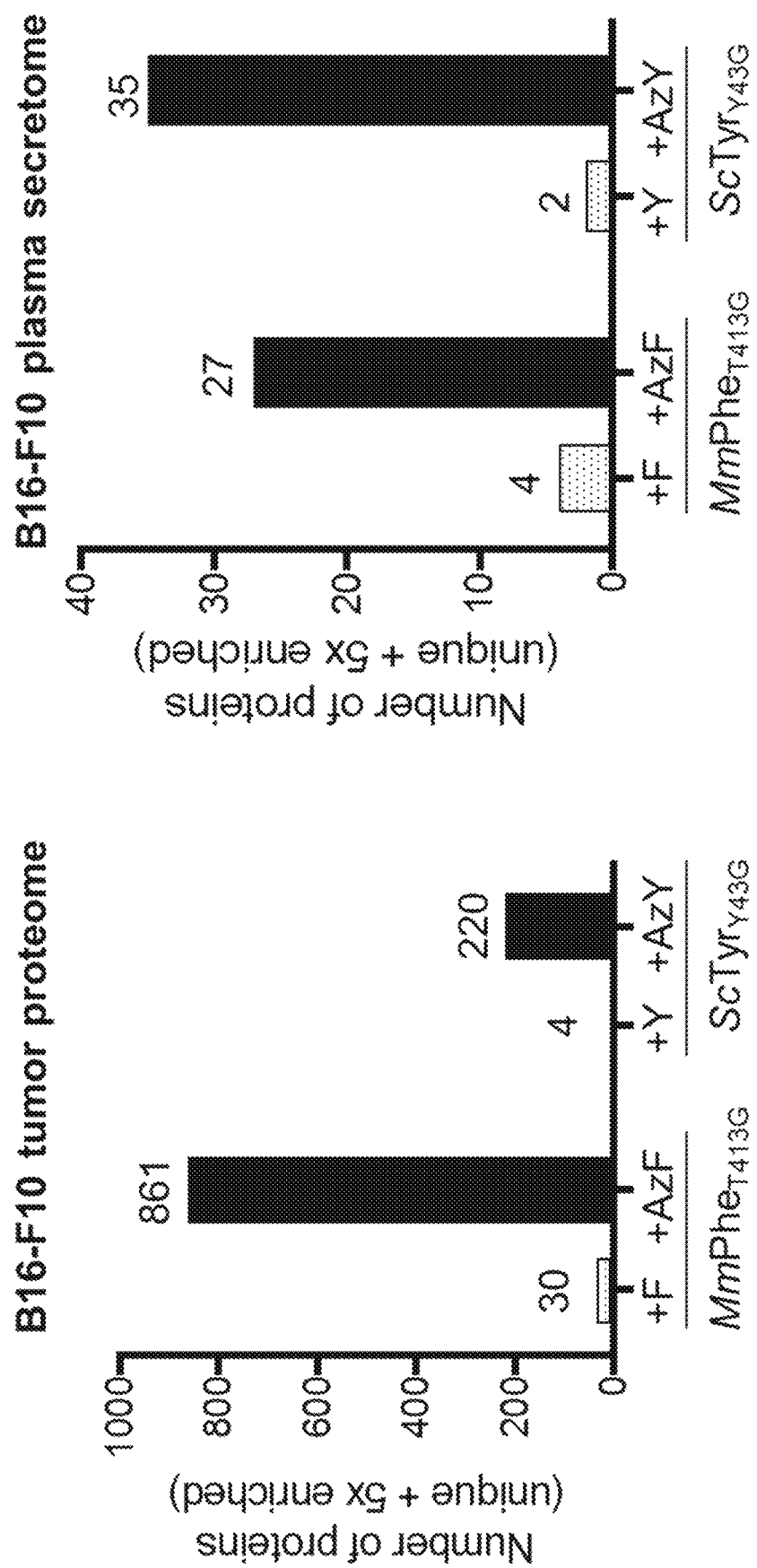
FIG. 16: Enrichment of AzF- and AzY-incorporated B16-F10 melanoma proteomes and secretomes over nonspecific background (tumors exposed only to canonical Phe or Tyr amino acids). Melanoma cells stably expressed MmPhe$_{T413G}$ or ScTyr$_{Y43G}$. Melanoma lysate and secreted proteins are enriched via DBCO affinity purification in tumors exposed to azido-bearing AzF and AzY compared to those exposed to canonical Phe or Tyr.
Figure 18:
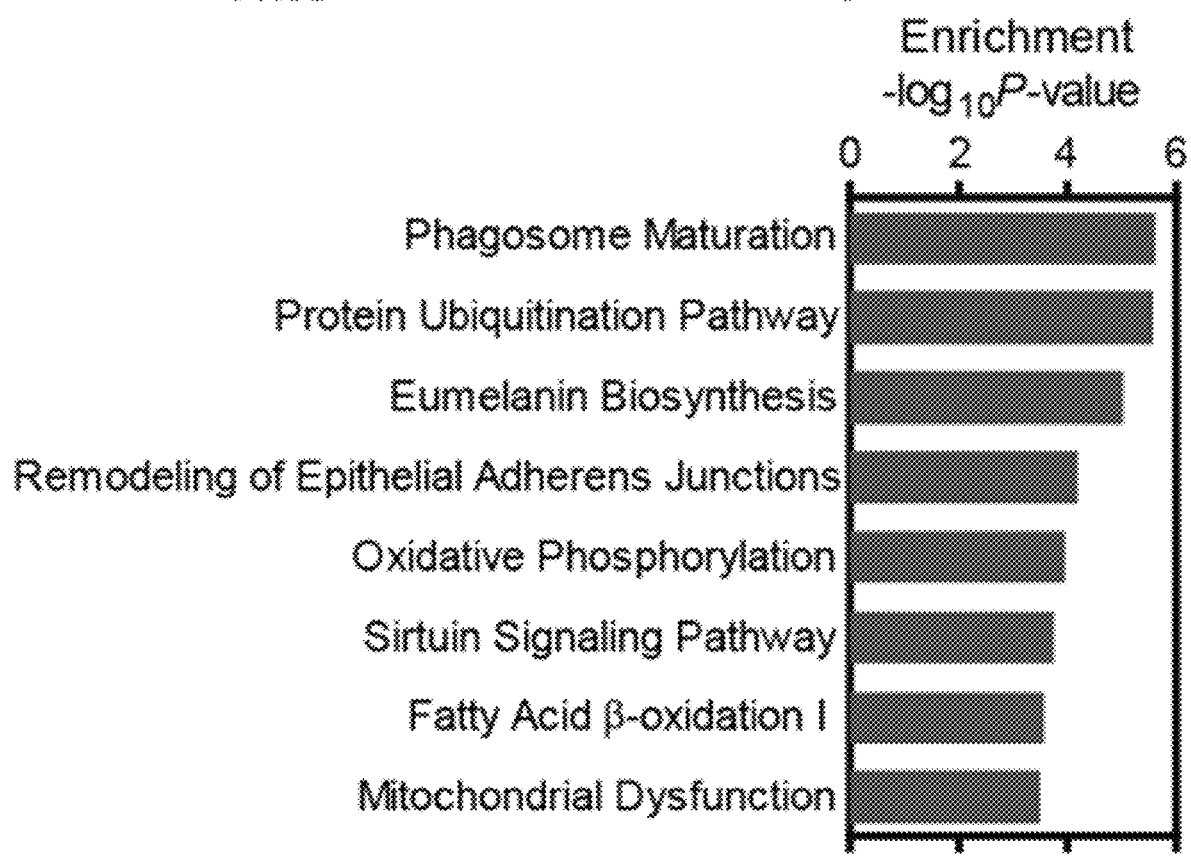
FIG. 18: Ingenuity Pathway Analysis (Qiagen). The top canonical pathways enriched in the labeled melanoma tumor proteome and secretome by MmPhe$_{T413G}$ and ScTyr$_{Y43G}$.
Figure 18:
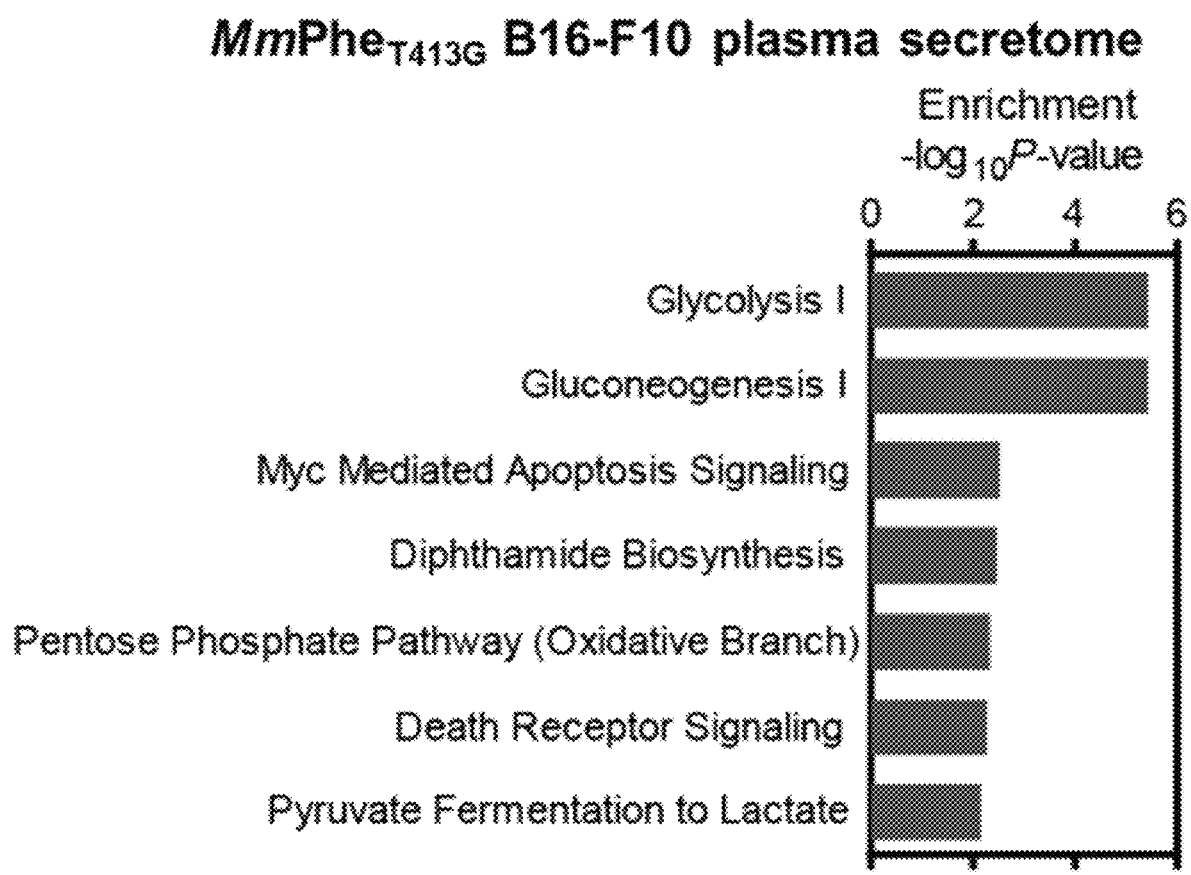
Figure 18:
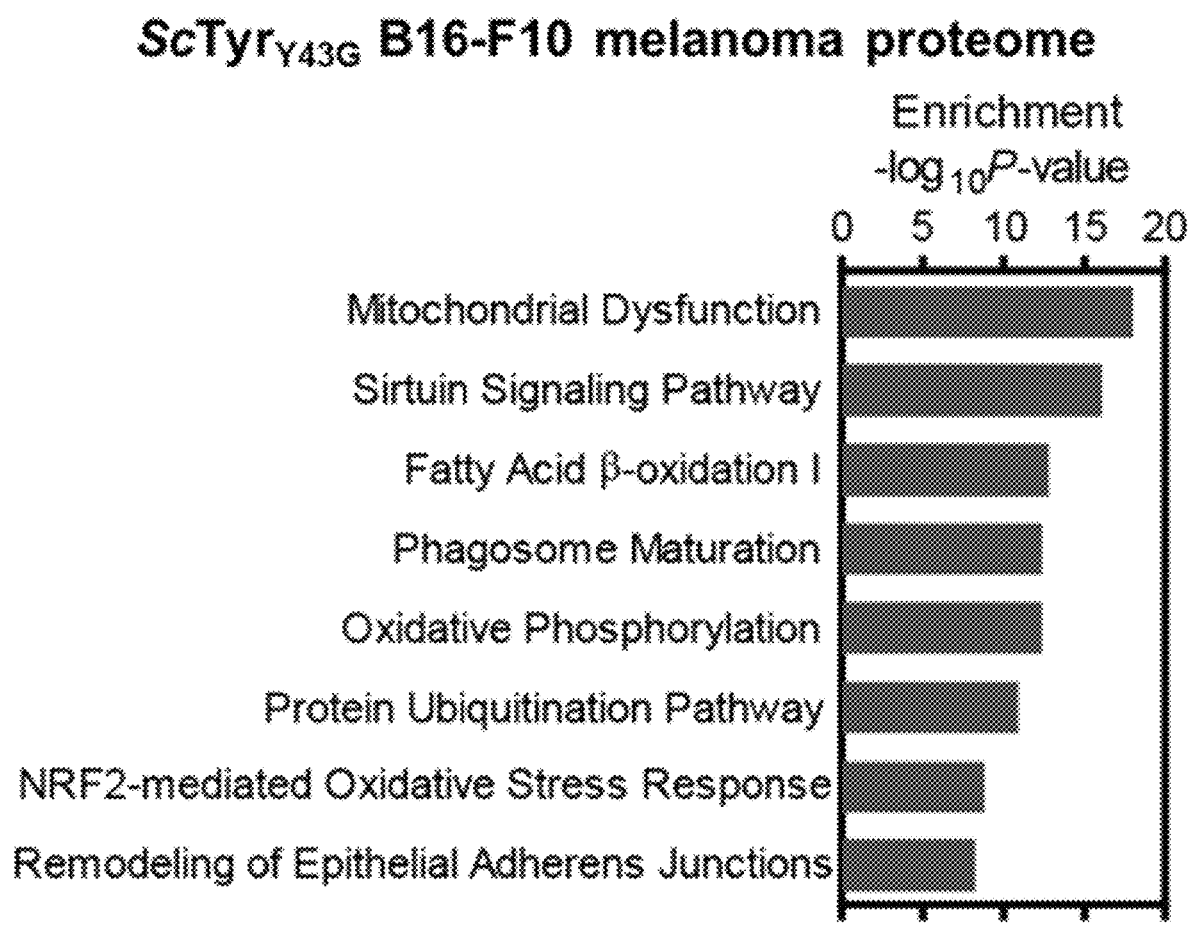
Figure 18:
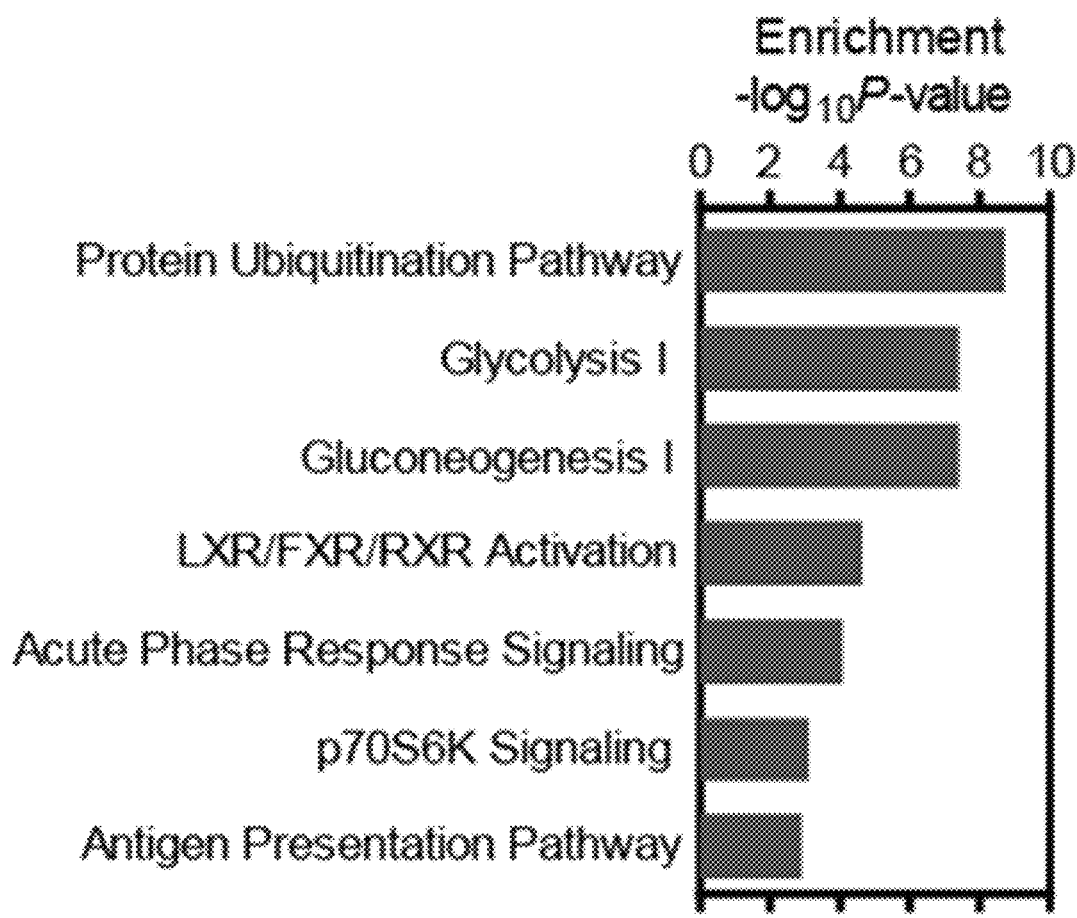
Figure 19A:
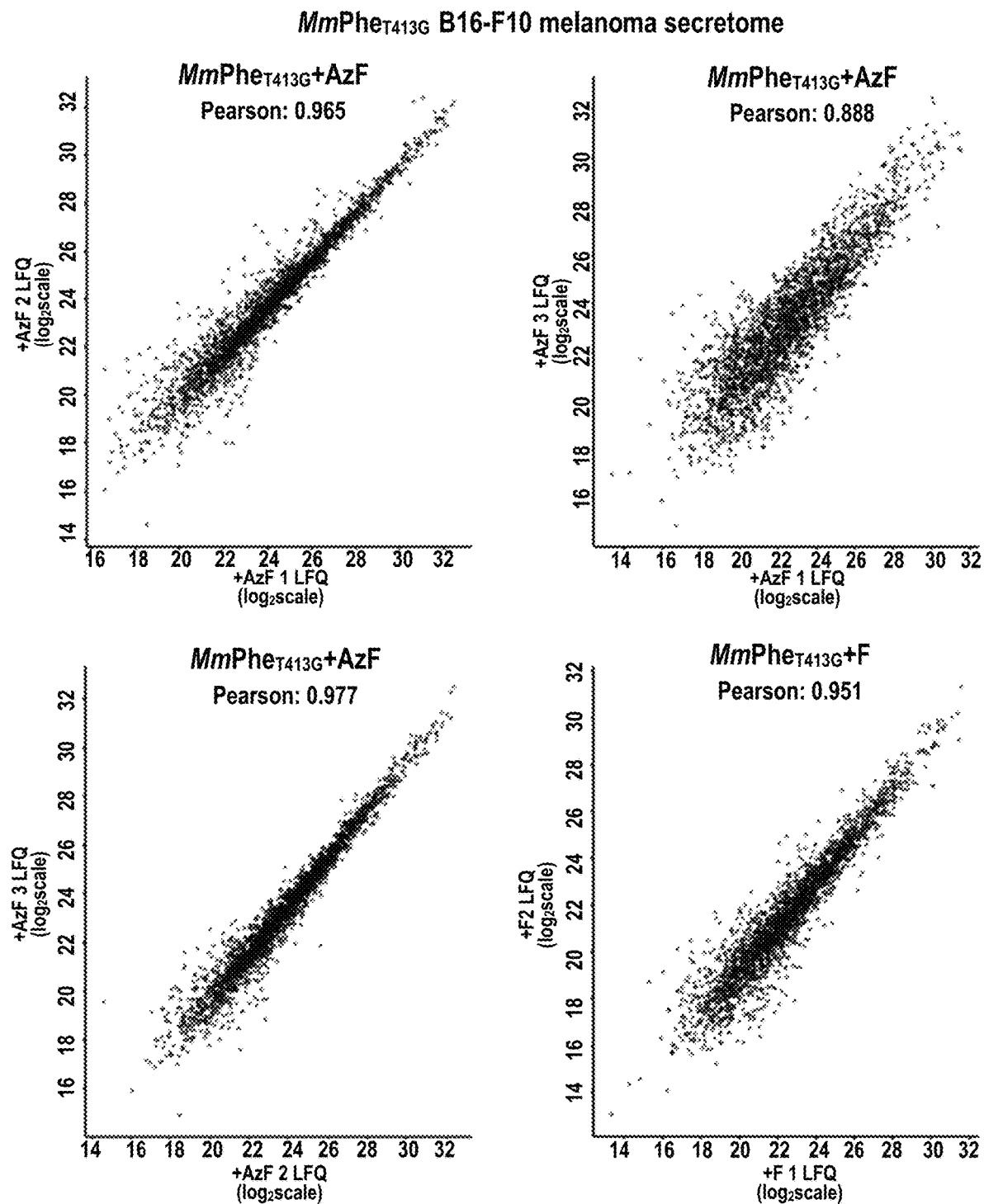
FIGS. 19A and 19B: Low variability across B16-F10 in vivo labeled proteomes. Reproducibility between biological replicates was assessed based on Proteome Discoverer's label-free quantification values across proteins detected in all replicates. Pearson correlation coefficients are displayed per replica pairwise comparison.
Figure 19B:
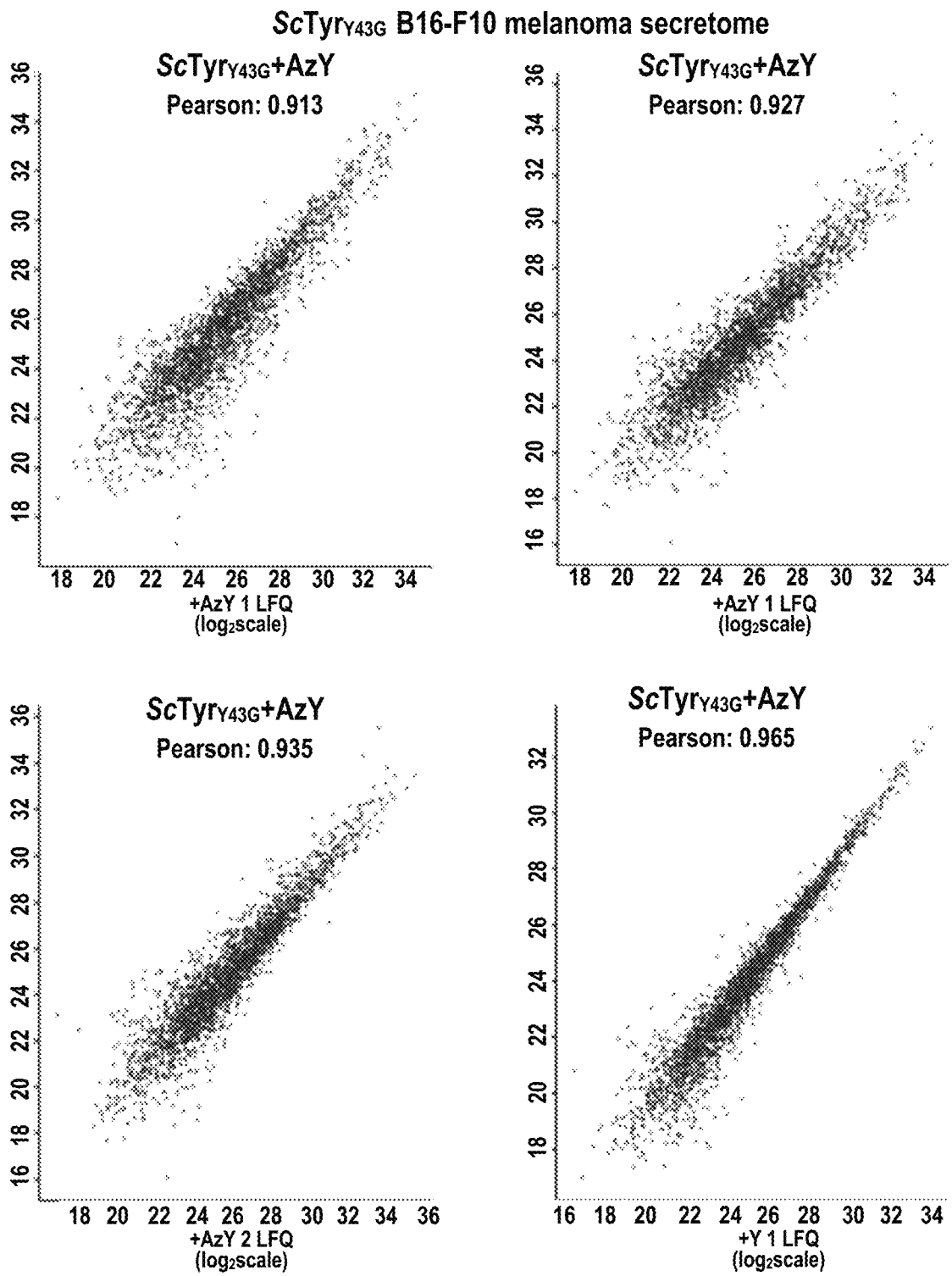
Figure 20A:
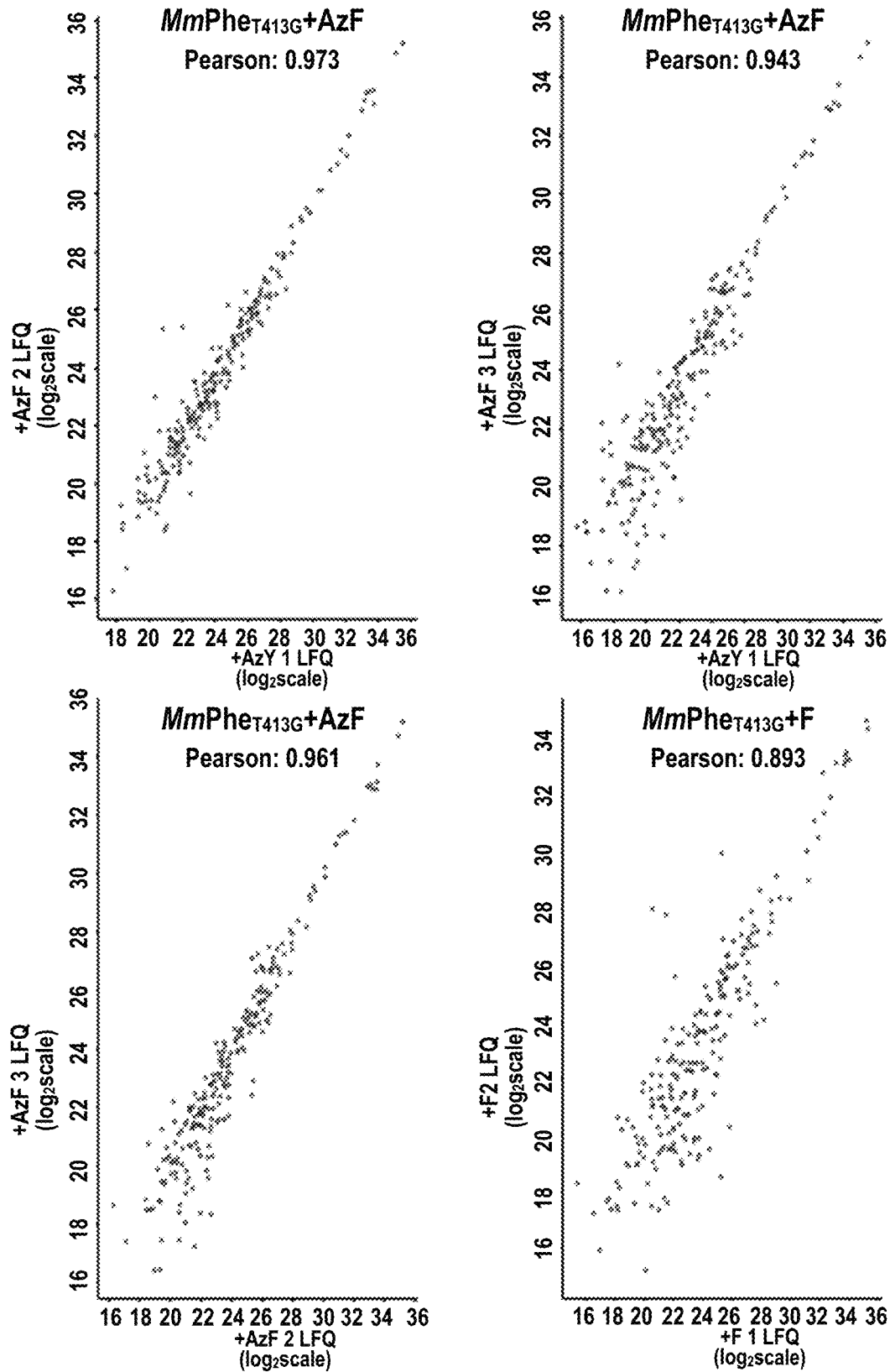
FIGS. 20A and 20B: Low variability across B16-F10 in vivo labeled secretomes. Reproducibility between biological replicates was assessed based on Proteome Discoverer's label-free quantification values across proteins detected in all replicates. Pearson correlation coefficients are displayed per replica pairwise comparison.
Figure 20B:
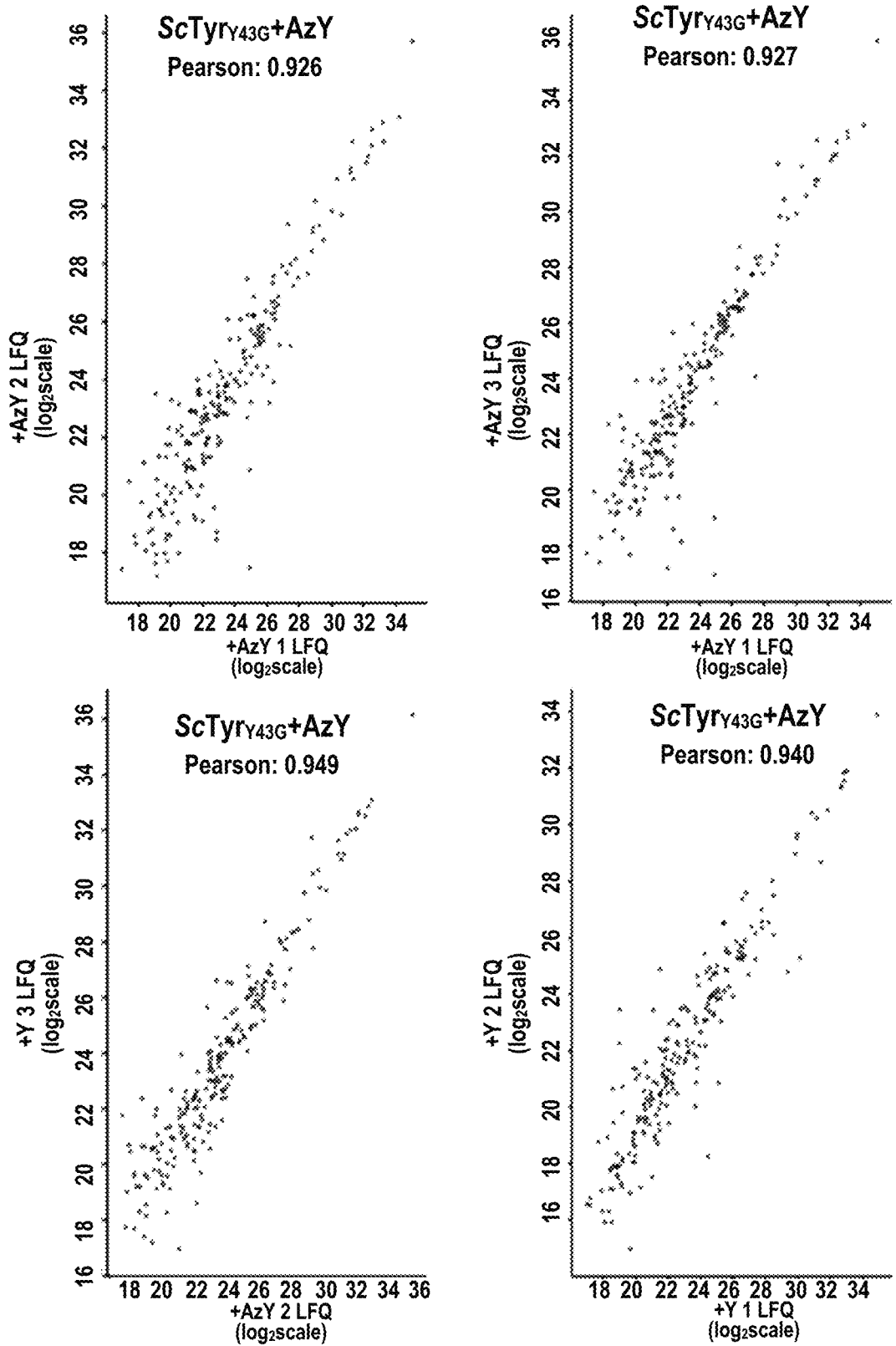

We next sought to identify the labeled melanoma proteome. Tumor cell lysates were collected, 3 mg incubated with DBCO beads, and processed for label-free mass spectrometric characterization. As in HEK293T cells, MmPhe$_{T413G}$ and ScTyr$_{Y43G}$ labeled distinct B16-F10 tumor proteins in vivo (FIGS. 5C and 16). Though ScTyr$_{Y43G}$ yielded fewer proteins in total, it identified 108 proteins MmPhe$_{T413G}$ did not, further evidence of mutant aaRSs labeling preferred proteome subsets. For both mutant aaRSs, proteins were detected across a wide variety of cellular components, spanning the nucleus, mitochondria, and cell surface (FIGS. 5D and 17). Labeled proteomes were significantly enriched for canonical pathways implicated in tumor progression, metabolism, and apoptosis (FIGS. 5E and 18) (26,27). Despite the rapid adoption of MmMet$_{L274G}$ in vivo, to our knowledge, cell-type-specific secretome labeling has not yet been demonstrated. We click-enriched 3 mg of plasma from tumor-bearing mice for mass spectrometry, finding that MmPhe$_{T413G}$ and ScTyr$_{Y43G}$ labeled distinct subsets of the tumor plasma secretome. Surprisingly, secretome labeling was comparable (FIGS. 5F and 16). This may arise from several factors, such as tyrosine's greater solvent accessibility; but does not correlate with the relative abundance of tyrosine to phenylalanine in the mouse secretome (UniProt: 3.6% Phe vs 2.9% Tyr in frequency), consistent with prior work (17). Several labeled secretome proteins, including the 14-3-3 family of proteins and proteasome subunits, have been validated in human cancer xenograft studies, but many are novel (28,29). Like the labeled tumor proteome, the secretome was enriched for pathways implicated in cancer, including glycolysis, ubiquitination, and pentose phosphate pathway signaling (FIGS. 5G and 18) (30-32). Unlike prior studies, cell-type-specific bioorthogonal labeling via mutant aaRSs can distinguish tumor- and host-secreted plasma proteins across a wide variety of immunocompetent mouse models. We report a list of B16-F10 melanoma secreted plasma proteins, to be expanded upon in dedicated, follow-up biological studies (Table 1).

In summary, we find that ScTyr$_{Y43G}$ and MmPhe$_{T413G}$ label proteins across mammalian cell lines and in live mice. These mutant aaRSs demonstrate high selectivity for activating AzY and AzF over endogenous Tyr and Phe, respectively. ScTyr$_{Y43G}$ and MmPhe$_{T413G}$ label overlapping but distinct proteomes in HEK293T cells, and their co-expression yields a fuller proteome. ScTyr$_{Y43G}$ and MmPhe$_{T413G}$ enable a first application of bioorthogonal labeling to a tumor model in mice and to the identification of plasma factors secreted from specific cell types.

Interest in adopting bioorthogonal labeling tools for cell- and tissue-specific proteomics in mammals is growing (16, 33, 34). We suggest that targeted co-expression of ScTyr$_{Y43G}$ and MmPhe$_{T413G}$ alongside the existing MmMet$_{L274G}$ via 2A or IRES elements may enhance cell-specific proteome coverage and confidence, and capture a hitherto undetected richness in proteome spatial and temporal dynamics. Multiple engineered synthetases enable the multiplexed incorporation of diverse chemistries into a given mammalian proteome or the simultaneous labeling of different cell types in mice. This work also informs the engineering of additional mutant aaRSs for mammalian proteomics, as the three mutant aaRSs were consistently developed by expanding their amino acid binding pockets via single substitutions to glycine. And as aryl azides, proteome-incorporated AzY and AzF could be used as photo-crosslinkers to investigate protein interactions (20,24), with other compatible ncAAs introducing additional chemistries. In general, ScTyr$_{Y43G}$ and MmPhe$_{T413G}$ open new opportunities for in vivo cataloguing, tracking, and modulation of proteomes from specific mammalian cells.

Materials and Methods

Cloning of synthetase variants into mammalian vectors. Mouse or human codon-optimized variants of ScTyr$_{Y43G}$ (SEQ ID NO:1), MmPhe$_{T413G}$ (SEQ ID NO:2), and wild-type PheRS (SEQ ID NOS:10 and 11) were ordered as gBlocks (IDT), with NheI and EcoRI restriction sites in the N- and C-terminus, respectively. gBlock sequences were PCR amplified, cleaned, and digested with NheI and EcoRI before insertion into the multiple cloning site of the Piggybac vector PB513B-1 (SBI). The CP1 switch construct was created by replacing the E. coli TyRS CP1 domain (amino acids 385-583) with that of the human TyRS, and cloned into PB513B-1 (35). In this vector, the inserted transgene is driven by the CMV promoter, with GFP and puromycin gene expressed via an EF1α promoter. The MjTyRS construct was obtained via PCR of the synthetase from the pEVOL-pAzF plasmid (Addgene), and cloned into PB513B-1. We used Stable Competent E. coli (NEB) for transformations, 100 µg/ml ampicillin for colony selection, and the HiSpeed Plasmid Maxi Kit (Qiagen) for DNA purification.

Cell culture. HEK293T and B16-F10 cells were cultured in DMEM (Invitrogen) medium with 10% fetal bovine serum (FBS). CHO-K1 cells were cultured in Ham's F-12K Medium (Kaighn's, Thermo) medium with 10% fetal bovine serum. All cells were passaged every two to three days on tissue-culture plates, incubating at 37° C. and 5% CO2, and discarded before reaching passage 18.

Cell transfection, click amino acid labeling, and selection of stably transfected B16-F10 cells. Unless otherwise noted, cells were transiently transfected with Lipofectamine 3000 (Invitrogen) 24 hours prior to 4-Azido-L-phenylalanine (AzF, Chem-Implex) or 3-Azido-L-tyrosine (AzY, Watanabe Chemical Industries) labeling. For initial assessment of labeling across mammalian cell lines, transfected cells were incubated with 2 mM of AzF, AzY, tyrosine, or phenylalanine for 30 hours in 12-well plates prior to lysis. To characterize enzyme selectivity and rate of substrate activation, transfected HEK293T cells were incubated with varying amounts of endogenous and non-canonical amino acids for 24 hours in 12-well plates prior to lysis. For affinity enrichment prior to shotgun mass spectrometry, transfected HEK293T cells were incubated with 125 µM of endogenous and non-canonical amino acids for 24 hours in 10 cm dishes prior to lysis. B16-F10 cells were transfected with mutant synthetases in the Piggybac vector PB513B-1 for 72 hours prior to puromycin selection at 10 µg/ml for 10 days.

Copper-free reaction of DIBO-Alexa Fluor 647 with click-labeled cell lysates for in-gel fluorescence. After washing in PBS twice, cells were lysed 1% SDS in PBS with EDTA-free protease inhibitor (Roche). Lysates were sonicated with a tip sonicator to reduce sample viscosity before centrifugation at 14,000 g for 20 minutes at 4° C. The supernatant was collected and kept at −80° C. for long-term storage. Protein concentrations were measured with a BCA Protein Assay Kit (Pierce) to ensure equal loading across gel wells (~23 µg). Lysates were alkylated with 6 mM iodoacetamide (Pierce) for 45 minutes in the dark at room temperature, before the copper-free click reaction with DIBO-Alexa Fluor 647 (Thermo) for 90 minutes in the dark at room temperature. A 4× stock solution of NuPAGE LDS (Thermo) and 8% (v/v) 2-mercaptoethanol (Sigma) was added to each sample before heating at 95° C. Proteins were briefly spun and separated by electrophoresis in 12% Bis-Tris polyacrylamide gels (Invitrogen). Gels were washed twice in distilled water for 10 minutes before Alexa Fluor 647 imaging in the 700-nm channel of an Odyssey CLx (LI-COR). To assess protein loading, gels were incubated with GelCode Blue Stain Reagent (Thermo) overnight before destaining in distilled water for at least 3 hours. Colloidally stained gels were imaged in the 800-nm channel of an Odyssey CLx (LI-COR), where no bleed-through of the Alexa Fluor 647 signal was detected. Quantification of signal intensities of labeled proteomes from each gel lane were analyzed in ImageJ as before, but with slight modifications (36). Specifically, individual lanes were not split into quarters to report intensity mean and standard deviations. Instead, the mean and standard deviations were calculated from biological triplicates of whole gel lanes, less the dye front.

Copper-catalyzed reaction of alkyne-Alexa Fluor 647 for microscopy. 10 hours after transfection, adherent HEK293T cells were plated onto glass bottom tissue culture plates (MatTek) and chambered coverglass (Nunc™ Lab-Tek™ Thermo) coated with CELLstart (Thermo). After another 20 hours, adherent cells were incubated with 125 µM of endogenous or non-canonical amino acids for 12 hours. Cells were washed twice with PBS, fixed with 4% paraformaldehyde (VWR) for 15 minutes at room temperature, washed with PBS twice more, permeabilized with 0.1% Triton X-100 for 2 minutes at room temperature, and washed three times for 5 minutes each with PBS. Labeling was performed at room temperature for 2.5 hours in PBS with a final concentration of 0.1 mM copper sulfate, 0.5 mM THPTA (Click Chemistry Tools), 5 mM sodium ascorbate, 5 mM aminoguanidine and 10 µM alkyne-Alexa Fluor 647 (Thermo). Cells were washed five times for 5 minutes each before leaving in PBS overnight shaking at 4° C. Cells were then incubated with Hoechst 33342 Solution (Thermo) for 15 minutes to stain nuclei, washed three times with PBS for 5 minutes each, and mounted with ProLong Gold Antifade Mountant (Thermo). Fluorescence confocal images were obtained on a Zeiss LSM 880 microscope and KEYENCE BZ-X700 for quantification.

For imaging of B16-F10 in vivo melanoma slices, tumors were fixed for 48 hours in 4% paraformaldehyde before being embedded in 5% low-melt agarose (Sigma) and vibratome sectioned in PBS. Slices were blocked and permeabilized for 30 minutes in 6% BSA and 0.2% Triton X-100 before three washes in 1% BSA in PBS. Copper-click labeling, Hoechst staining, and mounting was performed as above before imaging on a Zeiss LSM 700 microscope.

Copper-free reaction of DIBO-Alexa Fluor 647 for flow cytometry. 30 hours after transfection, adherent HEK293T cells were incubated with 125 µM of endogenous or non-canonical amino acids for 16 hours. Cells were then suspended, washed twice with PBS, and incubated with LIVE/DEAD™ Fixable Violet Dead Cell Stain (Thermo), per manufacturer's instructions. Cells were washed once with PBS, fixed with 4% paraformaldehyde for 15 minutes at room temperature, washed three times with 1% FBS in PBS, and alkylated with 10 mM iodoacetamide in 1% FBS for 30 minutes in the dark at room temperature. Cells were then reacted with 6 µM DIBO-Alexa Fluor 647 for 2 hours. Cells were washed three times with 1% FBS in PBS and left in 1% FBS solution overnight shaking at 4° C. After a final wash in 1% FBS, cells were filtered through a 35 µM nylon mesh (Corning). Flow cytometry was performed using an LSR-Fortessa (BD), with only live/dead-discriminated, single cells kept for analysis in FlowJo 10. DIBO 647+ cells were live/dead-discriminated, singlets with Alexa Fluor 647 signal (a.u.) greater than $3*10^3$.

Affinity enrichment of AzF- or AzY-labeled proteins for mass spectrometry. Transfected HEK293T cells were incubated with 125 M of endogenous and non-canonical amino acids for 24 hours in triplicate 10 cm dishes prior to PBS washes and lysis. Endogenous amino acid samples were used to estimate the degree of non-specific enrichment. Cells were lysed in a solution of 1% SDS, 8 M urea, 1 M NaCl, 100 mM chloroacetamide, 20 mM iodoacetamide, and EDTA-free protease inhibitor (Roche). Lysates were sonicated with a tip sonicator to reduce sample viscosity before centrifugation at 14,000 g for 20 minutes at 4° C. After ensuring uniform protein concentrations (3 mg of lysates) via BCA assay (Pierce), samples were pre-cleared with pre-washed 6% BCL agarose beads (ABT) for 90 minutes, rotating in the dark. Agarose beads were pre-washed three times with 0.8% SDS in PBS. Lysates were removed from plain agarose beads and each added to 50 µL of similarly pre-washed azadibenzocyclooctyne (DBCO) resin (50% slurry by volume; Click Chemistry Tools). The copper-free cycloaddition proceeded rotating, overnight, in the dark, at room temperature. As before, unreacted DBCO groups were quenched by the addition of 100 mM Anl for 30 minutes (2 mM final concentration) (37). Supernatant was removed, beads washed with at least 1 mL of $H_2O$, reduced with 1 mL DTT (1 mM, 15 minutes at 70° C. with occasional vortexing), and alkylated with 1 mL iodoacetamide (40 mM, 30 minutes at room temperature, in the dark). Beads were then washed with greater than 50 mL each of 0.8% SDS in PBS, 8 M urea in 100 mM Tris (pH 8), and 20% acetonitrile. The resin was resuspended in 1 mL of 50 mM HEPES and transferred to an eppendorf tube. After centrifugation at 1,000 g for 5 minutes and removal of ~750 uL of supernatant, 1 µg of Mass Spec Grade Trypsin/Lys-C Mix was added to each sample (Promega). Samples were digested overnight at 37° C., the beads spun, and supernatant collected.

Mass spectrometry. Peptides eluted from DBCO enrichment of HEK293T cell lysates were labelled with 10-plex Tandem Mass Tags (TMT) (Thermo Scientific) per manufacturer's instructions. A global standard was created by taking an equal aliquot of each peptide sample and included in each 10-plex. A subset of each sample and the standard was removed to check reporter ion distributions and TMT labeling efficiency. The remainder were mixed with the adjusted ratio, dried down, resuspended in 0.1% formic acid, cleaned using C18-based STAGE Tips, lyophilized, and stored at −80° C. until final LC-MS/MS measurement (38, 39). Peptides were analyzed on an LTQ Orbitrap Fusion Tribrid Mass Spectrometer (Thermo Scientific). Peptides were separated by capillary reverse-phase chromatography on a 24 cm reversed-phase column (100 µm inner diameter, packed in-house with ReproSil-Pur C18-AQ 3.0 m resin (Dr. Maisch)) over a total run time of 180 min using a four-step linear gradient via an Dionex Ultimate 3000 LC-system (Thermo Scientific): 97% A (and 3% B) to 96% A in 15 min, to 75% A in 135 min, to 55% A in 15 min, and then to 5% A in 15 min, where buffer A is 0.1% formic acid in water; buffer B is 0.1% formic acid in acetonitrile. Acquisition was performed in data-dependent mode with the full MS scans acquired in the Orbitrap mass analyzer with a resolution of 120,000 and m/z scan range 400-1,500. The AGC targets were $4*10^5$ and the maximum injection time for FTMS (35) were 50 ms. The most intense ions were then selected in top speed mode for sequencing using collision-induced dissociation (CID) and the fragments were analyzed in the ion trap. The normalized collision energy for CID was 35% at 0.25 activation Q. The AGC targets were $1*10^4$ and the maximum injection time for $MS^2$ were 30 ms. Monoisotopic precursor selection and charge state rejection were enabled. Singly charged ion species and ions with no unassigned charge states were excluded from MS2 analysis. Ions within ±10 ppm m/z window around ions selected for MS2 were excluded from further selection for fragmentation for 90 s. Following each MS2 analysis, five most intense fragment ions were selected simultaneously for HCD MS3 analysis with isolation width of 1.2 m/z, normalized collision energy of 65% at resolution of 60,000, AGC target were 1*10$^5$ and maximum injection time of 90 ms. The raw data files were processed and analyzed using Proteome Discoverer software v2.1 (Thermo). Precursor mass tolerance is set to ±10 ppm and fragment mass tolerance is set to ±0.6 Da. Carbamidomethylation of cysteine (+57.021 Da), TMT-labeled N-terminus and lysine (+229.163) were set as static modifications. Differential modifications were: oxidation of methionine (+15.995 Da), phosphorylation of serine, tyrosine and threonine (+79.9663), acetylation of protein N-terminal (+42.011 Da). Proteome Discoverer searched the spectra against the Uniprot Human database (June 2016) including common contaminants using the SEQUEST algorithm (40). Percolator was applied to filter out the false MS2 assignments at a strict false discovery rate of 1% at both the peptide and protein level (41). For quantification, a mass tolerance of ±20 ppm window was applied to the integration of report ions using the most confident centroid method. Protein abundance was estimated by taking the average abundance of the top 3 peptides mapped to that protein.

For data preprocessing of TMT-labeled samples, the mean of two technical replicates was used for each biological replicate. Intensities were normalized to the global TMT standard. Statistical analysis was performed on 1539 proteins with signal in at least one sample. Because missing data must be imputed for principal component analysis (PCA), missing data for each protein were imputed conservatively by taking the lowest value across replicates where data was present and dividing by 2. Normed PCA was performed using the R ade4 package (42). For differential expression analysis, non-imputed data was compared between groups using the Welch Two Sample t-test, when n≥2 in each group. The venn diagram represents the number of significantly detectable proteins (p<0.05) with |log$_2$(FC)|>1. Volcano plots represent the pairwise comparison of hits between mutants; or in FIG. 10, between ncAA-fed and canonical amino acid-fed conditions. The heatmap represents genes significantly detectable by at least one mutant (p<0.05).

For enriched in vivo melanoma and plasma samples, peptides were prepared as above, excluding TMT-specific adaptations, and analyzed on an LTQ Orbitrap Elite mass spectrometer (Thermo Fisher Scientific). Samples were separated by capillary reverse-phase chromatography on a 24-cm reversed-phase column (100 µm inner diameter, packed in-house with ReproSil-Pur C18-AQ 3.0 m resin (Dr. Maisch)) over a total run time of 160 min using a two-step linear gradient with 4-25% buffer B (0.2% (v/v) formic acid, 5% DMSO, and 94.8% (v/v) acetonitrile) for 120 min followed by 25-40% buffer B for 30 min using an Eksigent ekspert nanoLC-425 system (SCIEX, Framingham, Mass., USA). Acquisition was executed in data-dependent mode with the full MS scans acquired in the Orbitrap mass analyser with a resolution of 60,000 and m/z scan range 340-1,600. The top 20 most abundant ions with intensity threshold above 500 counts and charge states 2 and above were selected for fragmentation using collision-induced dissociation (CID) with isolation window of 2 m/z, collision energy of 35%, activation Q of 0.25 and activation time of 5 ms. The CID fragments were analyzed in the ion trap with rapid scan rate. Dynamic exclusion was enabled with repeat count of 1 and exclusion duration of 30 s. The AGC target was set to 1*10$^6$ and 5000 for full FTMS scans and ITMSn scans. The maximum injection time was set to 250 s and 100 s for full FTMS scans and ITMSn scans. Data analysis was performed as above using Proteome Discoverer software v2.2 (Thermo), excluding TMT-specific adaptations. Peptide intensities were analyzed with Excel and Perseus (43).

Labeled proteins were identified adopting previous methods (44). Briefly, only proteins detected (1) exclusively in the ScTyr$_{Y43G}$+AzY or MmPhe$_{T413G}$+AzF replicates (and not in ScTyr$_{Y43G}$+Y or MmPhe$_{T413G}$+F control replicates); or (2) found across all replicates and ≥5 times enriched in the ScTyr$_{Y43G}$+AzY or MmPhe$_{T413G}$+AzF replicates were considered labeled. Labeled proteins were annotated using STRAP and Ingenuity Pathway Analysis (Qiagen) software (45,46).

Codon usage analysis. To determine whether ScTyr$_{Y43G}$ and MmPhe$_{T413G}$ are capable of labeling via both of their cognate codons (TAT and TAC for ScTyr$_{Y43G}$; and TTT and TTC for MmPhe$_{T413G}$), cDNA sequences of TMT-quantified HEK293T proteins were retrieved via the Ensembl human genome database (Human release 92). cDNA sequences were parsed into codon triplets and the number of the four aforementioned codons counted for each protein. Proteins with exclusively one of the two tyrosine or phenylalanine codons (e.g., TAT only) were mapped against proteins significantly enriched by ScTyr$_{Y43G}$+AzY and MmPhe$_{T413G}$+AzF. This yielded a list of proteins that were labeled by ScTyr$_{Y43G}$ or MmPhe$_{T413G}$ uniquely via that codon. To assess whether labeling was preferential between cognate codons, codon fractions of significantly enriched proteins were compared with the codon fractions of all TMT-identified proteins.

Animals and B16-F10 melanoma tumor model. Female C57BL/6 mice were purchased from Charles River and kept on a 12-h light/dark cycle and provided access to food and water ad libitum. All animal procedures complied with the Animal Welfare Act and were in accordance with institutional guidelines by the V.A. Palo Alto Committee on Animal Research and the institutional administrative panel of laboratory animal care at Stanford University. Stably transfected B16-F10 cells were suspended, washed in PBS twice, and checked for viability with trypan blue. Only cells with viabilities greater than 90% were considered for subsequent subcutaneous injection. Cells were filtered through a 100 µM strainer (Fisher), spun, and resuspended in DMEM at 10$^7$ cells/ml. 100 µL of cells (10$^6$ cells) were subcutaneously injected into the right hind limb of 12-week-old female mice. Animals were monitored for palpable tumor starting at 10 days after injection. 16 days post-injections, mice were administered 1 mmol/kg of amino acid intraperitoneally and intratumorally. Intratumoral injection volumes of 25 mM stock solution were $\frac{1}{5}^{th}$ of the caliper-measured tumor volume $$V = \frac{W^2 L}{2},$$

where W is tumor width and L is tumor length. On days 18-19, mice were anesthetized with 2.5% (v/v) avertin. Blood was collected with EDTA as anticoagulant by terminal intracardial bleeding. EDTA-plasma was isolated by centrifugation at 1,000 g for 15 min at 4° C. before aliquoting, flash freezing, and storage at −80° C. Tumors were excised, and the majority minced and filtered through a 100 µM strainer. Tumor cells were washed 3× in PBS via centrifugation at 500 g for 10 min at 4° C. before flash freezing and storage at −80° C. For affinity enrichment and mass spectrometry, approximately 3 mg of tumor lysates and plasma were prepared as indicated above. Remaining tumor tissue was immersion fixed in 4% PFA for imaging.

TABLE 1

Labeled proteins secreted from B16-F10 melanomas into the plasma in FIG. 5F.

| Protein name | Gene | Uniprot ID | Identifying aaRS | Function | Catalytic Activity |
|---|---|---|---|---|---|
| 14-3-3 protein gamma | Ywhag | P61982 | ScTyr$_{Y43G}$ | Adapter protein implicated in the regulation of a large spectrum of both general and specialized signaling pathways. | |
| 14-3-3 protein theta | Ywhaq | P68254 | MmPhe$_{T413G}$ | Adapter protein implicated in the regulation of a large spectrum of both general and specialized signaling pathways. Negatively regulates the kinase activity of PDPK1 (By similarity). | |
| 5,6-dihydroxyindole-2-carboxylic acid oxidase | Tyrp1 | P07147 | MmPhe$_{T413G}$ | Catalyzes the oxidation of 5,6-dihydroxyindole-2-carboxylic acid (DHICA) into indole-5,6-quinone-2-carboxylic acid (PubMed: 7813420). | |
| 6-phosphogluconate dehydrogenase, decarboxylating | Pgd | Q9DCD0 | MmPhe$_{T413G}$ | Catalyzes the oxidative decarboxylation of 6-phosphogluconate to ribulose 5-phosphate and CO(2), with concomitant reduction of NADP to NADPH. | 6-phospho-D-gluconate + NADP(+) = D-ribulose 5-phosphate + CO(2) + NADPH. |
| 78 kDa glucose-regulated protein | Hspa5 | P20029 | ScTyr$_{Y43G}$ | Plays a role in facilitating the assembly of multimeric protein complexes inside the endoplasmic reticulum (PubMed: 12475965). | |
| Actin, alpha cardiac muscle 1 | Actc1 | P68033 | Both | Actins are highly conserved proteins that are involved in various types of cell motility and are ubiquitously expressed in all eukaryotic cells. | |
| Alpha-1-antitrypsin 1-1 | Serpina1a | P07758 | ScTyr$_{Y43G}$ | Inhibitor of serine proteases. | |
| Alpha-1-antitrypsin 1-2 | Serpina1b | P22599 | ScTyr$_{Y43G}$ | Inhibitor of serine proteases. | |
| Alpha-1-antitrypsin 1-4 | Serpina1d | Q00897 | ScTyr$_{Y43G}$ | Inhibitor of serine proteases. | |
| Alpha-1-antitrypsin 1-5 | Serpina1e | Q00898 | ScTyr$_{Y43G}$ | Does not inhibit elastase or chymotwpsin. | |
| Alpha-enolase | Eno1 | P17182 | ScTyr$_{Y43G}$ | Multifunctional enzyme that, as well as its role in glycolysis, plays a part in various processes such as growth control, hypoxia tolerance and allergic responses (By similarity). | 2-phospho-D-glycerate = phosphoenolpyruvate + H(2)O. |
| Angiotensinogen | Agt | P11859 | ScTyr$_{Y43G}$ | Essential component of the renin-angiotensin system (RAS), a potent regulator of blood pressure, body fluid and electrolyte homeostasis. | |
| Antithrombin-III | Serpinc1 | P32261 | MmPhe$_{T413G}$ | Most important serine protease inhibitor in plasma that regulates the blood coagulation cascade. | |

TABLE 1-continued

Labeled proteins secreted from B16-F10 melanomas into the plasma in FIG. 5F.

| Protein name | Gene | Uniprot ID | Identifying aaRS | Function | Catalytic Activity |
|---|---|---|---|---|---|
| Aspartyl aminopeptidase | Dnpep | Q9Z2W0 | ScTyr$_{Y43G}$ | Aminopeptidase with specificity towards an acidic amino acid at the N-terminus. | Release of an N-terminal aspartate or glutamate from a peptide, with a preference for aspartate. |
| Carboxypeptidase N subunit 2 | Cpn2 | Q9DBB9 | MmPhe$_{T413G}$ | The 83 kDa subunit binds and stabilizes the catalytic subunit at 37 degrees Celsius and keeps it in circulation. | |
| Complement C2 | C2 | P21180 | MmPhe$_{T413G}$ | Component C2 which is part of the classical pathway of the complement system is cleaved by activated factor C1 into two fragments: C2b and C2a. | Selective cleavage of Arg-l-Ser bond in complement component C3 alpha-chain to form C3a and C3b, and Arg-l-Xaa bond in complement component C5 alpha-chain to form C5a and C5b. |
| Cytochrome c, somatic | Cycs | P62897 | MmPhe$_{T413G}$ | Plays a role in apoptosis. | |
| Elongation factor 1-alpha 1 | Eef1a1 | P10126 | ScTyr$_{Y43G}$ | This protein promotes the GTP-dependent binding of aminoacyl-tRNA to the A-site of ribosomes during protein biosynthesis. | |
| Elongation factor 2 | Eef2 | P58252 | Both | Catalyzes the GTP-dependent ribosomal translocation step during translation elongation. | |
| Fibulin-1 | Fbln1 | Q08879 | MmPhe$_{T413G}$ | Incorporated into fibronectin-containing matrix fibers. | |
| Fibulin-5 | Fbln5 | Q9WVH9 | MmPhe$_{T413G}$ | Essential for elastic fiber formation, is involved in the assembly of continuous elastin (ELN) polymer and promotes the interaction of microfibrils and ELN (By similarity). | |
| Glycerol-3-phosphate phosphatase | Pgp | Q8CHP8 | ScTyr$_{Y43G}$ | Glycerol-3-phosphate phosphatase hydrolyzing glycerol-3-phosphate into glycerol. | Glycerol 1-phosphate + H(2)O = glycerol + phosphate. |
| Histidine-rich glycoprotein | Hrg | Q9ESB3 | ScTyr$_{Y43G}$ | Plasma glycoprotein that binds a number of ligands such as heme, heparin, heparan sulfate, thrombospondin, plasminogen, and divalent metal ions. | |
| Histone H4 | Hist1h4a | P62806 | ScTyr$_{Y43G}$ | Core component of nucleosome. | |
| Insulin-degrading enzyme | Ide | Q9JHR7 | MmPhe$_{T413G}$ | Plays a role in the cellular breakdown of insulin, IAPP, glucagon, bradykinin, kallidin and other peptides, and thereby plays a role in intercellular peptide signaling. | Degradation of insulin, glucagon and other polypeptides. No action on proteins. |

TABLE 1-continued

Labeled proteins secreted from B16-F10 melanomas into the plasma in FIG. 5F.

| Protein name | Gene | Uniprot ID | Identifying aaRS | Function | Catalytic Activity |
|---|---|---|---|---|---|
| L-lactate dehydrogenase A chain | Ldha | P06151 | Both | | (S)-lactate + NAD(+) = pyruvate + NADH. |
| Leukotriene A-4 hydrolase | Lta4h | P24527 | Both | Epoxide hydrolase that catalyzes the final step in the biosynthesis of the proinflammatory mediator leukotriene B4. | (7E,9E,11Z,14Z)-(5S,6S)-5,6-epoxyicosa-7,9,11,14-tetraenoate + H(2)O = (6Z,8E,10E,14Z)-(5S,12R)-5,12-dihydroxyicosa-6,8,10,14-tetraenoate. |
| Major urinary protein 2 | Mup2 | P11589 | MmPhe$_{T413G}$ | Binds pheromones that are released from drying urine of males. | |
| Major urinary protein 3 | Mup3 | P04939 | MmPhe$_{T413G}$ | Binds pheromones that are released from drying urine of males. | |
| Malate dehydrogenase, cytoplasmic | Mdh1 | P14152 | MmPhe$_{T413G}$ | | (S)-malate + NAD(+) = oxaloacetate + NADH. |
| NADP-dependent malic enzyme | Me1 | P06801 | Both | | Oxaloacetate = pyruvate + CO(2). |
| Nucleoside diphosphate kinase B | Nme2 | Q01768 | ScTyr$_{Y43G}$ | Major role in the synthesis of nucleoside triphosphates other than ATP. | ATP + protein L-histidine = ADP + protein N-phospho-L-histidine. |
| Peptidyl-prolyl cis-trans isomerase A | Ppia | P17742 | MmPhe$_{T413G}$ | PPIases accelerate the folding of proteins. | Peptidylproline (omega = 180) = peptidylproline (omega = 0). |
| Phosphoglycerate kinase 1 | Pgk1 | P09411 | Both | In addition to its role as a glycolytic enzyme, it seems that PGK-1 acts as a polymerase alpha cofactor protein (primer recognition protein). | ATP + 3-phospho-D-glycerate = ADP + 3-phospho-D-glyceroyl phosphate. |
| Phosphoglycerate mutase 1 | Pgam1 | Q9DBJ1 | ScTyr$_{Y43G}$ | Interconversion of 3-and 2-phosphoglycerate with 2,3-bisphosphoglycerate as the primer of the reaction. | 3-phospho-D-glyceroyl phosphate = 2,3-bisphospho-D-glycerate. |
| Phosphoribosylformylgly cinamidine synthase | Pfas | Q5SUR0 | ScTyr$_{Y43G}$ | Phosphoribosylformylg lycinamidine synthase involved in the purines biosynthetic pathway. | ATP + N(2)-formyl-N(1)-(5-phospho-D-ribosyl) glycinamide + L-glutamine + H(2)O = ADP + phosphate + 2-(formamido)-N(1)-(5-phospho-D-ribosyl) acetamidine + L-glutamate. |
| Proteasome subunit alpha type-1 | Psma1 | Q9R1P4 | Both | Component of the 20S core proteasome complex involved in the proteolytic | Cleavage of peptide bonds with very broad specificity. |

TABLE 1-continued

Labeled proteins secreted from B16-F10 melanomas into the plasma in FIG. 5F.

| Protein name | Gene | Uniprot ID | Identifying aaRS | Function | Catalytic Activity |
|---|---|---|---|---|---|
| Proteasome subunit alpha type-2 | Psma2 | P49722 | Both | Component of the 20S core proteasome complex involved in the proteolytic degradation of most intracellular proteins. | Cleavage of peptide bonds with very broad specificity. |
| Proteasome subunit alpha type-4 | Psma4 | Q9R1P0 | Both | Component of the 20S core proteasome complex involved in the proteolytic degradation of most intracellular proteins. | Cleavage of peptide bonds with very broad specificity. |
| Proteasome subunit beta type-1 | Psmb1 | O09061 | ScTyr$_{Y43G}$ | Component of the 20S core proteasome complex involved in the proteolytic degradation of most intracellular proteins. | Cleavage of peptide bonds with very broad specificity. |
| Proteasome subunit beta type-10 | Psmb10 | O35955 | ScTyr$_{Y43G}$ | The proteasome is a multicatalytic proteinase complex which is characterized by its ability to cleave peptides with Arg, Phe, Tyr, Leu, and Glu adjacent to the leaving group at neutral or slightly basic pH. | Cleavage of peptide bonds with very broad specificity. |
| Proteasome subunit beta type-5 | Psmb 5 | O55234 | ScTyr$_{Y43G}$ | Component of the 20S core proteasome complex involved in the proteolytic degradation of most intracellular proteins. | Cleavage of peptide bonds with very broad specificity. |
| Proteasome subunit beta type-6 | Psmb 6 | Q60692 | ScTyr$_{Y43G}$ | Component of the 20S core proteasome complex involved in the proteolytic degradation of most intracellular proteins. | Cleavage of peptide bonds with very broad specificity. |
| Protein/nucleic acid deglycase DJ-1 | Park7 | Q99LX0 | ScTyr$_{Y43G}$ | Protein and nucleotide deglycase that catalyzes the deglycation of the Maillard adducts formed between amino groups of proteins or nucleotides and reactive carbonyl groups of glyoxals. | An S-(1-hydroxy-2-oxopropyl)-[protein]-L-cysteine + H(2)O = a [protein]-L-cysteine + (R)-lactate. |
| Pyruvate kinase PKM | Pkm | P52480 | MmPhe$_{T413G}$ | Glycolytic enzyme that catalyzes the transfer of a phosphoryl group from phosphoenolpyruvate (PEP) to ADP, generating ATP. | ATP + pyruvate = ADP + phosphoenolpyruvate. |
| Rab GDP dissociation inhibitor alpha | Gdi1 | P50396 | MmPhe$_{T413G}$ | Regulates the GDP/GTP exchange reaction of most Rab proteins by inhibiting the dissociation of GDP from them, and the subsequent binding of GTP to them. | |
| Serum amyloid A-1 protein | Saa1 | P05366 | ScTyr$_{Y43G}$ | Major acute phase reactant. | |
| Serum amyloid A-2 protein | Saa2 | P05367 | ScTyr$_{Y43G}$ | Major acute phase reactant. | |

TABLE 1-continued

Labeled proteins secreted from B16-F10 melanomas into the plasma in FIG. 5F.

| Protein name | Gene | Uniprot ID | Identifying aaRS | Function | Catalytic Activity |
|---|---|---|---|---|---|
| Serum paraoxonase/ arylesterase 1 | Pon1 | P52430 | MmPhe$_{T413G}$ | Hydrolyzes the toxic metabolites of a variety of organophosphorus insecticides. | An N-acyl-L-homoserine lactone + H(2)O = an N-acyl-L-homoserine. |
| Transketolase | Tkt | P40142 | ScTyr$_{Y43G}$ | Catalyzes the transfer of a two-carbon ketol group from a ketose donor to an aldose acceptor, via a covalent intermediate with the cofactor thiamine pyrophosphate. | Sedoheptulose 7-phosphate + D-glyceraldehyde 3-phosphate = D-ribose 5-phosphate + D-xylulose 5-phosphate. |
| Transthyretin | Ttr | P07309 | ScTyr$_{Y43G}$ | Thyroid hormone-binding protein. | |
| Triosephosphate isomerase | Tpi1 | P17751 | Both | | D-glyceraldehyde 3-phosphate = glycerone phosphate. |
| UTP-glucose-1-phosphate uridylyltransferase | Ugp2 | Q91ZJ5 | MmPhe$_{T413G}$ | Plays a central role as a glucosyl donor in cellular metabolic pathways. | UTP + alpha-D-glucose 1-phosphate = diphosphate + UDP-glucose. |

Information on protein Function and Catalytic Activity are from the Gene Ontology database via the STRAP software.

Example 2. In Vivo Protein Labeling with Variant tRNA Synthetases for Detecting Tissue-Derived, Tagged Proteins in Blood We determined proteins produced specifically from the liver in both plasma and the brain. To do so, we injected the DJ serotype of adeno-associated virus (AAV-DJ) expressing FLAG-tagged ScTyr$_{Y43G}$ under the EF-1a promoter into the tail vein of mice (n=3), as mouse tail-vein injections of AAV-DJ were previously shown to specifically target the liver (48). 2 weeks after AAV-DJ injections, we intraperitoneally injected 300 mg/kg of AzY dissolved in phosphate buffered saline into the mice daily for a period of 5 days. We collected plasma from the mice 12-16 hours after the final injection by cardiac puncture, then perfused the mice with phosphate buffered saline, and harvested the liver and brain. Many infected hepatocytes with hexagonal hepatocyte morphology in liver sections were seen to produce labeled proteins (FIG. 21), while some nearby hepatocytes contain little or no labeling.

We then sonicated the liver and brain and performed mass spectrometry on individual brain and plasma samples as described in the Materials and Methods section in Example 1. From our mass spectrometry preparation of the plasma samples, we found many labeled proteins significantly enriched (Table 2, plasma) compared to controls not injected with AAV, including many that are produced specifically by hepatocytes (49). Likewise, many proteins found significantly in plasma (p<0.05) were also significantly found in the brain (Table 2, brain p<0.05).

TABLE 2

Top labeled proteins produced by the liver found in the plasma and the brain

| Group | Gene names |
|---|---|
| plasma (p <0.001) | F13b |
| | Apoa1 |
| | Gc |
| | Oh |
| | Serpinf2 |
| | Etfa |
| | C3 |
| | C8a |
| | Fetub |
| | Serpinc1 |
| | Plg |
| | C9 |
| | Masp1 |
| | Mug1 |
| | Il1rap |
| | Kng1 |
| | Serpina3k |
| | H2-Q10 |
| | Ica |
| | Hpx |
| | Mm |
| | C2 |
| | C8b |
| | Cp |
| | Cpn2 |
| | Ces1b |
| | Kcnab2 |
| | Gm4788 |
| | Saa4 |
| | Hgfac |
| | Cpn1 |
| | Itih3 |
| | C1ra |
| | Klkb1 |
| | Ambp |
| | Apon |
| | F12 |

TABLE 2-continued

Top labeled proteins produced by the liver found in the plasma and the brain

| Group | Gene names |
|---|---|
| plasma (0.001 <p <0.01) | Kng2 |
| | Serping1 |
| | Ces1d |
| | F2 |
| | Apoh |
| | Pon1 |
| | Cfhr2 |
| | Itih2 |
| | Vtn |
| | Rbp4 |
| | Pzp |
| | C4b |
| | Arhgef7 |
| | Azgp1 |
| | Itih1 |
| | Ces1c |
| | F10 |
| | Egfr |
| | C8g |
| | Gpld1 |
| | Apoa2 |
| | Gm20547 |
| | Lifr |
| | Ighv1-4 |
| | Ptprd |
| | Cfi |
| | Ahsg |
| | B2m |
| | C4bpa |
| | Me3 |
| | Itih4 |
| | Clu |
| | Wdr47 |
| | Habp2 |
| | Trim2 |
| | Pglyrn2 |
| | Apom |
| | Crp |
| | Syne1 |
| | Mb12 |
| | Ces1f |
| | Serpina3m |
| | Orm1 |
| | Masp2 |
| | C5 |
| | Serpina6 |
| | Cfd |
| | Fgg |
| | Qsox1 |
| | Clip1 |
| | Usp12 |
| | Apoa4 |
| | Tf |
| | Itih1 |
| | Apob |
| | Apoc2 |
| | Serpina3n |
| | Galnt18 |
| | Amy1 |
| | Fgb |
| | Apcs |
| | Cpb2 |
| | F9 |
| | Ighv1-52 |
| | Itih4 |
| | Cls1 |
| | Serpina10 |
| | Mup15 |
| | Mst1 |
| | Strn |
| | Apoc3 |
| | Gm20390 |
| | Lcat |
| plasma (0.01 <p <0.05) | Fga |
| | Serpina7 |
| | Apoe |
| | Acs16 |
| | Ighv1-72 |
| | Brca2 |
| | Manla1 |
| | Lbp |
| | Hspa5 |
| | Agt |
| | F5 |
| | Armc8 |
| | Btd |
| | Znfx1 |
| | Serpina1b |
| | Aldob |
| | H6pd |
| | Gpt |
| | Hgd |
| | Eef2 |
| | Me1 |
| | Serpind1 |
| | Serpina1d |
| | Serpina1c |
| | Hp |
| | Selenop |
| | C6 |
| brain (p <0.05) | Cfhr1 |
| | Cntnap4 |
| | Ptgfrn |
| | Gstm1 |
| | Fnl |
| | Wdr47 |
| | Il1rap |
| | Trim2 |
| | Me3 |
| | Gm20390 |
| | Syne1 |
| | Acs16 |
| | Clip1 |
| | Gstm1 |
| | Me1 |
| | Arhgef7 |
| | Serpina3k |
| | Brca2 |
| | Hspa5 |
| | Eef2 |
| | Tf |
| | Usp12 |
| | Fgg |
| | Serpina1c |
| | Znfx1 |
| | Strn |
| | Serpina1d |

We also labeled neuronal proteins in the brain directly in order to determine proteins in plasma that are produced by neurons. To do so, we injected the PHP.eB serotype of AAV expressing FLAG-tagged ScTyr$_{Y43G}$ under the hSyn promoter either into the retro-orbital sinus or bilaterally into the brain lateral ventricles (ventricle stereotactic injection coordinates ±1.0 mm ML, −0.3 mm AP, −2.5 mm DV) (50). 2 weeks after AAV injections, we intraperitoneally injected 300 mg/kg of AzY dissolved in phosphate buffered saline into the mice daily for a period of 5 days. We collected plasma from the mice 12-16 hours after the final injection by cardiac puncture, then perfused the mice with phosphate buffered saline, and harvested the liver and brain. We could see neuron labeling in several brain regions (FIG. 22), with neuron axonal projections clearly seen for a few of these neurons, while some nearby neurons contain little or no labeling. Using mass spectrometry after protein enrichment, we found many enriched proteins in plasma samples from AAV-injected mice compared to control mice that did not receive AAV (Table 3).

TABLE 3

Top labeled proteins produced by the brain found in the plasma and the brain

| Group | Gene names |
|---|---|
| plasma | Pkm |
| | Ttn |
| | Scrn1 |
| | Psmb6 |
| | Atp1a2 |
| | Psmb4 |
| | Tpi1 |
| | Cpe |
| | Blmh |
| | Asl |
| | Psmb2 |
| | Slc25a1 |
| | Tnr |
| | Aldoa |
| | Fasn |
| | Hsp90aa1 |
| | Psma6 |
| | Pitpnm2 |
| | Cela1 |
| | Flna |
| brain | Eif3l |
| | Slc25a12 |
| | Cops5 |
| | Napg |
| | Pfn2 |
| | Actrlb |
| | Ppa1 |
| | Eif4a1 |
| | Necap1 |
| | Atp6v1c1 |
| | Cmpk1 |
| | Ncl |
| | Kars |
| | Ndrg3 |
| | Syp |
| | Ehbp1 |
| | Dnaja2 |
| | Rtn4 |
| | Ppp2r5b |
| | Yars |

V. References (1) Conboy, I. M.; Conboy, M. J.; Wagers, A. J.; Girma, E. R.; Weismann, I. L.; Rando, T. A. Nature 2005, 433 (7027), 760-764.
(2) Villeda, S. A.; Plambeck, K. E.; Middeldorp, J.; Castellano, J. M.; Mosher, K. I.; Luo, J.; Smith, L. K.; Bieri, G.; Lin, K.; Berdnik, D.; Wabl, R.; Udeochu, J.; Wheatley, E. G.; Zou, B.; Simmons, D. A.; Xie, X. S.; Longo, F. M.; Wyss-Coray, T. Nat. Med. 2014, 20 (6), 659-663.
(3) Wyss-Coray, T. Nature. 2016, pp 180-186.
(4) Nedergaard, M.; Verkhratsky, A. Glia 2012, 60 (7), 1013-1023.
(5) Sharma, K.; Schmitt, S.; Bergner, C. G.; Tyanova, S.; Kannaiyan, N.; Manrique-Hoyos, N.; Kongi, K.; Cantuti, L.; Hanisch, U. K.; Philips, M. A.; Rossner, M. J.; Mann, M.; Simons, M. Nat. Neurosci. 2015, 18 (12), 1819-1831.
(6) Stone, S. E.; Glenn, W. S.; Hamblin, G. D.; Tirrell, D. A. Current Opinion in Chemical Biology. 2017, pp 50-57.
(7) Ngo, J. T.; Champion, J. A.; Mandavi, A.; Tanrikulu, I. C.; Beatty, K. E.; Connor, R. E.; Yoo, T. H.; Dieterich, D. C.; Schuman, E. M.; Tirrell, D. A. Nat. Chem. Biol. 2009, 5 (10), 715-717.
(8) Ngo, J. T.; Schuman, E. M.; Tirrell, D. A. Proc. Natl. Acad. Sci. 2013, 110 (13), 4992-4997.
(9) Yuet, K. P.; Doma, M. K.; Ngo, J. T.; Sweredoski, M. J.; Graham, R. L. J.; Moradian, A.; Hess, S.; Schuman, E. M.; Sternberg, P. W.; Tirrell, D. A. Proc. Natl. Acad. Sci. 2015, 112 (9), 2705-2710.
(10) Erdmann, I.; Marter, K.; Kobler, O.; Niehues, S.; Abele, J.; Müller, A.; Bussmann, J.; Storkebaum, E.; Ziv, T.; Thomas, U.; Dieterich, D. C. Nat. Commun. 2015, 6, 7521.
(11) Mandavi, A.; Hamblin, G. D.; Jindal, G. A.; Bagert, J. D.; Dong, C.; Sweredoski, M. J.; Hess, S.; Schuman, E. M.; Tirrell, D. A. J. Am. Chem. Soc. 2016, 138 (13), 4278-4281.
(12) Elliott, T. S.; Townsley, F. M.; Bianco, A.; Ernst, R. J.; Sachdeva, A.; Elsasser, S. J.; Davis, L.; Lang, K.; Pisa, R.; Greiss, S.; Lilley, K. S.; Chin, J. W. Nat. Biotechnol. 2014, 32 (5), 465-472.
(13) Sletten, E. M.; Bertozzi, C. R. Angewandte Chemie—International Edition. 2009, pp 6974-6998.
(14) Dieterich, D. C.; Link, A. J.; Graumann, J.; Tirrell, D. A.; Schuman, E. M. Proc. Natl. Acad. Sci. 2006, 103 (25), 9482-9487.
(15) Kiick, K. L.; Saxon, E.; Tirrell, D. A.; Bertozzi, C. R. Proc. Natl. Acad. Sci. 2002, 99 (1), 19-24.
(16) Alvarez-Castelao, B.; Schanzenbächer, C. T.; Hanus, C.; Glock, C.; tom Dieck, S.; Dörrbaum, A. R.; Bartnik, I.; Nassim-Assir, B.; Ciirdaeva, E.; Mueller, A.; Dieterich, D. C.; Tirrell, D. A.; Langer, J. D.; Schuman, E. M. Nat. Biotechnol. 2017, 35(12), 1196.
(17) Elliott, T. S.; Bianco, A.; Townsley, F. M.; Fried, S. D.; Chin, J. W. Cell Chem. Biol. 2016, 23 (7), 805-815.
(18) Howden, A. J. M.; Geoghegan, V.; Katsch, K.; Efstathiou, G.; Bhushan, B.; Boutureira, O.; Thomas, B.; Trudgian, D. C.; Kessler, B. M.; Dieterich, D. C.; Davis, B. G.; Acuto, O. Nat. Methods 2013, 10 (4), 343-346.
(19) Wang, L.; Brock, A.; Herberich, B.; Schultz, P. G. Science (80-.). 2001, 292 (5516), 498-500.
(20) Chin, J. W.; Santoro, S. W.; Martin, A. B.; King, D. S.; Wang, L.; Schultz, P. G. J. Am. Chem. Soc. 2002, 124 (31), 9026-9027.
(21) Deiters, A.; Cropp, T. A.; Mukherji, M.; Chin, J. W.; Anderson, J. C.; Schultz, P. G. J. Am. Chem. Soc. 2003, 125 (39), 11782-11783.
(22) Tsunoda, M.; Kusakabe, Y.; Tanaka, N.; Ohno, S.; Nakamura, M.; Senda, T.; Moriguchi, T.; Asai, N.; Sekine, M.; Yokogawa, T.; Nishikawa, K.; Nakamura, K. T. Nucleic Acids Res. 2007, 35 (13), 4289-4300.
(23) Wakasugi, K.; Quinn, C. L.; Tao, N.; Schimmel, P. EMBO J. 1998, 17 (1), 297-305.
(24) Yokogawa, T.; Ohno, S.; Nishikawa, K. Methods Mol. Biol. 2010, 607, 227-242.
(25) van Geel, R.; Pruijn, G. J. M.; van Delft, F. L.; Boelens, W. C. Bioconjug. Chem. 2012, 23 (3), 392-398.
(26) Gogvadze, V.; Orrenius, S.; Zhivotovsky, B. Trends in Cell Biology. 2008, pp 165-173.
(27) Chalkiadaki, A.; Guarente, L. Nature Reviews Cancer. 2015, pp 608-624.
(28) Schiarea, S.; Solinas, G.; Allavena, P.; Scigliuolo, G. M.; Bagnati, R.; Fanelli, R.; Chiabrando, C. J. Proteome Res. 2010, 9 (9), 4376-4392.
(29) Jansen, F. H.; Krijgsveld, J.; van Rijswijk, A.; van den Bemd, G.-J.; van den Berg, M. S.; van Weerden, W. M.;

Willemsen, R.; Dekker, L. J.; Luider, T. M.; Jenster, G. Mol. Cell. Proteomics 2009, 8 (6), 1192-1205.
(30) Gatenby, R. A.; Gillies, R. J. Nature Reviews Cancer. 2004, pp 891-899.
(31) Mani, A.; Gelmann, E. P. J. Clin. Oncol. 2005, 23 (21), 4776-4789.
(32) Yi, H.; Zheng, X.; Song, J.; Shen, R.; Su, Y.; Lin, D. Int. J. Clin. Exp. Pathol. 2015, 8 (12), 15719-15728.
(33) Liu, Y.; Conboy, M. J.; Mehdipour, M.; Liu, Y.; Tran, T. P.; Blotnick, A.; Rajan, P.; Santos, T. C.; Conboy, I. M. Nat. Commun. 2017, 8 (1).
(34) Krogager, T. P.; Ernst, R. J.; Elliott, T. S.; Calo, L.; Beránek, V.; Ciabatti, E.; Spillantini, M. G.; Tripodi, M.; Hastings, M. H.; Chin, J. W. Nat. Biotechnol. 2017, 36(2), 156.
(35) Wakasugi, K.; Quinn, C. L.; Tao, N.; Schimmel P. Genetic code in evolution: switching species-specific aminoacylation with a peptide transplant. The EMBO Journal. 1998 Jan. 1; 17(1):297-305.
(36) Thesis: Mandavi, Alborz. Ph.D. Dissertation, California Institute of Technology, Pasadena, Calif., 2015.
(37) Mandavi, A.; Hamblin, G D.; Jindal, G A.; Bagert, J D.; Dong, C.; Sweredoski, M J.; Hess, S.; Schuman, E M.; Tirrell, D A. Engineered aminoacyl-tRNA synthetase for cell-selective analysis of mammalian protein synthesis. Journal of the American Chemical Society. 2016 Mar. 25; 138(13):4278-81.
(38) Lund, R.; Leth-Larsen, R.; Jensen, O N.; Ditzel, H J. Efficient isolation and quantitative proteomic analysis of cancer cell plasma membrane proteins for identification of metastasis-associated cell surface markers. Journal of proteome research. 2009 Apr. 27; 8(6):3078-90.
(39) Zhang, L.; Elias, J E. Relative protein quantification using tandem mass tag mass spectrometry. Proteomics: Methods and Protocols. 2017:185-98.
(40) Eng, J K.; McCormack, A L.; Yates, J R. An approach to correlate tandem mass spectral data of peptides with amino acid sequences in a protein database. Journal of the American Society for Mass Spectrometry. 1994 Nov. 1; 5(11):976-89.
(41) Käll, L.; Canterbury, J D.; Weston, J.; Noble, W S.; MacCoss, M J. Semi-supervised learning for peptide identification from shotgun proteomics datasets. Nature methods. 2007 November; 4(11):923.
(42) Dray, S.; Dufour, A B. The ade4 package: implementing the duality diagram for ecologists. Journal of statistical software. 2007 January; 22(4):1-20.
(43) Tyanova, S.; Temu, T.; Sinitcyn, P.; Carlson, A.; Hein, M Y.; Geiger, T.; Mann, M.; Cox, J. The Perseus computational platform for comprehensive analysis of (prote) omics data. Nature methods. 2016 September; 13(9):731.
(44) Alvarez-Castelao, B.; Schanzenbächer, C T.; Hanus, C.; Glock, C.; tom Dieck, S.; Dörrbaum, A R.; Bartnik, I.; Nassim-Assir, B.; Ciirdaeva, E.; Mueller, A.; Dieterich D C. Cell-type-specific metabolic labeling of nascent proteomes in vivo. Nature biotechnology. 2017 December; 35(12):1196.
(45) Bhatia, V N.; Perlman, D H.; Costello, C E.; McComb, M E. Software tool for researching annotations of proteins: open-source protein annotation software with data visualization. Analytical chemistry. 2009 Oct. 19; 81(23): 9819-23.
(46) Kramer, A.; Green, J.; Pollard, Jr J.; Tugendreich, S. Causal analysis approaches in ingenuity pathway analysis. Bioinformatics. 2013 Dec. 13; 30(4):523-30.
(47) Elliott, T S.; Bianco, A.; Townsley, F M.; Fried, S D.; Chin, J W. Tagging and enriching proteins enables cell-specific proteomics. Cell chemical biology. 2016 Jul. 21; 23(7):805-15.
(48) Liu, J.; Moon, Y. A. Simple Purification of Adeno-Associated Virus-DJ for Liver-Specific Gene Expression. Yonsei Medical Journal. 2016 Mar. 15; 57(3):790-4.
(49) Schaum, N.; et al. Single-cell transcriptomics of 20 mouse organs creates a Tabula Muris. Nature. 2018 Oct. 3; 562(7727):367-72.
(50) Chan, K. Y.; Jang, M. J.; Yoo, B. B.; Greenbaum, A.; Ravi, N.; Wu, W. L.; Sanchez-Guardado, L.; Lois, C.; Mazmanian, S. K.; Deverman, B. E.; Gradinaru, V. Engineered AAVs for efficient noninvasive gene delivery to the central and peripheral nervous systems. Nat Neuroscience. 2017 Jun. 26; 20(8):1172-9.

VI. Exemplary Embodiments

Exemplary embodiments provided in accordance with the presently disclosed subject matter include, but are not limited to, the claims and the following embodiments:

1. A method for labeling the proteome of a cell or a portion of the proteome of a cell, the method comprising:
(a) introducing into the cell one or more variant aminoacyl-tRNA synthetases that recognize one or more noncanonical amino acids;
(b) introducing one or more noncanonical amino acids into the cell;
(c) exposing the cell to conditions such that the one or more variant aminoacyl-tRNA synthetases activate one or more tRNAs in the cell with the one or more noncanonical amino acids, thereby producing one or more noncanonical activated tRNAs, and the one or more noncanonical amino acids are integrated into the proteome by the one or more noncanonical activated tRNAs, thereby producing a modified proteome; and
(d) contacting the modified proteome with a detectable moiety, thereby producing a labeled proteome.

2. The method of embodiment 1, wherein the proteome or portion thereof comprises the secretome of the cell or a portion thereof.

3. A method for labeling a protein or a population of proteins produced by a cell, the method comprising:
(a) introducing into the cell one or more variant aminoacyl-tRNA synthetases that recognize one or more noncanonical amino acids;
(b) introducing one or more noncanonical amino acids into the cell;
(c) exposing the cell to conditions such that the one or more variant aminoacyl-tRNA synthetases activate one or more tRNAs in the cell with the one or more noncanonical amino acids, thereby producing one or more noncanonical activated tRNAs, and the one or more noncanonical amino acids are integrated into the protein or population of proteins by the one or more noncanonical activated tRNAs, thereby producing a modified protein or a population of modified proteins; and
(d) contacting the modified protein or population of modified proteins with a detectable moiety, thereby producing a labeled protein or a population of labeled proteins.

4. The method of embodiment 3, wherein the protein or population of proteins produced by the cell is secreted by the cell.

5. The method of any one of embodiments 1 to 4, wherein at least one of the one or more variant aminoacyl-tRNA synthetases comprise an amino acid substitution in an amino acid binding pocket compared to a corresponding wild-type aminoacyl-tRNA synthetase.

6. The method of embodiment 5, wherein the amino acid substitution replaces a wild-type amino acid with a glycine.

7. The method of any one of embodiments 1 to 6, wherein the one or more variant aminoacyl-tRNA synthetases are selected from the group consisting of ScTyr$_{Y43G}$, MmPhe$_{T413G}$, HsPhe$_{T413G}$, MmMet$_{L274G}$, pyrrolysyl-tRNA synthetase, and a combination thereof.

8. The method of embodiment 7, wherein the one or more variant aminoacyl-tRNA synthetases comprise ScTyr$_{Y43G}$ and MmPhe$_{T413G}$.

9. The method of embodiment 7, wherein the one or more variant aminoacyl-tRNA synthetases comprise ScTyr$_{Y43G}$ and HsPhe$_{T413G}$.

10. The method of embodiment 7, wherein the one or more variant aminoacyl-tRNA synthetases comprise ScTyr$_{Y43G}$ and MmMet$_{L274G}$.

11. The method of embodiment 7, wherein the one or more variant aminoacyl-tRNA synthetases comprise MmPhe$_{T413G}$ and MmMet$_{L274G}$.

12. The method of embodiment 7, wherein the one or more variant aminoacyl-tRNA synthetases comprise HsPhe$_{T413G}$ and MmMet$_{L274G}$.

13. The method of embodiment 7, wherein the one or more variant aminoacyl-tRNA synthetases comprise MmPhe$_{T413G}$ and HsPhe$_{T413G}$.

14. The method of embodiment 7, wherein the one or more variant aminoacyl-tRNA synthetases comprise ScTyr$_{Y43G}$, MmPhe$_{T413G}$, and HsPhe$_{T413G}$.

15. The method of embodiment 7, wherein the one or more variant aminoacyl-tRNA synthetases comprise ScTyr$_{Y43G}$, MmPhe$_{T413G}$, and MmMet$_{L274G}$.

16. The method of embodiment 7, wherein the one or more variant aminoacyl-tRNA synthetases comprise ScTyr$_{Y43G}$, HsPhe$_{T413G}$, and MmMet$_{L274G}$.

17. The method of embodiment 7, wherein the one or more variant aminoacyl-tRNA synthetases comprise MmPhe$_{T413G}$, HsPhe$_{T413G}$, and MmMet$_{L274G}$.

18. The method of embodiment 7, wherein the one or more variant aminoacyl-tRNA synthetases comprise ScTyr$_{Y43G}$, MmPhe$_{T413G}$, HsPhe$_{T413G}$, and MmMet$_{L274G}$.

19. The method of any one of embodiments 1 to 18, wherein the one or more variant aminoacyl-tRNA synthetases comprise an amino acid sequence having at least about 80% identity to any one of SEQ ID NOS:4-6.

20. The method of embodiment 19, wherein the one or more variant aminoacyl-tRNA synthetases comprise the amino acid sequence of any one of SEQ ID NOS:4-6.

21. The method of any one of embodiments 1 to 20, wherein the one or more variant aminoacyl-tRNA synthetases are encoded by a nucleic acid sequence having at least about 80% identity to any one of SEQ ID NOS:1-3.

22. The method of embodiment 21, wherein the one or more variant aminoacyl-tRNA synthetases are encoded by the nucleic acid sequence set forth in any one of SEQ ID NOS:1-3.

23. The method of any one of embodiments 1 to 22, wherein the one or more variant aminoacyl-tRNA synthetases are encoded by a polynucleotide that is codon-optimized to increase expression of the one of more variant aminoacyl-tRNA synthetases.

24. The method of any one of embodiments 1 to 23, wherein two or more different variant aminoacyl-tRNA synthetases that recognize noncanonical amino acids are used, and wherein using two or more different variant aminoacyl-tRNA synthetases that recognize noncanonical amino acids increases the number of proteins that are labeled compared to when a single variant aminoacyl-tRNA synthetase that recognizes a noncanonical amino acid is used.

25. The method of any one of embodiments 1 to 24, wherein at least one of the one or more tRNAs in the cell recognizes a methionine codon and/or a non-methionine codon.

26. The method of any one of embodiments 1 to 25, wherein at least one of the one or more tRNAs in the cell recognizes more than one cognate codon.

27. The method of any one of embodiments 1 to 26, wherein all of the tRNAs in the cell are endogenous.

28. The method of any one of embodiments 1 to 27, wherein the one or more noncanonical amino acids comprise an azide, an alkyne, a tetrazine, or a combination thereof.

29. The method of any one of embodiments 1 to 28, wherein the one or more noncanonical amino acids comprise an aryl azide.

30. The method of embodiment 29, wherein the one or more noncanonical amino acids comprising an aryl azide are selected from the group consisting of p-azido-L-phenylalanine (AzF), 3-azido-L-tyrosine (AzY), and a combination thereof.

31. The method of any one of embodiments 1 to 30, wherein the one or more variant aminoacyl-tRNA synthetases activate the one or more tRNAs in the cell preferentially with the one or more noncanonical amino acids compared to a canonical amino acid.

32. The method of any one of embodiments 1 to 31, wherein the detectable moiety comprises a fluorophore, an affinity resin, or a crosslinking reagent.

33. The method of any one of embodiments 1 to 32, wherein the labeled proteome, labeled protein, or population of labeled proteins is detected using a method selected from the group consisting of fluorescent imaging, flow cytometry, mass spectrometry, and a combination thereof.

34. The method of any one of embodiments 1 to 33, wherein the cell is a mammalian cell.

35. The method of any one of embodiments 1 to 34, wherein the cell is a human cell.

36. The method of any one of embodiments 1 to 35, wherein the cell is an immune cell, a neural cell, or a liver cell.

37. The method of embodiment 36, wherein the neural cell is a central nervous system (CNS) cell, a brain cell, a spinal cord cell, or a combination thereof.

38. The method of any one of embodiments 1 to 37, wherein the cell is selected from the group consisting of a cancer cell, a transplanted cell, a senescent cell, a degenerating neuron, and an inflamed immune cell.

39. The method of embodiment 38, wherein the cancer cell is derived from an animal model and/or a patient-derived xenograft model.

40. The method of embodiment 38 or 39, wherein the cancer cell is a melanoma cell.

41. The method of any one of embodiments 1 to 40, wherein the labeling is performed in vivo.

42. The method of embodiment 41, wherein the method further comprises detecting the labeled proteome, labeled protein, or population of labeled proteins in a sample obtained from a subject.

43. The method of embodiment 42, wherein the sample is a blood sample, a urine sample, a saliva sample, a cerebrospinal fluid sample, a tissue sample, a fine needle aspirate sample, a biopsy sample, or a combination thereof.

44. The method of any one of embodiments 1 to 43, wherein the labeling is cell-type-specific.

45. The method of any one of embodiments 1 to 44, wherein the labeling is temporally-restricted.

46. A labeled protein or a population of labeled proteins, wherein the protein or population of proteins is labeled by the method of any one of embodiments 3 to 45.

47. An isolated polynucleotide encoding a variant aminoacyl-tRNA synthetase that recognizes a noncanonical amino acid, wherein the isolated polynucleotide comprises a nucleic acid sequence having at least about 80% identity to any one of SEQ ID NOS:1-3.

48. The isolated polynucleotide of embodiment 47, wherein the isolated polynucleotide comprises the nucleic acid sequence of any one of SEQ ID NOS:1-3.

49. The isolated polynucleotide of embodiment 47 or 48, wherein the nucleic acid sequence is codon-optimized to increase expression of the variant aminoacyl-tRNA synthetase.

50. The isolated polynucleotide of any one of embodiments 47 to 49, wherein the encoded variant aminoacyl-tRNA synthetase comprises an amino acid substitution in an amino acid binding pocket compared to a corresponding wild-type aminoacyl-tRNA synthetase.

51. The isolated polynucleotide of embodiment 50, wherein the amino acid substitution replaces a wild-type amino acid with a glycine.

52. The isolated polynucleotide of any one of embodiments 47 to 51, wherein the encoded variant aminoacyl-tRNA synthetase is selected from the group consisting of $ScTyr_{Y43G}$, $MmPhe_{T413G}$, and $HsPhe_{T413G}$.

53. The isolated polynucleotide of any one of embodiments 47 to 52, wherein the encoded variant aminoacyl-tRNA synthetase comprises an amino acid sequence having at least about 80% identity to any one of SEQ ID NOS:4-6.

54. The isolated polynucleotide of embodiment 53, wherein the encoded variant aminoacyl-tRNA synthetase comprises the amino acid sequence of any one of SEQ ID NOS:4-6.

55. The isolated polynucleotide of any one of embodiments 47 to 54, wherein the encoded variant aminoacyl-tRNA synthetase activates a tRNA preferentially with a noncanonical amino acid compared to a canonical amino acid.

56. The isolated polynucleotide of any one of embodiments 47 to 55, wherein the isolated polynucleotide encodes two or more variant aminoacyl-tRNA synthetases that recognize noncanonical amino acids.

57. The isolated nucleotide of any one of embodiments 47 to 56, further comprising a nucleic acid sequence encoding a regulatory element.

58. The isolated nucleotide of embodiment 57, wherein the regulatory element is selected from the group consisting of an IRES sequence, a viral 2A peptide sequence, an inducible promoter, a cell-specific promoter, and a combination thereof.

59. A cell comprising the polynucleotide of any one of embodiments 47 to 58.

60. The cell of embodiment 59, further comprising one or more noncanonical amino acids.

61. The cell of embodiment 60, wherein the one or more noncanonical amino acids comprise an azide, an alkyne, a tetrazine, or a combination thereof.

62. The cell of embodiment 60 or 61, wherein the one or more noncanonical amino acids comprise an aryl azide.

63. The cell of embodiment 62, wherein the one or more noncanonical amino acids comprising an aryl azide are selected from the group consisting of p-azido-L-phenylalanine (AzF), 3-azido-L-tyrosine (AzY), and a combination thereof.

64. The cell of any one of embodiments 59 to 63, further comprising a detectable moiety.

65. The cell of embodiment 64, wherein the detectable moiety comprises a fluorophore, an affinity resin, or a crosslinking reagent.

66. The cell of any one of embodiments 59 to 65, wherein the cell is a mammalian cell.

67. The cell of any one of embodiments 59 to 66, wherein the cell is a human cell.

68. The cell of any one of embodiments 59 to 67, wherein the cell is a cancer cell.

69. The cell of any one of embodiments 59 to 68, wherein the cell is a melanoma cell.

70. A kit for labeling the proteome of a cell or for labeling a protein or a population of proteins produced by a cell, the kit comprising the polynucleotide of any one of embodiments 47 to 58, the cell of any one of embodiments 59 to 69, or a combination thereof.

71. The kit of embodiment 70, further comprising one or more reagents.

72. The kit of embodiment 71, wherein the one or more reagents are for introducing a polynucleotide into the cell, expressing a variant aminoacyl-tRNA synthetase in the cell, introducing a noncanonical amino acid into the cell, introducing a detectable moiety into the cell, lysing the cell, detecting the labeled proteome, labeled protein, or population of labeled proteins, or a combination thereof.

73. The kit of any one of embodiments 70 to 72, further comprising instructions for use.

74. A method for identifying a target cell, the method comprising:

(a) labeling the proteome of the target cell or labeling a protein or a population of proteins produced by the target cell according to the method of any one of embodiments 1 to 45;

(b) labeling the proteome of a reference cell or labeling a protein or a population of proteins produced by a reference cell according to the method of any one of embodiments 1 to 45;

(c) detecting the labeled proteome, labeled protein, or population of labeled proteins in the target cell and reference cell to generate a target cell signature and a reference cell signature, respectively;

(d) comparing the target cell signature to the reference cell signature; and (e) identifying the target cell based on the comparison in step (d).

75. A method for identifying one or more biomarkers of interest in a target cell, the method comprising:

(a) labeling the proteome of the target cell or labeling a protein or a population of proteins produced by the target cell according to the method of any one of embodiments 1 to 45;

(b) labeling the proteome of a reference cell or labeling a protein or a population of proteins produced by a reference cell according to the method of any one of embodiments 1 to 45;

(c) detecting the labeled proteome, labeled protein, or population of labeled proteins in the target cell and reference cell to generate a target cell signature and a reference cell signature, respectively;

(d) comparing the target cell signature to the reference cell signature; and (e) identifying the one or more biomarkers of interest based on the comparison in step (d).

76. The method of embodiment 74 or 75, wherein the protein or population of proteins produced by the target cell and/or the reference cell are secreted by the target cell and/or the reference cell.

77. The method of any one of embodiments 74 to 76, wherein the target cell is a diseased cell.

78. The method of embodiment 77, wherein the diseased cell is a cancer cell or a neurological disease cell.

79. The method of embodiment 78, wherein the neurological disease cell is a neurodegenerative disease cell.

80. The method of embodiment 78, wherein the cancer cell is a melanoma cell.

81. The method of any one of embodiments 74 to 80, wherein the reference cell is a healthy cell.

82. The method of any one of embodiments 74 to 81, wherein the target cell and/or the reference cell are obtained from or derived from an in vivo model system and/or a patient-derived xenograft.

83. The method of any one of embodiments 74 to 82, wherein the labeled proteome, labeled protein, or population of labeled proteins is present in a sample obtained from a subject.

84. The method of embodiment 83, wherein the sample is obtained from the subject before and/or after the proteome, protein, or population of proteins is labeled and/or detected.

85. The method of embodiment 83 or 84, wherein the sample comprises a labeled secretome or a portion thereof.

86. The method of embodiment 85, wherein the labeled secretome or portion thereof is detected after being secreted from the target cell and/or reference cell.

87. The method of any one of embodiments 83 to 85, wherein the sample is a blood sample, a urine sample, a saliva sample, a cerebrospinal fluid sample, a tissue sample, a fine needle aspirate sample, a biopsy sample, or a combination thereof.

88. The method of any one of embodiments 74 to 87, wherein two or more variant aminoacyl-tRNA synthetases that recognize noncanonical amino acids are used, and wherein using two or more variant aminoacyl-tRNA synthetases that recognize noncanonical amino acids increases the sensitivity and/or specificity of target cell or biomarker identification, compared to when only one variant aminoacyl-tRNA synthetase that recognizes a noncanonical amino acid is used.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

VII. INFORMAL SEQUENCE LISTING

| SEQ ID NO: | Sequence | Description |
|---|---|---|
| 1 | ATGTCCTCAGCTGCCACCGTTGATCCAAATGAAGCTTTTGGGTTGAT AACAAAAAACCTCCAAGAAGTGTTGAACCCTCAGATCATCAAGGATG TCCTTGAAGTACAAAAAAGGCATTTGAAGCTCGGGTGGGGAACTGCC CCTACCGGGCGCCCACATTGTGGGTATTTCGTCCCTATGACTAAGTT GGCTGATTTCTTGAAGGCAGGCTGCGAGGTGACTGTGCTCCTGGCCG ACTTGCACGCCTTTTTGGATAATATGAAGGCCCCTCTCGAGGTCGTC AATTATCGAGCCAAGTACTACGAACTCACCATTAAAGCAATCTTGAG GAGTATAAACGTCCCTATAGAAAAACTTAAATTTGTTGTAGGTTCTT CATATCAACTGACACCCGATTATACCATGGACATTTTTAGACTGAGC AACATTGTGTCCCAAAACGATGCTAAAAGAGCAGGAGCTGACGTTGT GAAACAAGTTGCAAACCCACTTCTTTCAGGCCTGATATATCCTCTTA TGCAAGCACTCGACGAACAATTCCTTGATGTCGATTGCCAGTTCGGA GGTGTAGACCAGCGAAAAATCTTTGTTTTGGCCGAAGAGAACCTGCC CTCTCTGGGCTATAAAAAACGGGCTCACTTGATGAATCCAATGGTCC CCGGATTGCCCAAGGTGGCAAAATGTCTGCATCAGACCCCAACTCT AAAATAGATCTGCTGGAGGAACCAAAGCAAGTTAAGAAGAAAATTAA CTCCGCCTTTTGCAGTCCTGGCAATGTCGAGGAAAACGGGCTTCTGT CATTCGTGCAGTATGTGATCGCCCCAATTCAAGAACTCAAGTTCGGT ACAAATCATTTTGAGTTTTTTATAGATCGACCAGAAAAATTTGGGGG ACCTATTACATACAAGAGTTTTGAAGAGATGAAATTGGCCTTCAAAG AAGAGAAGCTGAGCCCACCTGATCTGAAGATCGGAGTGGCCGACGCC ATCAATGAGTTGCTTGAACCAATACGACAGGAATTTGCTGATAACAA AGAGTTTCAGGAAGCTAGTGAAAAGGGCTATCCCGTAGCAACCCCAC AAAAATCTAAAAAAGCAAAAAAAACCTAAGAATAAGGGTACTAAATAC CCTGGGGCTACCAAGACTAATGAAATTGCTACTAAGCTGGAGGAGAC TAAATTGTAATGATGATAA | ScTyr$_{Y43G}$ codon-optimized DNA sequence |
| 2 | ATGGCAGACAACCCTGTTCTCGAACTGCTCTTGCGGCGGTTGGAAGT AGCAGATGGAGGTTTGGATTCAGCAGAACTTGCCACCCAACTTGGCG TTGAACATCAGGCCGTCGTTGGGGCAGTGAAGAGTCTGCAAGCACTC GGGGAGGTGATAGAGGCTGAGCTTAGAAGTACAAAATGCTGGGAGTT GACCACCGAGGGTGAAGAGATTGCTAGAGAAGGGAGTCACGAGGCAC GCGTTTTTCGGAGTATACCTCTTGAAGGACTTGTGCAGTCAGAATTG ATGCACCTTCCCTCAGGTAAGGTTGGATTTAGTAAAGCCATGAGTAA TAAATGGATAAGAGTTGATAAATCAGCCGCCGACGGGCCAAGGGTGT TTAGAGTCGTCGATTCTATAGAGGATGAAGTACAGAAAAGACTCCAA CTGGTTCAGGCTGGACAAGCAGAAAAGCTCGCAGAAAAAGAACGGAA TGAATTGAGAAAACGCAAACTGCTGACCGAAGTGATTTTGAAAACAT ATTGGGTTTCAAAGGGGAAAGCATTTTCCACATCAGTGTCTAAGCAA GAAGCCGAGCTCTCCCCTGAAATGATTTCTAGCGGAAGTTGGCGGGA | MmPhe$_{T413G}$ codon-optimized DNA sequence |

VII. INFORMAL SEQUENCE LISTING

| SEQ ID NO: | Sequence | Description |
|---|---|---|
| | CCGACCATTCAAACCTTATAATTTCAGCGCAAGGGGAGTCCTTCCAG<br>ATTCAGGCCACCTCCACCCTCTTCTTAAAGTCCGCTCCCAGTTCCGG<br>CAGATCTTTCTGGAGATGGGGTTCACAGAAATGCCTACTGACAATTT<br>TATTGAGTCTAGCTTTTGGAATTTCGACGCACTCTTCCAGCCCCAAC<br>AGCACCCCGCAAGAGACCAACACGACACATTTTTCTCAGGGATCCT<br>GCTGAAGCTCTCCAATTGCCAATGGGATACGTTCAGAGGGTGAAGAG<br>AACTCATTCACAAGGAGGATATGGTTCTCAGGGATATAAGTACACCT<br>GGAAGTTGGAAGAGGCTAGGAAAAATCTCTTGCGGACTCACACTACA<br>GCCGCCTCCGCTCGCGCTCTGTATCAGCTCGCACAAAAAAGCCTTT<br>CACCCCAGCAAAATATTTCTCCATTGATCGCGTCTTCCGAAATGAAA<br>GCATTGGATGCCACACATTTGCTGAGTTCCACCAAATAGAAGGGGTC<br>ATCGCCGACCACGGTTTGACTCTTGGTCATTTGATGGGCGTATTGCG<br>CGAATTTTTCACCAAACTGGGGATTACACAGCTCCGATTTAAACCCG<br>CATACAACCCTTACGGGGAGCCAAGTATGGAAGTGTTTAGCTATCAC<br>CAGGGGCTCAAGAAGTGGGTTGAAGTGGGAAATTCAGGAGTCTTTAG<br>GCCCGAGATGCTTCTTCCAATGGGCCTGCCAGAAAACGTGTCAGTAA<br>TTGCATGGGGTCTCTCCCTCGAGAGACCCACAATGATAAAGTACGGA<br>ATTAATAACATACGCGAGTTGGTTGGGCACAAGGTAAACCTTCAGAT<br>GGTCTATGACTCACCCGTCTGTAGACTTGATATAGAGCCTCGATCCA<br>GCAAAACACAGGAGGCTGCCTGATGATAA | |
| 3 | ATGGCCGATGGGCAAGTGGCAGAGTTGCTCCTCCGGAGACTCGAGGCT<br>AGTGACGGAGGACTCGACAGCGCTGAGCTCGCTGCCGAACTGGGGATG<br>GAGCACCAAGCCGTGGTCGGGGCTGTCAAGAGCTTGCAGGCTTTGGGT<br>GAAGTCATCGAGGCTGAACTCAGGAGCACCAAACACTGGGAACTCACA<br>GCAGAAGGGGAAGAGATAGCTAGGGAAGGTAGCCACGAGGCTCGGGTT<br>TTTCGCTCCATTCCACCCGAGGGACTTGCTCAGTCAGAACTCATGCGG<br>CTTCCAAGTGGAAAAGTAGGATTTAGCAAAGCTATGAGTAACAAGTGG<br>ATACGAGTCGATAAAAGCGCTGCCGACGGCCCACGCGTATTCCGGGTG<br>GTGGATAGCATGGAAGATGAAGTGCAGCGGAGGCTTCAGTTGGTTCGC<br>GGAGGGCAGGCAGAGAAACTTGGTGAGAAAGAGCGCTCAGAACTTCGG<br>AAGAGGAAGCTGCTGGCCGAAGTTACCCTGAAAACTTATTGGGTGAGT<br>AAAGGCTCCGCCTTCAGTACCTCCATTTCCAAGCAGGAAACCGAGTTG<br>TCTCCAGAGATGATTAGTTCTGGAAGTTGGCGCGACAGGCCATTCAAG<br>CCCTACAACTTTCTCGCACACGGTGTGCTTCCCGATTCAGGTCATCTG<br>CACCCTCTCCTCAAAGTTAGATCACAGTTCCGCCAAATCTTTCTGGAG<br>ATGGGGTTCACCGAAATGCCTACAGATAACTTCATCGAATCCAGCTTC<br>TGGAATTTTGACGCACTGTTTCAGCCCCAACAACACCCCGCCAGAGAT<br>CAGCACGACACATTCTTCCTGCGAGACCCAGCCGAGGCTCTTCAGCTT<br>CCAATGGGATTATGTGCAGCGCGTAAAAAGAACTCATAGTCAAGGCGGG<br>TACGGAAGCCAGGGTTATAAGTACAATTGGAAACTGGATGAAGCAAGG<br>AAGAATCTCCTCCGCACACATACTACAAGTGCATCAGCCAGAGCCCTC<br>TATCGGCTCGCCCAAAAGAAGCCTTTTACCCCAGTGAAGTATTTTAGC<br>ATCGACCGGGTGTTCCGCAACGAGACACTGGATGCCACTCACCTGGCT<br>GAATTTCACCAGATCGAAGGAGTGGTCGCCGACCACGGGTTGACACTG<br>GGTCATTTGATGGGGGTGCTGCGAGAATTTTTTACTAAGCTGGGCATT<br>ACCCAACTCCGATTCAAACCAGCTTATAACCCCTATGGAGAACCATCA<br>ATGGAAGTCTTCAGTTACCATCAAGGCCTCAAAAAGTGGGTTGAAGTC<br>GGCAATTCCGGCGTCTTTCGACCTGAAATGCTGCTCCCCATGGGGCTT<br>CCTGAAAACGTTAGTGTAATAGCCTGGGGGTTGTCTCTTGAAAGGCCT<br>ACAATGATAAAATACGGGATTAATAATATCAGGGAGCTGGTTGGCCAT<br>AAAGTAAACTTGCAGATGGTTTACGATAGCCCCCTTTGCAGGCTCGAC<br>GCCGAACCACGGCCCCACCCACACAGGAAGCAGCATGA | HsPhe$_{T413G}$ codon-optimized DNA sequence |
| 4 | MSSAATVDPNEAFGLITKNLQEVLNPQIIKDVLEVQKRHLKLGWGTAPT<br>GRPHCGYFVPMTKLADFLKAGCEVTVLLADLHAFLDNMKAPLEVVNYRA<br>KYYELTIKAILRSINVPIEKLKFVVGSSYQLTPDYTMDIFRLSNIVSQN<br>DAKRAGADVVKQVANPLLSGLIYPLMQALDEQFLDVDCQFGGVDQRKIF<br>VLAEENLPSLGYKKRAHLMNPMVPGLAQGGKMSASDPNSKIDLLEEPKQ<br>VKKKINSAFCSPGNVEENGLLSFVQYVIAPIQELKFGTNHFEFFIDRPE<br>KFGGPITYKSFEEMKLAFKEEKLSPPDLKIGVADAINELLEPIRQEFAD<br>NKEFQEASEKGYPVATPQKSKKAKKPKNKGTKYPGATKTNEIATKLEET<br>KL | ScTyr$_{Y43G}$ amino acid sequence |
| 5 | MADNPVLELLLRRLEVADGGLDSAELATQLGVEHQAVVGAVKSLQALG<br>EVIEAELRSTKCWELTTEGEEIAREGSHEARVFRSIPLEGLVQSELMH<br>LPSGKVGFSKAMSNKWIRVDKSAADGPRVFRVVDSIEDEVQKRLQLVQ<br>AGQAEKLAEKERNELRKRKLLTEVILKTYWVSKGKAFSTSVSKQEAEL<br>SPEMISSGSWRDRPFKPYNFSARGVLPDSGHLHPLLKVRSQFRQIFLE<br>MGFTEMPTDNFIESSFWNFDALFQPQQHPARDQHDTFFLRDPAEALQL<br>PMGYVQRVKRTHSQGGYGSQGYKYTWKLEEARKNLLRTHTTAASARAL<br>YQLAQKKPFTPAKYFSIDRVFRNETLDATHLAEFHQIEGVIADHGLTL<br>GHLMGVLREFFTKLGITQLRFKPAYNPYGEPSMEVFSYHQGLKKWVEV | MmPhe$_{T413G}$ amino acid sequence |

VII. INFORMAL SEQUENCE LISTING

| SEQ ID NO: | Sequence | Description |
|---|---|---|
| | GNSGVFRPEMLLPMGLPENVSVIAWGLSLERPTMIKYGINNIRELVGH<br>KVNLQMVYDSPVCRLDIEPRSSKTQEAA | |
| 6 | MADGQVAELLLRRLEASDGGLDSAELAAELGMEHQAVVGAVKSLQALG<br>EVIEAELRSTKHWELTAEGEEIAREGSHEARVFRSIPPEGLAQSELMR<br>LPSGKVGFSKAMSNKWIRVDKSAADGPRVFRVVDSMEDEVQRRLQLVR<br>GGQAEKLGEKERSELRKRKLLAEVTLKTYWVSKGSAFSTSISKQETEL<br>SPEMISSGSWRDRPFKPYNFLAHGVLPDSGHLHPLLKVRSQFRQIFLE<br>MGFTEMPTDNFIESSFWNFDALFQPQQHPARDQHDTFFLRDPAEALQL<br>PMDYVQRVKRTHSQGGYGSQGYKYNWKLDEARKNLLRTHTTSASARAL<br>YRLAQKKPFTPVKYFSIDRVFRNETLDATHLAEFHQIEGVVADHGLTL<br>GHLMGVLREFFTKLGITQLRFKPAYNPYGEPSMEVFSYHQGLKKWVEV<br>GNSGVFRPEMLLPMGLPENVSVIAWGLSLERPTMIKYGINNIRELVGH<br>KVNLQMVYDSPLCRLDAEPRPPPTQEAA | HsPhe$_{T413G}$ amino acid sequence |
| 7 | MSSAATVDPNEAFGLITKNLQEVLNPQIIKDVLEVQKRHLKLYWGTAP<br>TGRPHCGYFVPMTKLADFLKAGCEVTVLLADLHAFLDNMKAPLEVVNY<br>RAKYYELTIKAILRSINVPIEKLKFVVGSSYQLTPDYTMDIFRLSNIV<br>SQNDAKRAGADVVKQVANPLLSGLIYPLMQALDEQFLDVDCQFGGVDQ<br>RKIFVLAEENLPSLGYKKRAHLMNPMVPGLAQGGKMSASDPNSKIDLL<br>EEPKQVKKKINSAFCSPGNVEENGLLSFVQYVIAPIQELKFGTNHFEF<br>FIDRPEKFGGPITYKSFEEMKLAFKEEKLSPPDLKIGVADAINELLEP<br>IRQEFADNKEFQEASEKGYPVATPQKSKKAKKPKNKGTKYPGATKTNE<br>IATKLEETKL | ScTyr wild-type amino acid sequence |
| 8 | MADNPVLELLLRRLEVADGGLDSAELATQLGVEHQAVVGAVKSLQALG<br>EVIEAELRSTKCWELTTEGEEIAREGSHEARVFRSIPLEGLVQSELMH<br>LPSGKVGFSKAMSNKWIRVDKSAADGPRVFRVVDSIEDEVQKRLQLVQ<br>AGQAEKLAEKERNELRKRKLLTEVILKTYWVSKGKAFSTSVSKQEAEL<br>SPEMISSGSWRDRPFKPYNFSARGVLPDSGHLHPLLKVRSQFRQIFLE<br>FMGFTEMPTDNIESSFWNFDALFQPQQHPARDQHD1FFLRDPAEALQL<br>SPMGYVQRVKRTHQGGYGSQGYKYTWKLEEEARKNLLRTHTTAASARAL<br>YYQLAQKKPFTPAKFSIDRVFRNETLDATHLAEFHQIEGVIADHGLTL<br>GHLMGVLREFFTKLGITQLRFKPAYNPYTEPSMEVFSYHQGLKKWVEV<br>GNSGVFRPEMLLPMGLPENVSVIAWGLSLERPTMIKYGINNIRELVGH<br>KVNLQMVYDSPVCRLDIEPRSSKTQEAA | MmPhe wild-type amino acid sequence |
| 9 | MADGQVAELLLRRLEASDGGLDSAELAAELGMEHQAVVGAVKSLQALG<br>EVIEAELRSTKHWELTAEGEEIAREGSHEARVFRSIPPEGLAQSELMR<br>LPSGKVGFSKAMSNKWIRVDKSAADGPRVFRVVDSMEDEVQRRLQLVR<br>GGQAEKLGEKERSELRKRKLLAEVTLKTYWVSKGSAFSTSISKQETEL<br>SPEMISSGSWRDRPFKPYNFLAHGVLPDSGHLHPLLKVRSQFRQIFLE<br>MGFTEMPTDNFIESSFWNFDALFQPQQHPARDQHDTFFLRDPAEALQL<br>PMDYVQRVKRTHSQGGYGSQGYKYNWKLDEARKNLLRTHTTSASARAL<br>KYRLAQKKPFTPVYFSIDRVFRNETLDATHLAEFHQIEGVVADHGLTL<br>GHLMGVLREFFTKLGITQLRFKPAYNPYTEPSMEVFSYHQGLKKWVEV<br>GNSGVFRPEMLLPMGLPENVSVIAWGLSLERPTMIKYGINNIRELVGH<br>KVNLQMVYDSPLCRLDAEPRPPPTQEAA | HsPhe wild-type amino acid sequence |
| 10 | ATGGCCGATGGGCAAGTGGCAGAGTTGCTCCTCCGGAGACTCGAGG<br>CTAGTGACGGAGGACTCGACAGCGCTGAGCTCGCTGCCGAACTGGG<br>GATGGAGCACCAAGCCGTGGTCGGGGCTGTCAAGAGCTTGCAGGCT<br>TTGGGTGAAGTCATCGAGGCTGAACTCAGGAGCACCAAACACTGGG<br>AACTCACAGCAGAAGGGGAAGAGATAGCTAGGGAAGGTAGCCACGA<br>GGCTCGGGTTTTTCGCTCCATTCCACCCGAGGGACTTGCTCAGTCA<br>GAACTCATGCGGCTTCCAAGTGGAAAAGTAGGATTTAGCAAAGCTA<br>TGAGTAACAAGTGGATACGAGTCGATAAAAGCGCTGCCGACGGCCC<br>ACGCGTATTCCGGGTGGTGGATAGCATGGAAGATGAAGTGCAGCGG<br>AGGCTTCAGTTGGTTCGCGGAGGGCAGGCAGAGAAACTTGGTGAGA<br>AAGAGCGCTCAGAACTTCGGAAGAGGAAGCTGCTGGCCGAAGTTAC<br>CCTGAAAACTTATTGGGTGAGTAAAGGCTCCGCCTTCAGTACCTCC<br>ATTTCCAAGCAGGAAACCGAGTTGTCTCCAGAGATGATTAGTTCTG<br>GAAGTTGGCGCGACAGGCCATTCAAGCCCTACAACTTTCTCGCACA<br>CGGTGTGCTTCCCGATTCAGGTCATCTGCACCCTCTCCTCAAAGTT<br>AGATCACAGTTCCGCCAAATCTTTCTGGAGATGGGGTTCACCGAAA<br>TGCCTACAGATAACTTCATCGAATCCAGCTTCTGGAATTTTGACGC<br>ACTGTTTCAGCCCCAACAACACCCCGCCAGAGATCAGCACGACCA<br>TTCTTCCTGCGAGACCCAGCCGAGGCTCTTCAGCTTCCAATGGATT<br>ATGTGCAGCGCGTAAAAAGAACTCATAGTCAAGGCGGGTACGGAAG<br>CCAGGGTTATAAGTACAATTGGAAACTGGATGAAGCAAGGAAGAAT<br>CTCCTCCGCACACATACTACAAGTGCATCAGCCAGAGCCCTCTATC<br>GGCTCGCCCAAAAGAAGCCTTTTACCCCAGTGAAGTATTTTAGCAT<br>CGACCGGGTGTTCCGCAACGAGACACTGGATGCCACTCACCTGGCT | HsPhe wild-type DNA sequence |

VII. INFORMAL SEQUENCE LISTING

| SEQ ID NO: | Sequence | Description |
|---|---|---|
| | GAATTTCACCAGATCGAAGGAGTGGTCGCCGACCACGGGTTGACAC<br>TGGGTCATTTGATGGGGGTGCTGCGAGAATTTTTTACTAAGCTGGG<br>CATTACCCAACTCCGATTCAAACCAGCTTATAACCCCTATACAGAA<br>CCATCAATGGAAGTCTTCAGTTACCATCAAGGCCTCAAAAAGTGGG<br>TTGAAGTCGGCAATTCCGGCGTCTTTCGACCTGAAATGCTGCTCCC<br>CATGGGGCTTCCTGAAAACGTTAGTGTAATAGCCTGGGGGTTGTCT<br>CTTGAAAGGCCTACAATGATAAAATACGGGATTAATAATATCAGGG<br>AGCTGGTTGGCCATAAAGTAAACTTGCAGATGGTTTACGATAGCCC<br>CCTTTGCAGGCTCGACGCCGAACCACGGCCCCCACCCACACAGGAA<br>GCAGCATGA | |
| 11 | ATGGCAGACAACCCTGTTCTCGAACTGCTCTTGCGGCGGTTGGAAGT<br>AGCAGATGGAGGTTTGGATTCAGCAGAACTTGCCACCCAACTTGGCG<br>TTGAACATCAGGCCGTCGTTGGGGCAGTGAAGAGTCTGCAAGCACTC<br>GGGGAGGTGATAGAGGCTGAGCTTAGAAGTACAAAATGCTGGGAGTT<br>GACCACCGAGGGTGAAGAGATTGCTAGAGAAGGGAGTCACGAGGCAC<br>GCGTTTTTCGGAGTATACCTCTTGAAGGACTTGTGCAGTCAGAATTG<br>ATGCACCTTCCCTCAGGTAAGGTTGGATTTAGTAAAGCCATGAGTAA<br>TAAATGGATAAGAGTTGATAAATCAGCCGCCGACGGGCCAAGGGTGT<br>TTAGAGTCGTCGATTCTATAGAGGATGAAGTACAGAAAAGACTCCAA<br>CTGGTTCAGGCTGGACAAGCAGAAAAGCTCGCAGAAAAAGAACGGAA<br>TGAATTGAGAAAACGCAAACTGCTGACCGAAGTGATTTTGAAAACAT<br>ATTGGGTTTCAAAGGGGAAAGCATTTTCCACATCAGTGTCTAAGCAA<br>GAAGCCGAGCTCTCCCCTGAAATGATTTCTAGCGGAAGTTGGCGGGA<br>CCGACCATTCAAACCTTATAATTTCAGCGCAAGGGGAGTCCTTCCAG<br>ATTCAGGCCACCTCCACCCTCTTCTTAAAGTCCGCTCCCAGTTCCGG<br>CAGATCTTTCTGGAGATGGGGTTCACAGAAATGCCTACTGACAATTT<br>TATTGAGTCTAGCTTTTGGAATTTCGACGCACTCTTCCAGCCCCAAC<br>AGCACCCCGCAAGAGACCAACACGACACATTTTTTCTCAGGGATCCT<br>GCTGAAGCTCTCCAATTGCCAATGGGATACGTTCAGAGGGTGAAGAG<br>AACTCATTCACAAGGAGGATATGGTTCTCAGGGATATAAGTACACCT<br>GGAAGTTGGAAGAGGCTAGGAAAAATCTCTTGCGGACTCACACTACA<br>GCCGCCTCCGCTCGCGCTCTGTATCAGCTCGCACAAAAAAAGCCTTT<br>CACCCCAGCAAAATATTTCTCCATTGATCGCGTCTTCCGAAATGAAA<br>CATTGGATGCCACACATTTGGCTGAGTTCCACCAAATAGAAGGGGTC<br>ATCGCCGACCACGGTTTGACTCTTGGTCATTTGATGGGCGTATTGCG<br>CGAATTTTTCACCAAACTGGGGATTACACAGCTCCGATTTAAACCCG<br>CATACAACCCTTACACAGAGCCAAGTATGGAAGTGTTTAGCTATCAC<br>CAGGGGCTCAAGAAGTGGGTTGAAGTGGGAAATTCAGGAGTCTTTAG<br>GCCCGAGATGCTTCTTCCAATGGGCCTGCCAGAAAACGTGTCAGTAA<br>TTGCATGGGGTCTCTCCCTCGAGAGACCCACAATGATAAAGTACGGA<br>ATTAATAACATACGCGAGTTGGTTGGGCACAAGGTAAACCTTCAGAT<br>GGTCTATGACTCACCCGTCTGTAGACTTGATATAGAGCCTCGATCCA<br>GCAAAACACAGGAGGCTGCCTGA | MmPhe wild-type DNA sequence |

---

What is claimed is:

1. A method for labeling a proteome of a cell or a portion of the proteome of the cell, the method comprising:
   (a) introducing into the cell two or more variant aminoacyl-tRNA synthetases that recognize one or more noncanonical amino acids, wherein the two or more variant aminoacyl-tRNA synthetases comprise two or more of ScTyr$_{Y43G}$ of SEQ ID NO:4, the MmPhe$_{T413G}$ of SEQ ID NO:5, HsPheT$_{413G}$ of SEQ ID NO:6, and wherein the one or more noncanonical amino acids comprises 3-azido-L tyrosine (AzY), p-azido-L-phenylalanine (AzF), or a combination thereof;
   (b) subsequently exposing the cell to the one or more noncanonical amino acids, thereby integrating the one or more noncanonical amino acids into the proteome or the portion of the proteome, and producing a modified proteome; and
   (c) contacting the modified proteome with a detectable moiety, thereby producing a labeled proteome.

2. The method of claim 1, wherein the proteome or the portion of the proteome comprises a secretome of the cell or a portion thereof.

3. A method for labeling a protein or a portion of proteins produced by a cell, the method comprising:
   (a) introducing into the cell two or more variant aminoacyl-tRNA synthetases that recognize one or more noncanonical amino acids, wherein the two or more variant aminoacyl-tRNA synthetases comprise two or more of ScTyr$_{Y43G}$ of SEQ ID NO:4, the MmPhe$_{T413G}$ of SEQ ID NO:5, and HsPheT$_{413G}$ of SEQ ID NO:6, and wherein the one or more noncanonical amino acids comprise 3-azido-L tyrosine (AzY), p-azido-L-phenylalanine (AzF), or a combination thereof;
   (b) subsequently exposing the cell to the one or more noncanonical amino acids, thereby integrating the one or more noncanonical amino acids into the protein or population of proteins, and producing a modified protein or population of modified proteins; and
   (c) contacting the modified protein or population of modified proteins with a detectable moiety, thereby producing a labeled protein or population of labeled proteins.

4. The method of claim 3, wherein the protein or population of proteins produced by the cell is secreted by the cell.

5. The method of claim 1, wherein step (a) further comprises introducing into the cell two or more variant aminoacyl-tRNA synthetases that recognize one or more noncanonical amino acids, wherein the two or more variant aminoacyl-tRNA synthetases comprise ScTyr$_{Y43G}$ of SEQ ID NO:4, MmPhe$_{T413G}$ of SEQ ID NO:5, HsPhe$_{T413G}$ of SEQ ID NO:6, MmMet$^{L274G}$, pyrrolysyl-tRNA synthetase, or a combination thereof.

6. The method of claim 1, wherein the cell does not comprise an exogenous tRNA.

7. The method of claim 1, wherein the two or more variant aminoacyl-tRNA synthetases prefer to activate one or more tRNAs in the cell with the one or more noncanonical amino acids compared to a canonical amino acid.

8. The method of claim 1, wherein the detectable moiety comprises a fluorophore, an affinity resin, or a crosslinking reagent.

9. The method of claim 1, wherein the labeling is performed in vivo.

10. The method of claim 1, wherein the labeling is cell-type-specific.

11. The method of claim 1, wherein the labeling is temporally-restricted.

12. An isolated polynucleotide sequence that encodes a polypeptide with an amino acid sequence that is at least 85% identical to any one of MmPhe$_{T413G}$ of SEQ ID NO:5 or HsPhe$_{T413G}$ of SEQ ID NO:6.

13. The isolated polynucleotide of claim 12, wherein the polypeptide has the amino acid sequence of any one of MmPhe$_{T413G}$ of SEQ ID NO:5 or HsPhe$_{T413G}$ of SEQ ID NO:6.

14. A cell comprising a polynucleotide that encodes a polypeptide with an amino acid sequence that is at least 85% identical to any one of MmPhe$_{T413G}$ of SEQ ID NO:5 or HsPhe$_{T413G}$ of SEQ ID NO:6.

15. A kit for labeling a proteome of a cell, the kit comprising the isolated polynucleotide of claim 12.

16. A method for identifying a target cell, the method comprising:
   (a) labeling the proteome of the target cell according to the method of claim 1;
   (b) labeling the proteome of a reference cell according to the method of claim 1;
   (c) detecting the labeled proteome in the target cell and reference cell to generate a target cell signature and a reference cell signature, respectively;
   (d) comparing the target cell signature to the reference cell signature; and
   (e) identifying the target cell based on the comparison in step (d).

17. A method for identifying one or more biomarkers of interest in a target cell, the method comprising:
   (a) labeling the proteome of the target cell according to the method of claim 1;
   (b) labeling the proteome of a reference according to the method of claim 1;
   (c) detecting the labeled proteome in the target cell and reference cell to generate a target cell signature and a reference cell signature, respectively;
   (d) comparing the target cell signature to the reference cell signature; and
   (e) identifying the one or more biomarkers of interest based on the comparison in step (d).

18. The isolated polynucleotide of claim 12, wherein the isolated polynucleotide comprises the nucleic acid sequence of any one of SEQ ID NOS:2-3.

* * * * *

SEQUENCE LISTING

<160> NUMBER OF SEQ ID NOS: 11

<210> SEQ ID NO 1
<211> LENGTH: 1194
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atgtcctcag ctgccaccgt tgatccaaat gaagcttttg ggttgataac aaaaaacctc        60
caagaagtgt tgaaccctca gatcatcaag gatgtccttg aagtacaaaa aaggcatttg       120
aagctcgggt ggggaactgc ccctaccggg cgcccacatt gtgggtattt cgtccctatg       180
actaagttgg ctgatttctt gaaggcaggc tgcgaggtga ctgtgctcct ggccgacttg       240
cacgcctttt tggataatat gaaggcccct ctcgaggtcg tcaattatcg agccaagtac       300

```
tacgaactca ccattaaagc aatcttgagg agtataaacg tccctataga aaaacttaaa      360
tttgttgtag gttcttcata tcaactgaca cccgattata ccatggacat ttttagactg      420
agcaacattg tgtcccaaaa cgatgctaaa agagcaggag ctgacgttgt gaaacaagtt      480
gcaaacccac ttcttcagg cctgatatat cctcttatgc aagcactcga cgaacaattc       540
cttgatgtcg attgccagtt cggaggtgta gaccagcgaa aaatctttgt tttggccgaa      600
gagaacctgc cctctctggg ctataaaaaa cgggctcact tgatgaatcc aatggtcccc      660
ggattggccc aaggtggcaa aatgtctgca tcagacccca actctaaaat agatctgctg      720
gaggaaccaa agcaagttaa gaagaaaatt aactccgcct tttgcagtcc tggcaatgtc      780
gaggaaaacg ggcttctgtc attcgtgcag tatgtgatcg ccccaattca agaactcaag      840
ttcggtacaa atcattttga gttttttata gatcgaccag aaaaatttgg gggacctatt      900
acatacaaga gttttgaaga gatgaaattg gccttcaaag aagagaagct gagcccacct      960
gatctgaaga tcggagtggc cgacgccatc aatgagttgc ttgaaccaat acgacaggaa     1020
tttgctgata acaaagagtt tcaggaagct agtgaaaagg gctatcccgt agcaacccca     1080
caaaaatcta aaaagcaaa aaaacctaag aataagggta ctaaataccc tggggctacc      1140
aagactaatg aaattgctac taagctggag gagactaaat tgtaatgatg ataa           1194

<210> SEQ ID NO 2
<211> LENGTH: 1533
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atggcagaca accctgttct cgaactgctc ttgcggcggt tggaagtagc agatggaggt       60
ttggattcag cagaacttgc cacccaactt ggcgttgaac atcaggccgt cgttggggca      120
gtgaagagtc tgcaagcact cggggaggtg atagaggctg agcttagaag tacaaaatgc      180
tgggagttga ccaccgaggg tgaagagatt gctagagaag ggagtcacga ggcacgcgtt      240
tttcggagta tacctcttga aggacttgtg cagtcagaat tgatgcacct tccctcaggt      300
aaggttggat ttagtaaagc catgagtaat aaatggataa gagttgataa atcagccgcc      360
gacgggccaa gggtgtttag agtcgtcgat tctatagagg atgaagtaca gaaaagactc      420
caactggttc aggctggaca agcagaaaag ctcgcagaaa agaacggaa tgaattgaga       480 aaacgcaaac tgctgaccga agtgattttg aaaacatatt gggtttcaaa ggggaaagca      540
ttttccacat cagtgtctaa gcaagaagcc gagctctccc ctgaaatgat ttctagcgga      600
agttggcggg accgaccatt caaaccttat aatttcagcg caaggggagt ccttccagat      660
tcaggccacc tccaccctct tcttaaagtc cgctcccagt tccggcagat ctttctggag      720
atggggttca gaaatgcc tactgacaat tttattgagt ctagcttttg gaatttcgac        780
gcactcttcc agccccaaca gcaccccgca agagaccaac acgacacatt ttttctcagg     840
gatcctgctg aagctctcca attgccaatg ggatacgttc agagggtgaa gagaactcat     900
tcacaaggag gatatggttc tcagggatat aagtacacct ggaagttgga agaggctagg     960
aaaaatctct gcggactca cactacagcc gcctccgctc gcgctctgta tcagctcgca    1020
caaaaaaagc ctttcacccc agcaaaatat ttctccattg atcgcgtctt ccgaaatgaa    1080
acattggatg ccacacattt ggctgagttc caccaaatag aaggggtcat cgccgaccac    1140
```

```
ggtttgactc ttggtcattt gatgggcgta ttgcgcgaat ttttcaccaa actggggatt    1200
acacagctcc gatttaaacc cgcatacaac ccttacgggg agccaagtat ggaagtgttt    1260
agctatcacc aggggctcaa gaagtgggtt gaagtgggaa attcaggagt ctttaggccc    1320
gagatgcttc ttccaatggg cctgccagaa aacgtgtcag taattgcatg gggtctctcc    1380
ctcgagagac ccacaatgat aaagtacgga attaataaca tacgcgagtt ggttgggcac    1440
aaggtaaacc ttcagatggt ctatgactca cccgtctgta gacttgatat agagcctcga    1500
tccagcaaaa cacaggaggc tgcctgatga taa                                1533
```

<210> SEQ ID NO 3
<211> LENGTH: 1527
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
atggccgatg ggcaagtggc agagttgctc ctccggagac tcgaggctag tgacggagga     60
ctcgacagcg ctgagctcgc tgccgaactg gggatggagc accaagccgt ggtcggggct    120
gtcaagagct gcaggctttt gggtgaagtc atcgaggctg aactcaggag caccaaacac    180
tgggaactca cagcagaagg ggaagagata gctaggaagg tagccacgag gctcgggtt     240 tttcgctcca ttcacccgga ggacttgct cagtcagaac tcatgcggct tccaagtgga     300
aaagtaggat ttagcaaagc tatgagtaac aagtggatac gagtcgataa aagcgctgcc    360
gacggcccac gcgtattccg ggtggtggat agcatggaag atgaagtgca gcggaggctt    420
cagttggttc gcggagggca ggcagagaaa cttggtgaga aagagcgctc agaacttcgg    480
aagaggaagc tgctggccga agttaccctg aaaacttatt gggtgagtaa aggctccgcc    540
ttcagtacct ccatttccaa gcaggaaacc gagttgtctc cagagatgat tagttctgga    600
agttggcgcg acaggccatt caagccctac aactttctcg cacacggtgt gcttcccgat    660
tcaggtcatc tgcaccctct cctcaaagtt agatcacagt tccgccaaat cttttctggag    720 atggggttca ccgaaatgcc tacagataac ttcatcgaat ccagcttctg gaattttgac    780
gcactgtttc agccccaaca acaccccgcc agagatcagc acgacacatt cttcctgcga    840
gacccagccg aggctcttca gcttccaatg gattatgtgc agcgcgtaaa aagaactcat    900
agtcaaggcg ggtacggaag ccagggttat aagtacaatt ggaaactgga tgaagcaagg    960
aagaatctcc tccgcacaca tactacaagt gcatcagcca gagccctcta tcggctcgcc   1020
caaaagaagc cttttacccc agtgaagtat tttagcatcg accgggtgtt ccgcaacgag   1080
acactggatg ccactcacct ggctgaattt caccagatcg aaggagtggt cgccgaccac   1140
gggttgacac tgggtcattt gatggggtg ctgcgagaat ttttactaa gctgggcatt     1200 acccaactcc gattcaaacc agcttataac ccctatggag aaccatcaat ggaagtcttc   1260
agttaccatc aaggcctcaa aaagtgggtt gaagtcggca attccggcgt ctttcgacct   1320
gaaatgctgc tccccatggg gcttcctgaa aacgttagtg taatagcctg ggggttgtct   1380
cttgaaaggc ctacaatgat aaaatacggg attaataata tcagggagct ggttggccat   1440
aaagtaaact tgcagatggt ttacgatagc cccctttgca ggctcgacgc cgaaccacgg   1500
cccccaccca cacaggaagc agcatga                                        1527
```

<210> SEQ ID NO 4

```
<211> LENGTH: 394
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Ser Ser Ala Ala Thr Val Asp Pro Asn Glu Ala Phe Gly Leu Ile
1               5                   10                  15

Thr Lys Asn Leu Gln Glu Val Leu Asn Pro Gln Ile Ile Lys Asp Val
            20                  25                  30

Leu Glu Val Gln Lys Arg His Leu Lys Leu Gly Trp Gly Thr Ala Pro
        35                  40                  45

Thr Gly Arg Pro His Cys Gly Tyr Phe Val Pro Met Thr Lys Leu Ala
    50                  55                  60

Asp Phe Leu Lys Ala Gly Cys Glu Val Thr Val Leu Leu Ala Asp Leu
65                  70                  75                  80

His Ala Phe Leu Asp Asn Met Lys Ala Pro Leu Glu Val Val Asn Tyr
                85                  90                  95

Arg Ala Lys Tyr Tyr Glu Leu Thr Ile Lys Ala Ile Leu Arg Ser Ile
            100                 105                 110

Asn Val Pro Ile Glu Lys Leu Lys Phe Val Val Gly Ser Ser Tyr Gln
        115                 120                 125

Leu Thr Pro Asp Tyr Thr Met Asp Ile Phe Arg Leu Ser Asn Ile Val
    130                 135                 140

Ser Gln Asn Asp Ala Lys Arg Ala Gly Ala Asp Val Val Lys Gln Val
145                 150                 155                 160

Ala Asn Pro Leu Leu Ser Gly Leu Ile Tyr Pro Leu Met Gln Ala Leu
                165                 170                 175

Asp Glu Gln Phe Leu Asp Val Asp Cys Gln Phe Gly Gly Val Asp Gln
            180                 185                 190

Arg Lys Ile Phe Val Leu Ala Glu Glu Asn Leu Pro Ser Leu Gly Tyr
        195                 200                 205

Lys Lys Arg Ala His Leu Met Asn Pro Met Val Pro Gly Leu Ala Gln
    210                 215                 220

Gly Gly Lys Met Ser Ala Ser Asp Pro Asn Ser Lys Ile Asp Leu Leu
225                 230                 235                 240

Glu Glu Pro Lys Gln Val Lys Lys Ile Asn Ser Ala Phe Cys Ser
                245                 250                 255

Pro Gly Asn Val Glu Glu Asn Gly Leu Leu Ser Phe Val Gln Tyr Val
            260                 265                 270

Ile Ala Pro Ile Gln Glu Leu Lys Phe Gly Thr Asn His Phe Glu Phe
        275                 280                 285

Phe Ile Asp Arg Pro Glu Lys Phe Gly Gly Pro Ile Thr Tyr Lys Ser
    290                 295                 300

Phe Glu Glu Met Lys Leu Ala Phe Lys Glu Lys Leu Ser Pro Pro
305                 310                 315                 320

Asp Leu Lys Ile Gly Val Ala Asp Ala Ile Asn Glu Leu Leu Glu Pro
                325                 330                 335

Ile Arg Gln Glu Phe Ala Asp Asn Lys Glu Phe Gln Glu Ala Ser Glu
            340                 345                 350

Lys Gly Tyr Pro Val Ala Thr Pro Gln Lys Ser Lys Lys Ala Lys Lys
        355                 360                 365

Pro Lys Asn Lys Gly Thr Lys Tyr Pro Gly Ala Thr Lys Thr Asn Glu
```

```
            370                 375                 380
Ile Ala Thr Lys Leu Glu Glu Thr Lys Leu
385                 390

<210> SEQ ID NO 5
<211> LENGTH: 508
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Ala Asp Asn Pro Val Leu Glu Leu Leu Arg Arg Leu Glu Val
1               5                   10                  15

Ala Asp Gly Gly Leu Asp Ser Ala Glu Leu Ala Thr Gln Leu Gly Val
            20                  25                  30

Glu His Gln Ala Val Val Gly Ala Val Lys Ser Leu Gln Ala Leu Gly
            35                  40                  45

Glu Val Ile Glu Ala Glu Leu Arg Ser Thr Lys Cys Trp Glu Leu Thr
        50                  55                  60

Thr Glu Gly Glu Glu Ile Ala Arg Glu Gly Ser His Glu Ala Arg Val
65                  70                  75                  80

Phe Arg Ser Ile Pro Leu Glu Gly Leu Val Gln Ser Glu Leu Met His
                85                  90                  95

Leu Pro Ser Gly Lys Val Gly Phe Ser Lys Ala Met Ser Asn Lys Trp
            100                 105                 110

Ile Arg Val Asp Lys Ser Ala Ala Asp Gly Pro Arg Val Phe Arg Val
            115                 120                 125

Val Asp Ser Ile Glu Asp Glu Val Gln Lys Arg Leu Gln Leu Val Gln
        130                 135                 140

Ala Gly Gln Ala Glu Lys Leu Ala Glu Lys Glu Arg Asn Glu Leu Arg
145                 150                 155                 160

Lys Arg Lys Leu Leu Thr Glu Val Ile Leu Lys Thr Tyr Trp Val Ser
                165                 170                 175

Lys Gly Lys Ala Phe Ser Thr Ser Val Ser Lys Gln Glu Ala Glu Leu
            180                 185                 190

Ser Pro Glu Met Ile Ser Ser Gly Ser Trp Arg Asp Arg Pro Phe Lys
            195                 200                 205

Pro Tyr Asn Phe Ser Ala Arg Gly Val Leu Pro Asp Ser Gly His Leu
        210                 215                 220

His Pro Leu Leu Lys Val Arg Ser Gln Phe Arg Gln Ile Phe Leu Glu
225                 230                 235                 240

Met Gly Phe Thr Glu Met Pro Thr Asp Asn Phe Ile Glu Ser Ser Phe
                245                 250                 255

Trp Asn Phe Asp Ala Leu Phe Gln Pro Gln His Pro Ala Arg Asp
            260                 265                 270

Gln His Asp Thr Phe Phe Leu Arg Asp Pro Ala Glu Ala Leu Gln Leu
        275                 280                 285

Pro Met Gly Tyr Val Gln Arg Val Lys Arg Thr His Ser Gln Gly Gly
    290                 295                 300

Tyr Gly Ser Gln Gly Tyr Lys Tyr Thr Trp Lys Leu Glu Glu Ala Arg
305                 310                 315                 320

Lys Asn Leu Leu Arg Thr His Thr Thr Ala Ala Ser Ala Arg Ala Leu
                325                 330                 335
```

-continued

```
Tyr Gln Leu Ala Gln Lys Lys Pro Phe Thr Pro Ala Lys Tyr Phe Ser
                340                 345                 350

Ile Asp Arg Val Phe Arg Asn Glu Thr Leu Asp Ala Thr His Leu Ala
            355                 360                 365

Glu Phe His Gln Ile Glu Gly Val Ile Ala Asp His Gly Leu Thr Leu
        370                 375                 380

Gly His Leu Met Gly Val Leu Arg Glu Phe Phe Thr Lys Leu Gly Ile
385                 390                 395                 400

Thr Gln Leu Arg Phe Lys Pro Ala Tyr Asn Pro Tyr Gly Glu Pro Ser
                405                 410                 415

Met Glu Val Phe Ser Tyr His Gln Gly Leu Lys Lys Trp Val Glu Val
            420                 425                 430

Gly Asn Ser Gly Val Phe Arg Pro Glu Met Leu Leu Pro Met Gly Leu
        435                 440                 445

Pro Glu Asn Val Ser Val Ile Ala Trp Gly Leu Ser Leu Glu Arg Pro
    450                 455                 460

Thr Met Ile Lys Tyr Gly Ile Asn Asn Ile Arg Glu Leu Val Gly His
465                 470                 475                 480

Lys Val Asn Leu Gln Met Val Tyr Asp Ser Pro Val Cys Arg Leu Asp
                485                 490                 495

Ile Glu Pro Arg Ser Ser Lys Thr Gln Glu Ala Ala
            500                 505

<210> SEQ ID NO 6
<211> LENGTH: 508
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ala Asp Gly Gln Val Ala Glu Leu Leu Arg Arg Leu Glu Ala
1               5                   10                  15

Ser Asp Gly Gly Leu Asp Ser Ala Glu Leu Ala Ala Glu Leu Gly Met
                20                  25                  30

Glu His Gln Ala Val Gly Ala Val Lys Ser Leu Gln Ala Leu Gly
            35                  40                  45

Glu Val Ile Glu Ala Glu Leu Arg Ser Thr Lys His Trp Glu Leu Thr
        50                  55                  60

Ala Glu Gly Glu Ile Ala Arg Glu Gly Ser His Glu Ala Arg Val
65                  70                  75                  80

Phe Arg Ser Ile Pro Pro Glu Gly Leu Ala Gln Ser Glu Leu Met Arg
                85                  90                  95

Leu Pro Ser Gly Lys Val Gly Phe Ser Lys Ala Met Ser Asn Lys Trp
            100                 105                 110

Ile Arg Val Asp Lys Ser Ala Ala Asp Gly Pro Arg Val Phe Arg Val
        115                 120                 125

Val Asp Ser Met Glu Asp Glu Val Gln Arg Arg Leu Gln Leu Val Arg
    130                 135                 140

Gly Gly Gln Ala Glu Lys Leu Gly Glu Lys Glu Arg Ser Glu Leu Arg
145                 150                 155                 160

Lys Arg Lys Leu Leu Ala Glu Val Thr Leu Lys Thr Tyr Trp Val Ser
                165                 170                 175

Lys Gly Ser Ala Phe Ser Thr Ser Ile Ser Lys Gln Glu Thr Glu Leu
            180                 185                 190
```

Ser Pro Glu Met Ile Ser Ser Gly Ser Trp Arg Asp Arg Pro Phe Lys
            195                 200                 205

Pro Tyr Asn Phe Leu Ala His Gly Val Leu Pro Asp Ser Gly His Leu
    210                 215                 220

His Pro Leu Leu Lys Val Arg Ser Gln Phe Arg Gln Ile Phe Leu Glu
225                 230                 235                 240

Met Gly Phe Thr Glu Met Pro Thr Asp Asn Phe Ile Glu Ser Ser Phe
                245                 250                 255

Trp Asn Phe Asp Ala Leu Phe Gln Pro Gln His Pro Ala Arg Asp
            260                 265                 270

Gln His Asp Thr Phe Phe Leu Arg Asp Pro Ala Glu Ala Leu Gln Leu
            275                 280                 285

Pro Met Asp Tyr Val Gln Arg Val Lys Arg Thr His Ser Gln Gly Gly
            290                 295                 300

Tyr Gly Ser Gln Gly Tyr Lys Tyr Asn Trp Lys Leu Asp Glu Ala Arg
305                 310                 315                 320

Lys Asn Leu Leu Arg Thr His Thr Ser Ala Ser Ala Arg Ala Leu
                325                 330                 335

Tyr Arg Leu Ala Gln Lys Lys Pro Phe Thr Pro Val Lys Tyr Phe Ser
            340                 345                 350

Ile Asp Arg Val Phe Arg Asn Glu Thr Leu Asp Ala Thr His Leu Ala
            355                 360                 365

Glu Phe His Gln Ile Glu Gly Val Val Ala Asp His Gly Leu Thr Leu
    370                 375                 380

Gly His Leu Met Gly Val Leu Arg Glu Phe Phe Thr Lys Leu Gly Ile
385                 390                 395                 400

Thr Gln Leu Arg Phe Lys Pro Ala Tyr Asn Pro Tyr Gly Glu Pro Ser
                405                 410                 415

Met Glu Val Phe Ser Tyr His Gln Gly Leu Lys Lys Trp Val Glu Val
            420                 425                 430

Gly Asn Ser Gly Val Phe Arg Pro Glu Met Leu Leu Pro Met Gly Leu
    435                 440                 445

Pro Glu Asn Val Ser Val Ile Ala Trp Gly Leu Ser Leu Glu Arg Pro
    450                 455                 460

Thr Met Ile Lys Tyr Gly Ile Asn Asn Ile Arg Glu Leu Val Gly His
465                 470                 475                 480

Lys Val Asn Leu Gln Met Val Tyr Asp Ser Pro Leu Cys Arg Leu Asp
                485                 490                 495

Ala Glu Pro Arg Pro Pro Thr Gln Glu Ala Ala
            500                 505

<210> SEQ ID NO 7
<211> LENGTH: 394
<212> TYPE: PRT
<213> ORGANISM: Saccharomyces cerevisiae

<400> SEQUENCE: 7

Met Ser Ser Ala Ala Thr Val Asp Pro Asn Glu Ala Phe Gly Leu Ile
1               5                   10                  15

Thr Lys Asn Leu Gln Glu Val Leu Asn Pro Gln Ile Ile Lys Asp Val
                20                  25                  30

Leu Glu Val Gln Lys Arg His Leu Lys Leu Tyr Trp Gly Thr Ala Pro
            35                  40                  45

Thr Gly Arg Pro His Cys Gly Tyr Phe Val Pro Met Thr Lys Leu Ala

```
                    50                  55                  60
Asp Phe Leu Lys Ala Gly Cys Glu Val Thr Val Leu Ala Asp Leu
 65                  70                  75                  80

His Ala Phe Leu Asp Asn Met Lys Ala Pro Leu Glu Val Val Asn Tyr
                     85                  90                  95

Arg Ala Lys Tyr Tyr Glu Leu Thr Ile Lys Ala Ile Leu Arg Ser Ile
                100                 105                 110

Asn Val Pro Ile Glu Lys Leu Lys Phe Val Val Gly Ser Ser Tyr Gln
                115                 120                 125

Leu Thr Pro Asp Tyr Thr Met Asp Ile Phe Arg Leu Ser Asn Ile Val
            130                 135                 140

Ser Gln Asn Asp Ala Lys Arg Ala Gly Ala Asp Val Val Lys Gln Val
145                 150                 155                 160

Ala Asn Pro Leu Leu Ser Gly Leu Ile Tyr Pro Leu Met Gln Ala Leu
                165                 170                 175

Asp Glu Gln Phe Leu Asp Val Asp Cys Gln Phe Gly Gly Val Asp Gln
            180                 185                 190

Arg Lys Ile Phe Val Leu Ala Glu Glu Asn Leu Pro Ser Leu Gly Tyr
            195                 200                 205

Lys Lys Arg Ala His Leu Met Asn Pro Met Val Pro Gly Leu Ala Gln
210                 215                 220

Gly Gly Lys Met Ser Ala Ser Asp Pro Asn Ser Lys Ile Asp Leu Leu
225                 230                 235                 240

Glu Glu Pro Lys Gln Val Lys Lys Lys Ile Asn Ser Ala Phe Cys Ser
                245                 250                 255

Pro Gly Asn Val Glu Glu Asn Gly Leu Leu Ser Phe Val Gln Tyr Val
                260                 265                 270

Ile Ala Pro Ile Gln Glu Leu Lys Phe Gly Thr Asn His Phe Glu Phe
            275                 280                 285

Phe Ile Asp Arg Pro Glu Lys Phe Gly Gly Pro Ile Thr Tyr Lys Ser
            290                 295                 300

Phe Glu Glu Met Lys Leu Ala Phe Lys Glu Lys Leu Ser Pro Pro
305                 310                 315                 320

Asp Leu Lys Ile Gly Val Ala Asp Ala Ile Asn Glu Leu Leu Glu Pro
                325                 330                 335

Ile Arg Gln Glu Phe Ala Asp Asn Lys Glu Phe Gln Glu Ala Ser Glu
            340                 345                 350

Lys Gly Tyr Pro Val Ala Thr Pro Gln Lys Ser Lys Lys Ala Lys Lys
            355                 360                 365

Pro Lys Asn Lys Gly Thr Lys Tyr Pro Gly Ala Thr Lys Thr Asn Glu
            370                 375                 380

Ile Ala Thr Lys Leu Glu Glu Thr Lys Leu
385                 390

<210> SEQ ID NO 8
<211> LENGTH: 508
<212> TYPE: PRT
<213> ORGANISM: Mus musculus

<400> SEQUENCE: 8

Met Ala Asp Asn Pro Val Leu Glu Leu Leu Arg Arg Leu Glu Val
 1               5                  10                  15

Ala Asp Gly Gly Leu Asp Ser Ala Glu Leu Ala Thr Gln Leu Gly Val
                20                  25                  30
```

```
Glu His Gln Ala Val Val Gly Ala Val Lys Ser Leu Gln Ala Leu Gly
         35                  40                  45

Glu Val Ile Glu Ala Glu Leu Arg Ser Thr Lys Cys Trp Leu Thr
 50                  55                  60

Thr Glu Gly Glu Glu Ile Ala Arg Gly Ser His Glu Ala Arg Val
 65              70                  75                  80

Phe Arg Ser Ile Pro Leu Glu Gly Leu Val Gln Ser Glu Leu Met His
                 85                  90                  95

Leu Pro Ser Gly Lys Val Gly Phe Ser Lys Ala Met Ser Asn Lys Trp
            100                 105                 110

Ile Arg Val Asp Lys Ser Ala Ala Asp Gly Pro Arg Val Phe Arg Val
            115                 120                 125

Val Asp Ser Ile Glu Asp Glu Val Gln Lys Arg Leu Gln Leu Val Gln
130                 135                 140

Ala Gly Gln Ala Glu Lys Leu Ala Glu Lys Glu Arg Asn Glu Leu Arg
145                 150                 155                 160

Lys Arg Lys Leu Leu Thr Glu Val Ile Leu Lys Thr Tyr Trp Val Ser
                165                 170                 175

Lys Gly Lys Ala Phe Ser Thr Ser Val Ser Lys Gln Glu Ala Glu Leu
            180                 185                 190

Ser Pro Glu Met Ile Ser Ser Gly Ser Trp Arg Asp Arg Pro Phe Lys
            195                 200                 205

Pro Tyr Asn Phe Ser Ala Arg Gly Val Leu Pro Asp Ser Gly His Leu
            210                 215                 220

His Pro Leu Leu Lys Val Arg Ser Gln Phe Arg Gln Ile Phe Leu Glu
225                 230                 235                 240

Met Gly Phe Thr Glu Met Pro Thr Asp Asn Phe Ile Glu Ser Ser Phe
                245                 250                 255

Trp Asn Phe Asp Ala Leu Phe Gln Pro Gln His Pro Ala Arg Asp
                260                 265                 270

Gln His Asp Thr Phe Phe Leu Arg Asp Pro Ala Glu Ala Leu Gln Leu
            275                 280                 285

Pro Met Gly Tyr Val Gln Arg Val Lys Arg Thr His Ser Gln Gly Gly
290                 295                 300

Tyr Gly Ser Gln Gly Tyr Lys Tyr Thr Trp Lys Leu Glu Glu Ala Arg
305                 310                 315                 320

Lys Asn Leu Leu Arg Thr His Thr Thr Ala Ser Ala Arg Ala Leu
                325                 330                 335

Tyr Gln Leu Ala Gln Lys Lys Pro Phe Thr Pro Ala Lys Tyr Phe Ser
            340                 345                 350

Ile Asp Arg Val Phe Arg Asn Glu Thr Leu Asp Ala Thr His Leu Ala
            355                 360                 365

Glu Phe His Gln Ile Glu Gly Val Ile Ala Asp His Gly Leu Thr Leu
    370                 375                 380

Gly His Leu Met Gly Val Leu Arg Glu Phe Phe Thr Lys Leu Gly Ile
385                 390                 395                 400

Thr Gln Leu Arg Phe Lys Pro Ala Tyr Asn Pro Tyr Thr Glu Pro Ser
                405                 410                 415

Met Glu Val Phe Ser Tyr His Gly Leu Lys Lys Trp Val Glu Val
                420                 425                 430

Gly Asn Ser Gly Val Phe Arg Pro Glu Met Leu Leu Pro Met Gly Leu
            435                 440                 445

Pro Glu Asn Val Ser Val Ile Ala Trp Gly Leu Ser Leu Glu Arg Pro
```

```
                450             455             460
Thr Met Ile Lys Tyr Gly Ile Asn Asn Ile Arg Glu Leu Val Gly His
465                 470                 475                 480

Lys Val Asn Leu Gln Met Val Tyr Asp Ser Pro Val Cys Arg Leu Asp
                485                 490                 495

Ile Glu Pro Arg Ser Ser Lys Thr Gln Glu Ala Ala
                500                 505

<210> SEQ ID NO 9
<211> LENGTH: 508
<212> TYPE: PRT
<213> ORGANISM: Homo sapiens

<400> SEQUENCE: 9

Met Ala Asp Gly Gln Val Ala Glu Leu Leu Arg Arg Leu Glu Ala
1               5                   10                  15

Ser Asp Gly Gly Leu Asp Ser Ala Glu Leu Ala Ala Glu Leu Gly Met
                20                  25                  30

Glu His Gln Ala Val Val Gly Ala Val Lys Ser Leu Gln Ala Leu Gly
            35                  40                  45

Glu Val Ile Glu Ala Glu Leu Arg Ser Thr Lys His Trp Glu Leu Thr
50                  55                  60

Ala Glu Gly Glu Glu Ile Ala Arg Glu Gly Ser His Glu Ala Arg Val
65                  70                  75                  80

Phe Arg Ser Ile Pro Pro Glu Gly Leu Ala Gln Ser Glu Leu Met Arg
                85                  90                  95

Leu Pro Ser Gly Lys Val Gly Phe Ser Lys Ala Met Ser Asn Lys Trp
                100                 105                 110

Ile Arg Val Asp Lys Ser Ala Ala Asp Gly Pro Arg Val Phe Arg Val
            115                 120                 125

Val Asp Ser Met Glu Asp Glu Val Gln Arg Arg Leu Gln Leu Val Arg
130                 135                 140

Gly Gly Gln Ala Glu Lys Leu Gly Glu Lys Glu Arg Ser Glu Leu Arg
145                 150                 155                 160

Lys Arg Lys Leu Leu Ala Glu Val Thr Leu Lys Thr Tyr Trp Val Ser
                165                 170                 175

Lys Gly Ser Ala Phe Ser Thr Ser Ile Ser Lys Gln Glu Thr Glu Leu
                180                 185                 190

Ser Pro Glu Met Ile Ser Ser Gly Ser Trp Arg Asp Arg Pro Phe Lys
            195                 200                 205

Pro Tyr Asn Phe Leu Ala His Gly Val Leu Pro Asp Ser Gly His Leu
            210                 215                 220

His Pro Leu Leu Lys Val Arg Ser Gln Phe Arg Gln Ile Phe Leu Glu
225                 230                 235                 240

Met Gly Phe Thr Glu Met Pro Thr Asp Asn Phe Ile Glu Ser Ser Phe
                245                 250                 255

Trp Asn Phe Asp Ala Leu Phe Gln Pro Gln His Pro Ala Arg Asp
            260                 265                 270

Gln His Asp Thr Phe Phe Leu Arg Asp Pro Ala Glu Ala Leu Gln Leu
            275                 280                 285

Pro Met Asp Tyr Val Gln Arg Val Lys Arg Thr His Ser Gln Gly Gly
            290                 295                 300

Tyr Gly Ser Gln Gly Tyr Lys Tyr Asn Trp Lys Leu Asp Glu Ala Arg
305                 310                 315                 320
```

```
Lys Asn Leu Leu Arg Thr His Thr Thr Ser Ala Ser Ala Arg Ala Leu
                325                 330                 335

Tyr Arg Leu Ala Gln Lys Lys Pro Phe Thr Pro Val Lys Tyr Phe Ser
            340                 345                 350

Ile Asp Arg Val Phe Arg Asn Glu Thr Leu Asp Ala Thr His Leu Ala
        355                 360                 365

Glu Phe His Gln Ile Glu Gly Val Val Ala Asp His Gly Leu Thr Leu
    370                 375                 380

Gly His Leu Met Gly Val Leu Arg Glu Phe Phe Thr Lys Leu Gly Ile
385                 390                 395                 400

Thr Gln Leu Arg Phe Lys Pro Ala Tyr Asn Pro Tyr Thr Glu Pro Ser
                405                 410                 415

Met Glu Val Phe Ser Tyr His Gln Gly Leu Lys Lys Trp Val Glu Val
            420                 425                 430

Gly Asn Ser Gly Val Phe Arg Pro Glu Met Leu Leu Pro Met Gly Leu
        435                 440                 445

Pro Glu Asn Val Ser Val Ile Ala Trp Gly Leu Ser Leu Glu Arg Pro
    450                 455                 460

Thr Met Ile Lys Tyr Gly Ile Asn Asn Ile Arg Glu Leu Val Gly His
465                 470                 475                 480

Lys Val Asn Leu Gln Met Val Tyr Asp Ser Pro Leu Cys Arg Leu Asp
                485                 490                 495

Ala Glu Pro Arg Pro Pro Thr Gln Glu Ala Ala
            500                 505

<210> SEQ ID NO 10
<211> LENGTH: 1527
<212> TYPE: DNA
<213> ORGANISM: Homo sapiens

<400> SEQUENCE: 10
atggccgatg ggcaagtggc agagttgctc ctccggagac tcgaggctag tgacggagga      60
ctcgacagcg ctgagctcgc tgccgaactg ggatggagc accaagccgt ggtcggggct      120
gtcaagagct tgcaggcttt gggtgaagtc atcgaggctg aactcaggag caccaaacac      180
tgggaactca cagcagaagg ggaagagata gctagggaag gtagccacga ggctcgggtt      240
tttcgctcca ttccacccga gggacttgct cagtcagaac tcatgcggct tccaagtgga      300
aaagtaggat ttagcaaagc tatgagtaac aagtggatac gagtcgataa aagcgctgcc      360
gacggcccac gcgtattccg ggtggtggat agcatggaag atgaagtgca gcggaggctt      420
cagttggttc gcggagggca ggcagagaaa cttggtgaga agagcgctc agaacttcgg      480 aagaggaagc tgctggccga agttaccctg aaaacttatt gggtgagtaa aggctccgcc      540
ttcagtacct ccatttccaa gcaggaaacc gagttgtctc cagagatgat tagttctgga      600
agttggcgcg acaggccatt caagccctac aactttctcg cacacggtgt gcttcccgat      660
tcaggtcatc tgcaccctct cctcaaagtt agatcacagt tccgccaaat ctttctggag      720
atggggttca ccgaaatgcc tacagataac ttcatcgaat ccagcttctg gaattttgac      780
gcactgtttc agccccaaca cacccccgcc agagatcagc acgacacatt cttcctgcga      840
gacccagccg aggctcttca gcttccaatg gattatgtgc agcgcgtaaa aagaactcat      900
agtcaaggcg ggtacggaag ccagggttat aagtacaatt ggaaactgga tgaagcaagg      960
aagaatctcc tccgcacaca tactacaagt gcatcagcca gagccctcta tcggctcgcc     1020
caaaagaagc cttttacccc agtgaagtat tttagcatcg accgggtgtt ccgcaacgag     1080
```

```
acactggatg ccactcacct ggctgaattt caccagatcg aaggagtggt cgccgaccac   1140
gggttgacac tgggtcattt gatggggtg ctgcgagaat tttttactaa gctgggcatt   1200
acccaactcc gattcaaacc agcttataac ccctatacag aaccatcaat ggaagtcttc   1260
agttaccatc aaggcctcaa aaagtgggtt gaagtcggca attccggcgt ctttcgacct   1320
gaaatgctgc tccccatggg gcttcctgaa aacgttagtg taatagcctg ggggttgtct   1380
cttgaaaggc ctacaatgat aaaatacggg attaataata tcagggagct ggttggccat   1440
aaagtaaact tgcagatggt ttacgatagc ccccttttgca ggctcgacgc cgaaccacgg   1500 ccccccaccca cacaggaagc agcatga                                      1527

<210> SEQ ID NO 11
<211> LENGTH: 1527
<212> TYPE: DNA
<213> ORGANISM: Mus musculus

<400> SEQUENCE: 11
atggcagaca accctgttct cgaactgctc ttgcggcggt tggaagtagc agatggaggt     60
ttggattcag cagaacttgc cacccaactt ggcgttgaac atcaggccgt cgttggggca   120
gtgaagagtc tgcaagcact cggggaggtg atagaggctg agcttagaag tacaaaatgc   180
tgggagttga ccaccgaggg tgaagagatt gctagagaag ggagtcacga ggcacgcgtt   240
tttcggagta tacctcttga aggacttgtg cagtcagaat tgatgcacct tccctcaggt   300
aaggttggat ttagtaaagc catgagtaat aaatggataa gagttgataa atcagccgcc   360
gacgggccaa gggtgtttag agtcgtcgat tctatagagg atgaagtaca gaaaagactc   420
caactggttc aggctggaca agcagaaaag ctcgcagaaa agaacggaa tgaattgaga   480 aaacgcaaac tgctgaccga agtgattttg aaaacatatt gggtttcaaa ggggaaagca   540
ttttccacat cagtgtctaa gcaagaagcc gagctctccc ctgaaatgat ttctagcgga   600
agttggcggg accgaccatt caaaccttat aatttcagcg caaggggagt ccttccagat   660
tcaggccacc tccaccctct tcttaaagtc cgctcccagt tccggcagat cttttctggag   720 atggggttca cagaaatgcc tactgacaat tttattgagt ctagcttttg gaatttcgac   780
gcactcttcc agccccaaca gcaccccgca agagaccaac acgacacatt ttttctcagg   840
gatcctgctg aagctctcca attgccaatg ggatacgttc agagggtgaa gagaactcat   900
tcacaaggag gatatggttc cagggatat aagtacacct ggaagttgga agaggctagg   960
aaaaatctct tgcggactca cactacagcc gcctccgctc gcgctctgta tcagctcgca   1020
caaaaaaagc ctttcacccc agcaaaatat ttctccattg atcgcgtctt ccgaaatgaa   1080
acattggatg ccacacattt ggctgagttc caccaaatag aaggggtcat cgccgaccac   1140
ggtttgactc ttggtcattt gatgggcgta ttgcgcgaat ttttcaccaa actgggggatt   1200 acacagctcc gatttaaacc cgcatacaac ccttacacag agccaagtat ggaagtgttt   1260
agctatcacc aggggctcaa gaagtgggtt gaagtgggaa attcaggagt ctttaggccc   1320
gagatgcttc ttccaatggg cctgccagaa aacgtgtcag taattgcatg ggtctctcc   1380 ctcgagagac ccacaatgat aaagtacgga attaataaca tacgcgagtt ggttgggcac   1440
aaggtaaacc ttcagatggt ctatgactca cccgtctgta gacttgatat agagcctcga   1500
tccagcaaaa cacaggaggc tgcctga                                       1527
```